US006159710A

United States Patent [19]
Fraser et al.

[11] Patent Number: 6,159,710
[45] Date of Patent: *Dec. 12, 2000

[54] METHOD AND COMPOSITIONS FOR STABILIZING UNSTABLE GENE TRANSCRIPTS

[75] Inventors: Nigel W. Fraser, Merion Station, Pa.; Janice M. Zabolotny, Brookline, Mass.; Claude F. Krummenacher, Philadelphia, Pa.

[73] Assignee: The Wistar Institute of Anatomy and Biology, Philadelphia, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 09/403,267

[22] PCT Filed: Apr. 17, 1998

[86] PCT No.: PCT/US98/07691

§ 371 Date: Oct. 15, 1999

§ 102(e) Date: Oct. 15, 1999

[87] PCT Pub. No.: WO98/48004

PCT Pub. Date: Oct. 29, 1998

Related U.S. Application Data

[60] Provisional application No. 60/044,664, Apr. 18, 1997.

[51] Int. Cl.$^7$ ...................................................... C12P 21/02

[52] U.S. Cl. .......................... 435/69.1; 435/357; 435/365; 435/320.1; 435/455; 536/23.1; 536/24.1

[58] Field of Search .................................... 435/69.1, 357, 435/365, 320.1, 455; 536/23.1, 24.1

[56] References Cited

FOREIGN PATENT DOCUMENTS

WO 98/48004  10/1998  WIPO.

OTHER PUBLICATIONS

Spicer et al., *Mol. Cell. Biol.*, vol. 12, pp. 1324–1329, Mar. 1992.
L. Balvay et al., "Pre–mRNA Secondary Structure and the Regulation of Splicing", *Bioessays*, 15(3):165–169 (Mar. 1993).
A.H. Batchelor and P. O'Hare, "Regulations and Cell–Type–Specific Activity of a Promoter Located Upstream of the Latency–Associated Transcript of Herpes Simplex Virus Type I", *J. Virol.*, 64(7):3269–3279 (Jul. 1990).
T.M. Block et al., "A Herpes Simplex Virus Type 1 Latency–Associated Transcript Mutant Reactivates with Normal Kinetics from Latent Infection", *J. Virol.*, 64(7):3417–3426 (Jul. 1990).
R.A. Bohenzky et al., "Two Overlapping Transcription Units Which Extend Across the L–S Junction of Herpes Simplex Virus Type 1", *J. Virol.*, 69(5):2889–2897 (May 1995).
K.B. Chapmand and J.D. Boeke, "Isolation and Characterization of the Gene Encoding Yeast Debranching Enzyme", *Cell*, 65:483–492 (May 3, 1991).

X. Chen et al., "Two Herpes Simplex Virus Type a Latency–Active Promoters Differ in Their Contributions to Latency–Associated Transcript Expression during Lytic and Latent Infections", *J. Virol.*, 69(12):7899–7909 (Dec. 1995).
D.W. Copertino and R.B. Hallick, "Group II Twintron: An Intron within an Intron in a Chloroplast Cytochrome b–559 Gene", *EMBO J.*, 10(2):433–442 (Feb. 1991).
G.B. Devi–Rao et al., "Relationship between Polyadenylated and Nonpolyadenylated Herpes Simplex Virus Type 1 Latency–Associated Transcripts", *J. Virol.*, 65(5):2179–2190 (May 1991).
A.T. Dobson et al., "Identification of the Latency–Associated Transcript Promoter by Expression of Rabbit Beta–Globin mRNA in Mouse Sensory Nerve Ganglia Latently Infected with a Recombinant Herpes Simplex Virus", *J. Virol.*, 63(9):3844–3851 (Sep. 1989).
M.J. Farrell et al., "Herpes Simplex Virus Latency–Associated Transcript is a Stable Intron", *Proc. Natl. Acad. Sci. USA.*, 88: 790–794 (Feb. 1991).
G.A. Freyer et al., "In vitro Formation of a Lariat Structure Containing a $G^{2'}-{}^{5'}G$ Linkage", *J. Biol. Chem.*, 262(9):4267–4273 (Mar. 25, 1987).
W. F. Goins et al., "A Novel Latency–Active Promoter is Contained within the Herpes Simplex Virus Type 1 $U_L$ Flanking Repeats", *J. Virol.*, 68(4):2239–2252 (Apr. 1994).
H. Hornig et al., "Effect of Mutations at then Lariat Branch Acceptor Site on β–Globin Pre–mRNA Splicing in Vitro", *Nature*, 324:589–591 (Dec. 1986).
S.K. Jang et al., "Cap–Independent Translation of Encephalomyocarditis Virus RNA:Structural Elements of the Internal Ribosomal Entry Site and Involvement of a Cellular 57–kD RNA–Binding Protein", *Genes and Devel.*, 4:1560–1572 (Sep. 1990).
P.R. Krause et al., "The Nucleotide Sequence, 5' End, Promoter Domain, and Kinetics of Expression of the Gene Encoding the Herpes Simplex Virus Type 2 Latency–Associated Transcript", *J. Virol.* 65(10):5619–5623 (Oct. 1991).
P.R. Krause et al., "Structural and Kinetic Analyses of Herpes Simplex Virus Type 1 Latency–Associated Transcripts in Human Trigeminal Ganglia and in Cell Culture", *J. Clin. Invest.*, 86:235–241 (Jul. 1990).
M. Lagunoff and B. Roizman, "The Regulation of Synthesis and Properties of the Protein Product of Open Reading Frame P of the Herpes Simplex Virus 1 Genome", *J. Virol.* 69:3615–3623 (Jun. 1995).

(List continued on next page.)

*Primary Examiner*—James Ketter
*Attorney, Agent, or Firm*—Howson and Howson

[57] ABSTRACT

A polynucleotide molecule useful for stably producing a gene product includes a polynucleotide sequence encoding the gene product (or alternatively a gene transcript) flanked by a 5' sequence and a 3' of an intron. Methods and compositions using this molecule permit enhanced recombinant expression of the gene product and are particularly useful in stabilizing unstable mRNA transcripts, permitting the stable production of desirable genes encoded thereby. Vectors and host cells containing this molecule are useful in the methods.

27 Claims, 31 Drawing Sheets

OTHER PUBLICATIONS

M. Lagunoff and B. Roizman "Expression of a Herpes Simplex Virus 1 Open Reading Frame Antisense to the $\gamma_1 34.5$ Gene and Transcribed by an RNA 3' Coterminal with the Unspliced Latency–Associated Transcript", *J. Virol.* 68:6021–6028 (Sep. 1994).

M. Lagnuoff et al., "Phenotypic Properties of Herpes Simplex Virus 1 containing a Derepressed Open Reading Frame P Gene", *J. Virol.,* 70:1810–1817 (Mar. 1996).

D.J. McGeoch et al., "The complete DNA Sequence of the Long Unique Region int eh Genome of Herpes Simplex Virus Type 1" *J. Gen. Virol.,* 69:1531–1574 (Jul. 1988).

W.J. Mitchell et al., "Mapping of Low Abundance Latency–Associated RNA in the Trigeminal Ganglia of Mice Latently Infected with Herpes Simplex Virus Type 1", *J. Gen. Virol.,* 71:125–132 (Jan. 1990).

M. Nicosia et al., "The HSV–1 2–kb Latency–Associated Transcript is Found in the Cytoplasm Comigrating with Ribosomal Subunits During Productive Infection", *Virol.,* 204:717–728 (Nov. 1, 1994).

M. Nicosia et al., "Herpes Simplex Virus Type 1 Latency–Associated Transcript (LAT) Promoter Deletion Mutants can Express a 2–Kilobase Transcript Mapping to the LAT Region", *J. Virol.,* 67:7276–7283 (Dec. 1993).

D.L. Rock et al., "Detection of Latency–Related Viral RNAs in Trigeminal Ganglia of Rabbits Latently Infected with Herpes Simplex Virus Type 1", *J. Virol.,* 61:3820–3826 (Dec. 1987).

N.M. Sawtell and R.L. Thompson, "Herpes Simplex Virus Type 1 Latency–Associated Transcription Unit Promotes Anatomical Site–Dependent Establishment and Reactivation from Latency", *J. Virol.,* 66:2157–2169 (Apr. 1992).

D.B. Spicer et al., "An Antisense Promoter of the Murine c–myc Gene is Localized within Intron 2", *Molecular and Cellular Biology,* 12(3):1324–1329 (Mar. 1992).

J. Singh and E. K. Wagner, "Transcriptional Analysis of the Herpes Simplex Virus Type 1 Region Containing the $TR_L$/$U_L$ Junction" *Virol.,* 196:220–231 (Sep. 1993).

J.G. Spivack and N.W. Fraser "Detection of Herpes Simplex Virus Type 1 Transcripts During Latent Infection in Mice", *J. Virol.,* 61(12):3841–3847 (Dec. 1987).

J.G. Spivack et al., "Identification of a Novel Latency–Specific Splice Donor Signal Within the Herpes Simplex Virus Type 1 2.0–Kilobase Latency–Associated Transcript (LAT): Translation of LAT Open Reading Frames by the Intron within the 2.0–Kilobase LAT", *J. Virol.,* 65:6800–6810 (Dec. 1991).

J.G. Spivack and N.W. Fraser, "Expression of Herpes Simplex Virus Type 1 Latency–Associated Transcripts in the trigeminal Ganglia of Mice During Acute Infection and Reactivation of Latent Infection", *J. Virol.,* 62(5):3281–3287 (May 1988).

I. Steiner et al., "Herpes Simplex Virus Type 1 Latency–Associated Transcripts are Evidently not Essential for Latent Infection", *EMBO J.,* 8(2):505–511 (Feb. 1989).

J.G. Stevens et al., "RNA Complementary to Herpesvirus a Gene mRNA in Prominent in Latently Infected Neurons", *Science,* 235:1056–1059 (Feb. 1987).

E.K. Wagner et al., "Physical Characterization of the Herpes Simplex Virus Latency–Associated Transcript in Neurons", *J. Virol.* 62(4):1194–1202 (Apr. 1988).

S.L. Wechsler et al., "Fine Mapping of the Latency–Related Gene of Herpes Simplex Virus Type 1: Alternative Splicing Produces Distinct Latency–Related RNAs Containing Open Reading Frames", *J. Virol.,* 62(11):4051 (Nov. 1988).

T.T. Wu et al., "Evidence that Two Latency–Associated Transcripts of Herpes Simplex Virus Type 1 Are Nonlinear", *J. Virol.,* 70(9):5962–5967 (Sep. 1996).

L. Yeh and P.A. Schaffer, "A Novel Class of Transcripts Expressed with Late Kinetics in the Absence of ICP4 Spans the Junction Between the Long and Short Segments of the Herpes Simplex Virus Type 1 Genome", *J. Virol.* 67(12):7373–7382 (Dec. 1993).

J.C. Zwaagstra et al., "Activity of Herpes Simplex Virus Type 1 Latency–Associated Transcript (LAT) Promoter in Neuron–Derived Cells: Evidence for Neuron Specificity and for a Large LAT Transcript", *J. Virol.* 64(10):5019–5028 (Oct. 1990).

J. Zwaagstra et al., "In Vitro Promoter Activity Associated with the Latency–Associated Transcript Gene of Herpes Simplex Virus Type 1", *J. Gen. Virol.* 70:2163–2169 (Aug. 1989).

J.C. Zwaagstra et al., "Identification of a Major Regulatory Sequence in the Latency Associated Transcript (LAT) Promoter of Herpes Simplex Virus Type 1 (HSV–1)", *Virol.,* 182:287–297 (May 1991).

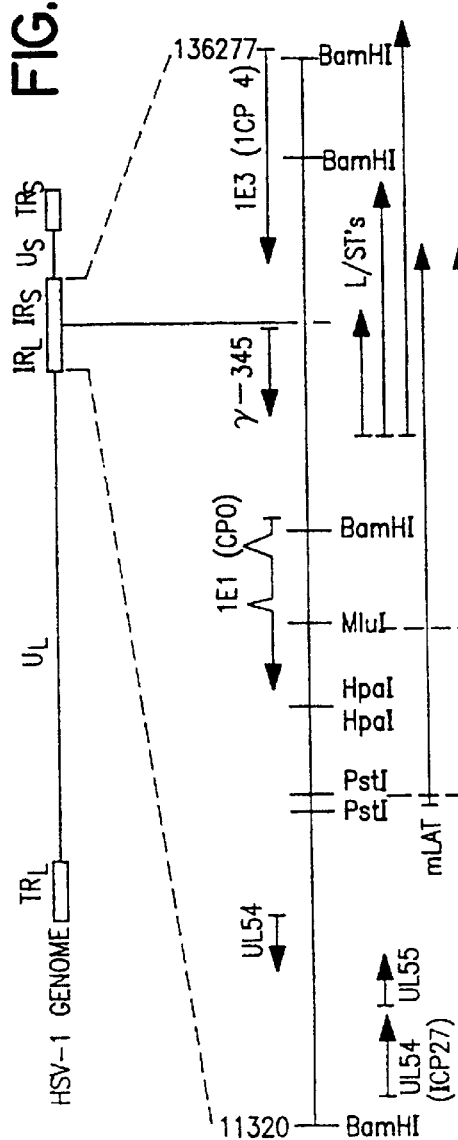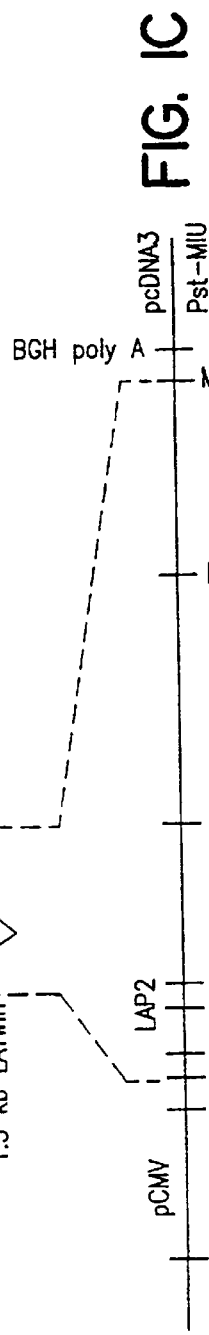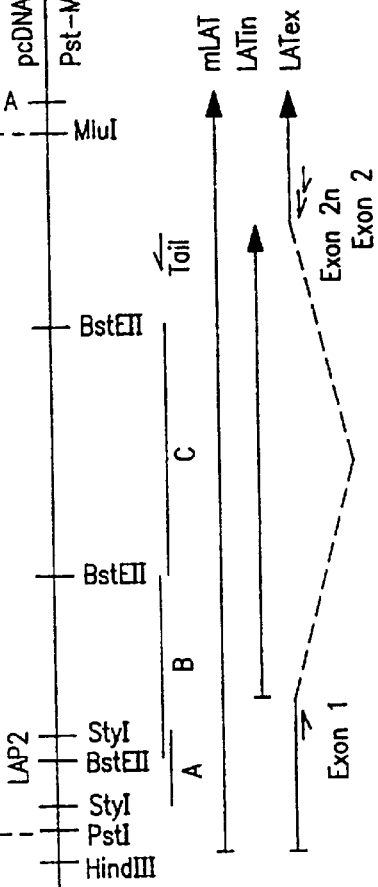

HSV-1    5'.....CCCCCGAGAUGGGCAGGUAGCGCGUGAGGCCGCCCGCGGGGAC        GGCCCCGGAAGU                        CUCCCGCGUGGCGCG....3'
              ||||||||||||||||||||||||||||||||||||||||||||||        ||||||||||||                        |||||||||||||||
HSV-2    5'.....CCCCCGCGAUGGGCAGGUAGCGCGUGAGGCGCGCCCGCGGGUCGCGGACGGGGCGCGGGCUCGGGGCCGCCCGCGGGGCCGCGGGCUCGGGCCUCCCGCGUGGCGCG....3'

HSV-1    5'.....UCUUCCGGGCACACUUCCUGCCCCCGGCCCGGCGCCCAGAAGCAGCCGAGGGAGGAGGUUUCCUCUGUCUCCUCCCAG                              3'
              ||||||||||||||||||||||||||||||||||||||||||||||||||||||||||||||||||||||||||||||
HSV-2    5'.....UCUUCCUGGCACACUUCCUGCCCCUGGCGCCCCGGGC        GCAGCAGCCGGGGGCCGAGGGAGGAGGUUUCCUCGU        CUCUCCCCAG          3'

Consensus 5'......YNYURAC..........(N)n..............YYYYYYYYYY(Y)m(N)xAG    3'

FIG. 5

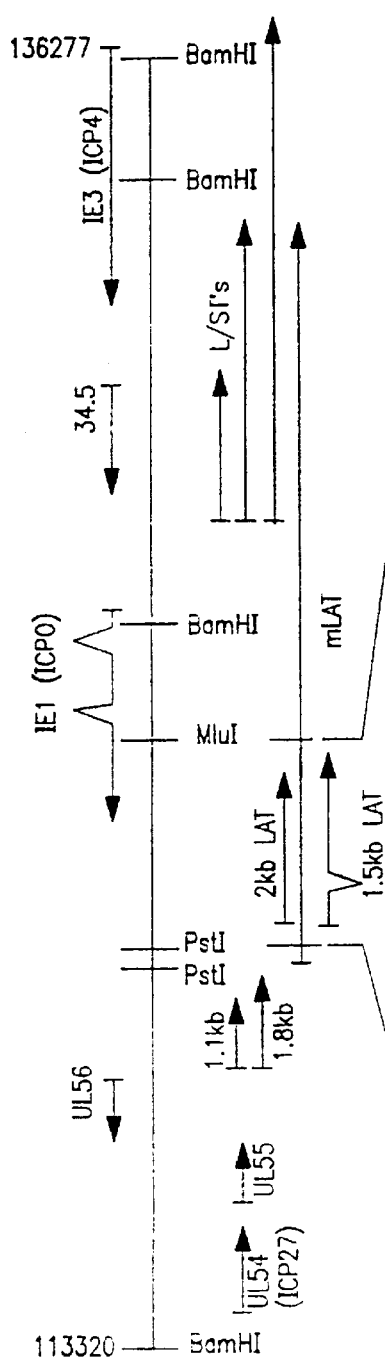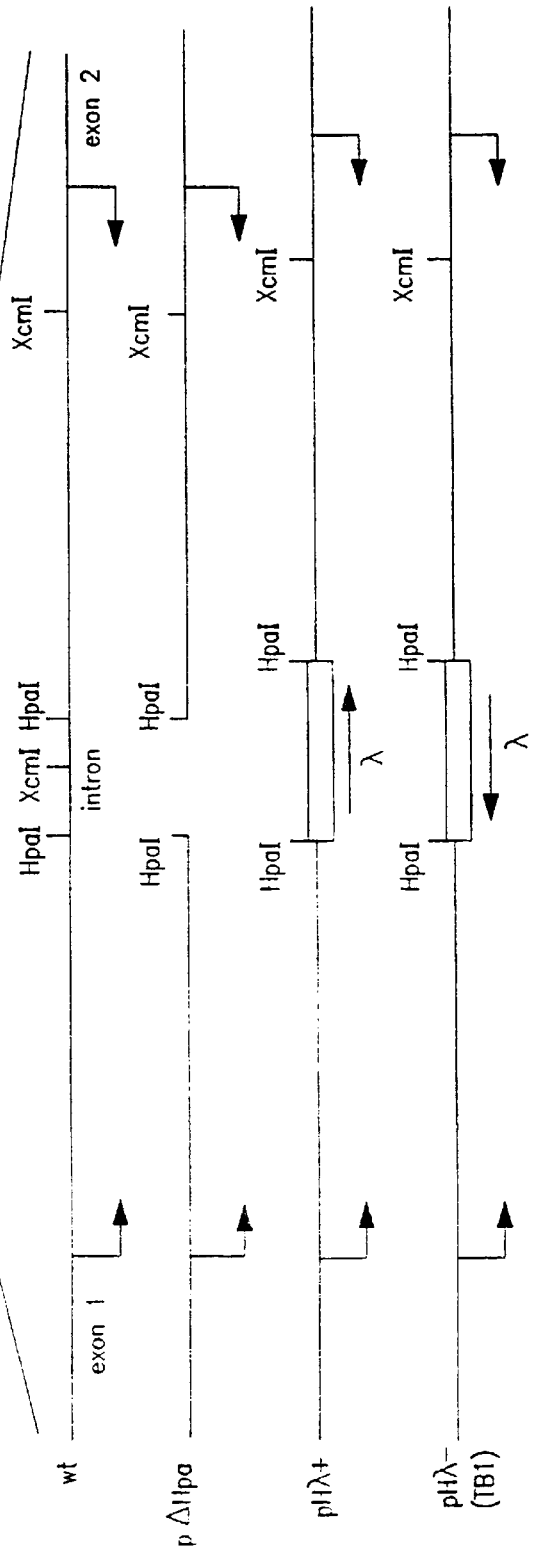
FIG. 7A
FIG. 7B
FIG. 7C

```
                 121324                                          121370
                 |                       •                       |
wt      TCCGCGTGGCGCGTCTTCCGGGCACACTTCCTCGGCCCCCGCGGCCC
pCons   TCCGCGTGGCGCGTCTTCCGGGCACACTTCCTCGGCCCCCGCGGCCC
pΔA     TCCGCGTGGCGCGTCTTCCGGGCACACTTCCTCGGCCCCCGCGGCCC
pΔG     TCCGCGTGGCGCGTCT-------ACACTTCCTCGGCCCCCGCGGCCC
pΔ#5    TCCGCGTGGCGCGTCTTCCGGGCACACTTCCTCGG------------
pBam    TCCGCGTGGCGCGTCTTCCGGGCACACTTCCTCGGCCCCCGCGGCCC 121371                                          121418
                 |                     o                         |
wt      AGAAGCAGCGCGGGGGCCGAGGGAGGTTTCCTCTTGTCTCCCTCCCAG
pCons   AGAAGCAGCGCGGGGGCC[CA][CT]GA[CC]TTTCCTCTTGTCTCCCTCCCAG
pΔA     AGAAGCAGCGCGGGGGCC--------TTTCCTCTTGTCTCCCTCCCAG
pΔG     AGAAGCAGCGCGGGGGCCGAGGGAGGTTTCCTCTTGTCTCCCTCCCAG
pΔ#5    ------------------GAGGGAGGTTTCCTCTTGTCTCCCTCCCAG
pBam    AGAAGCAGCGCGGGGGCCGAGGGA[TCC]TTCCTCTTGTCTCCCTCCCAG
                                        ∧
                               ╱           ╲
                pY+     GATCGTACTAAC
                pY-     GATCGTTAGTAC
```

FIG. 9B

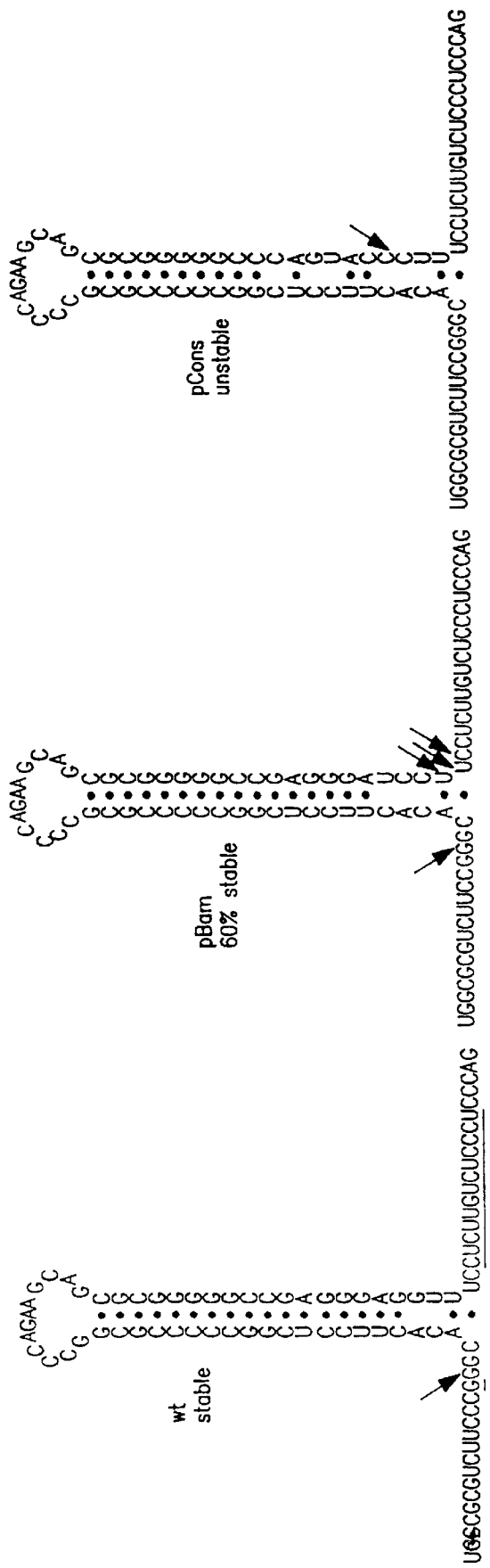

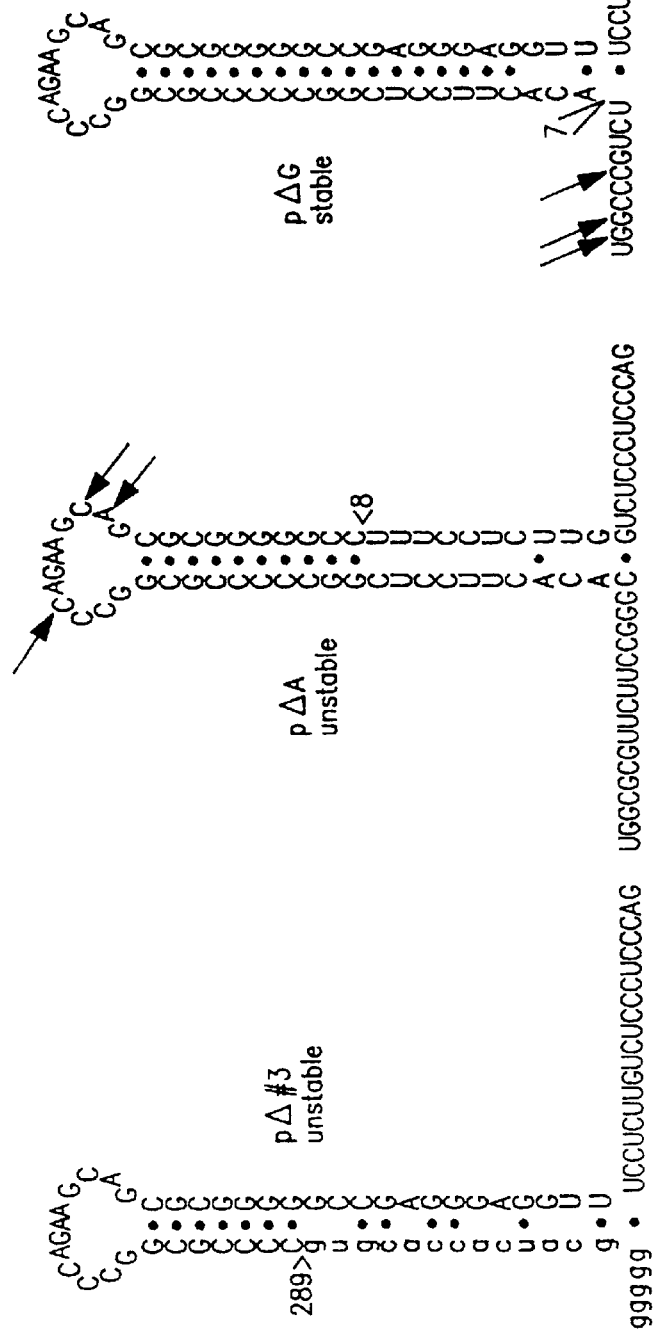

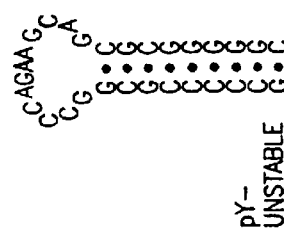
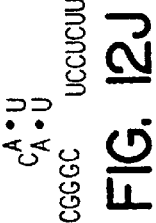
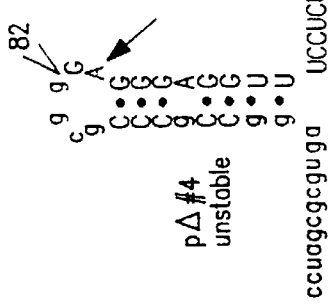
FIG. 12I
FIG. 12H
FIG. 12G
FIG. 12J

FIGURE 15A

SEQUENCE OF THE mLAT AND LAT REGION OF HSV-1 (STRAIN 17)

117000
CCAGCCAAGTTAACGGGCTACGCCTTCGGGAATGGGACTGGCACCCCGGCGGATTTTGTT
         Hpal 117060
GGGCTGGCATGCGTCGCCCAACCGAGGGCCGCGTCCACGGGACGCGCCTTTTATAACCCC
                                            TFIID binding site for UL56

117120
GGGGGTCATTCCCAACGATCACATGCAATCTAACTGGCTCCCCTCTCCCCCCTCTCCCC
                                    $U_L/IR_L$   Reiteration 1

117180
TCTCCCCCCTCTCCCCTCTCCCCCCCTCTCCCCTCTCCCCCCTCTCCCCTCTCCCCCC

117240
CTCTCCCCTCTCCCCCCTCTCCCCTCTCCCCCCTCTCCCCTCTCCCCCCCTCTCCCCT

117300
CTCCCCCTCTCCCCTCTCCCCCCCTCTCCCCCTCTCCCCTCTGCTCTTTCCCCGTGACA

117360
CCCGACGCTGGGGGCGTGGCTGCCGGGAGGGGCCGCGGATGGGCGGGCCTACTTGGTTTC

117420
CCGCCCCCCCCCCCCCCCCCCGAACCGCCCCGCCGGCTTTGCCCCCCTTTGATCCCCTGC

117480
TACCCCCAACCCGTGCTGGTGGTGCGGGTTGGGGGGGGATGTGGGCGGGGGTGCGCGGGA

117540
GGTGTCGGTGGTGGTGGTGGTGGTGGTAGTAGGAATGGTGGTGAGGGGGGGGGGCGCTG
         Reiteration 2

117600
GTTGGTCAAAAAGGGAGGGACGGGGGCCGGCAGACCGACGGCGACAACGCTCCCCGGCG

117660
GCCGGGTCGCGGCTCTTACGAGCGGCCCGGCCCGCGCTCCCACCCCCGGGCCGTGTCCT

FIGURE 15B

117720
TGCTTTCCCCCCGTCTCCCCCCCCCCGCCTTCTCCTCCTCCTCCTCGTTTTTCCAAACC

117780
CCGCCCACCCGGCCCGGCCCGGCCCGGCCCGGCCACCGCCGCCCACCCACCCACC
        Reiteration 3

117840
TCGGGATACCCAGCCCCGGTCCCCCGTTCCCCGGGGGCCGTTATCTCCAGCGCCCCGTCC

117900
GGCGCGCCGCCCCCGCCGCTAAACCCCATCCCGCCCCCGGGACCCCACATATAAGCCCC

117960
CAGCCACACGCAAGAACAGACACGCAGAACGGCTGTGTTTATTTAAATAAACCAATGTCG
                                                      Swa1(Dra1)

118020
GAATAAACAAACACAAACACCCGCGACGGGGGGACGGAGGGGACGGAGGGAGGGGGTGAC

118080
GGGGGACGGGAACAGACACAAAAACAACCACAAAAAACAACCACCCACCGACACCCCAC

118140
CCCAGTCTCCTCGCCTTCTCCCACCCACCCCACGCCCCCACTGAGCCCGGTCGATCGACG
                                            splice branch ?

118200
AGCACCCCCGCCCACGCCCCCGCCCCTGCCCCGGCGACCCCCGGCCCGCACGATCCCGAC

118260
AACAATAACAACCCCAACGGAAAGCGGCGGGGTGTTGGGGGAGGCGAGGAACAACCGAGG

118320
GGAACGGGGGATGGAAGGACGGGAAGTGGAAGTCCTGATACCCATCCTACACCCCCTGC

118380
CTTCCACCCTCCGGCCCCCGCGAGTCCACCCGCCGGCCGGCTACCGAGACCGAACACGG

118440
CGGCCGCCGCAGCCGCCGCAGCCGCCGCCGACACCGCAGAGCCGGCGCGCGCACTCACAA

118500
GCGGCAGAGGCAGAAAGGCCCAGAGTCATTGTTTATGTGGCCGCGGGCCAGCAGACGGCC

FIGURE 15C

118560
CGCGACACCCCCCCCCGCCCGTGTGGGTATCCGGCCCCCCGCCCCGCGCCGGTCCATTA

118620
AGGGCGCGCGTGCCCGCGA<u>GATATC</u>AATCCGTTAAGTGCT<u>CTGCAG</u>ACAGGGGCACCGCG
          EcoRV        Pst1

118680
CCCGGAAATCCATTAGGCCGCAGACGAGGAAAATAAAATTACATCACCTAC<u>CCACGTGG</u>T
                            USF/MLTF
                            Myc/Max

118740
GCTGTGGCCTGTTTTTGC<u>TGCGTCAT</u>CTCAGCCTTT<u>TATAAAAG</u>CGGGGG<u>CG</u>CGGCCGTGC
         CRE     TF11D/LAT  Egr-1

118800
CGATCGCGGGTGGTGCGAA<u>AGACTTTC</u>CGGGCGCGTCCGGGTGCCGCGGCTCTCCGGGCC
      ICP4   Heat Shock?

118860
CCC<u>CTGCAG</u>CCGGGGCGGCCAAGGGGCGTCGGCGACATCCTCCCCCTAAGCGCCGGCCGG
   Pst1

118920
CCGCTGGTCTGTTTTTTCGTTTTCCCCGTTTCGGGGGTGGTGGGGGTTGCGGTTTCTGTT

118980
TCTTTAACCCGTCTGGGGTGTTTTTCGTTCCGTCGCCGGAATGTTTCGTTCGTCTGTCCC

119040
CTCACGGGGCGAAGGCCGCGTACGGCCCGGGACGAGGGCCCCCGACCGCGGCGGTCCGG

119100
GCCCCGTCCGGACCCGCTCGCCGGCACGCGACGCGAAAAAGGCCCCCCGGAGGCTTTTCC

119160
GGGTTCCCGGCCCGGGGCCTGAGATGAACACTCGGGGTTACCGCCAACGGCCGGCCCCCG

119220
TGGCGGCCCGGCCCGGGGCCCCGGCGGACCCAAGGGGCCCCGGCCCGGGGCCCCACAACG

119280
GCCCGGCGCATGCGCTGTGGTTTTTTTTTTCCTCGGTGTTCTGCCGGGCTCCATCGCCTTT
                                        ICP4 binding?

FIGURE 15D

119340
CCTGTTCTCGCTTCTCCCCCCCCCTTCTTCACCCCCAGTACCCTCCTCCCTCCCTTCCT

119400
CCCCCGTTATCCCACTCGTCGAGGGCGCCCCGGTGTCGTTCAACAAAGACGCCGCGTTTC

119460
CA<u>GG</u>TAGGTTAGACACCTGCTTCTCCCCAATAGAGGGGGGGGACCCAAACGACAGGGCGC
   start of 2kb LAT RNA

119520
GCCCCAGAGGCTAAGGTCGGCCACGCCACTCGCGGGTGGGCTCGTGTTACAGCACACCAG

119580
CCCGTTCTTTTCCCCCCCTCCCACCCTTAGTCAGACTCTGTTACTTACCCGTCCGACCAC

119640
CAACTGCCCCCTTATCTAAGGGCCGGCTGGAAGACCCCAGGGGGTCGGCCGGTGTCGCT

119700
GTAACCCCCACGCCAATGACCCACGTACTCCAAGAAGGCATGTGTCCCACCCCGCCTGT
               5'LAT intron/exon 119760
GTTTTTGTGCCTGGCTCTCTATGCTTGGGTCTTACTGCCTGGGGGGGGGAGTGCGGGGG
                            Homol. Rat U1 RNA

119820
AGGGGGGTGTGGAAGGAAATGCACGGCGCCTGTGTACCCCCCTAAAGTTGTTCCTAAA

119880
GCGAGGATACGGAGGAGTGGCGGGTGCCGGGGGACCGGGGTGATCTCTGGCACGCGGGGG

119940
TGGGAAGGGTCGGGGGAGGGGGGGATGGAGTACCGGCCCACCTGGCCGCGCGGGTGCGCG

120000
TGCCTTTGCACACCAACCCCACGTCCCCGGCGGTCTCTAAGAAGCACCGCCCCCCCTCC

120060
TTCATACCACCGAGCATGCCTGGGTGTGGGTTGGTAACCAACAGGCCCATCCCCTCGTCT

120120
CCTGTGATTCTCTGGCTGCACCGCATTCTTGTTTTCTAACTATGTTCCTGTTTCTGTCTC

120180
CCCCCCCCCACCCCTCCGCCCCACCCCCAACACCCACGTCTGTGGTGTGGCCGACCCC

FIGURE 15E

```
120240
CTTTTGGGCGCCCCGTCCCGCCCCGCCACCCCTCCCATCCTTTGTTGCCCTATAGTGTAG
                                                 3' LAT  exon/intron 120300
TTAACCCCCCCCGCCCTTTTGTGGCGGCCAGAGGCCAGGTCAGTCCGGGCGGGCAGGGGT
Hpa1                                  Hormone recpt. ½ site

120360
CGCGGAAACTTAACACCCACACCCAACCCACTGTGGTTCTGGCTCCATGCCAGTGGCAGG

120420
ATGCTTTCCGGGATCGGTGGTCAGGCAGCCCGGGCCGCGGCTCTGTGGTTAACACCAGAG
ORF-1                                                Hpa1

120480
CCTGCCCAACATGGCACCCCACTCCCACGCACCCCACTCCCACGCACCCCACTCCCA
     ORF-2   Reiteration 4

120540
CGCACCCCACTCCCACGCACCCCACTCCCACGCACCCCACTCCCACGCACCCCACT

120600
CCCACGCACCCCACTCCCACGCACCCCACTCCCACGCATCCCCGCGATACATCCAACA

120660
CAGACAGGGAAAAGATACAAAAGTAAACCTTTATTTCCCAACAGACAGCAAAAATCCCCT
                                3' end ICP0

120720
GAGTTTTTTTTTATTAGGGCCAACACAAAAGACCCGCTGGTGTGTGGTGCCCGTGTCTTT

120780
CACTTTTCCCCTCCCCGACACGGATTGGCTGGTGTAGTCGGCGCGGCCAGAGACCACCCA
                                  Stop ORF-2

120840
GCGCCCGACCCCCCCTCCCCACAAACACGGGGGGCGTCCCTTATTGTTTTCCCTCGTCC

120900
CGGGTCGACGCCCCTGCTCCCCGGACCACGGGTGCCGAGACCGCAGGCTGCGGAAGTCC

120960
AGGGCGCCCACTAGGGTGCCCTGGTCGAACAGCATGTTCCCCACGGGGGTCATCCAGAGG

121020
CTGTTCCACTCCGACGCGGGGGCCGTCGGGTACTCGGGGGGCATCACGTGGTTACCCGCG
```

FIGURE 15F

```
121080
GTCTCGGGGAGCAGGGTGCGGCGGCTCCAGCCGGGGACCGCGGCCCGCAGCCGGGTCGCC

121140
ATGTTTCCCGTCTGGTCCACCAGGACCACGTACGCCCCGATGTTCCCCGTCTCCATGTCC

121200
AGGATGGGCAGGCAGTCCCCCGTGATAGTCTTGTTCACGTAAGGCGACAGGGCCACCACG
                                                Stop ORF-1

121260
CTAGAGACCCCCGAGATGGGCAGGTAGCGCGTGAGGCCGCCCGCGGGGACGGCCCCGGAA

121320
GTCTCCGCGTGGCGCGTCTTCCGGGCACACTTCCTCGGCCCCCGCGGCCCAGAAGCAGCG
              splice branch 121380
CGGGGGCCGAGGGAGGTTTCCTCTTGTCTCCCTCCCAGGGCACCGACGGCCCCGCCCGAG
                                     last nucleotide in 2kb LAT

121440
GAGGCGGAAGCGGAGGAGGACGCGGCCCCGGCGGCGGAAGAGGCGGCCCCCGCGGGGGTC

121500
GGGGCCGAGGAGGAAGAGGCAGAGGAGGAAGAGGCGGAGGCCGCCGAGGACGTCAGGGGG

121560
GTCCCGGGCCCACCCTGGCCGCGCCCCCCGGCCCTGAGTCGGAGGGGGGTGCGTCGCC

121620
GCCCTCTTGGCCCCTGCCGGCGCGAGGGGGGGACGCGTGGACTGGGGGGAGCGGTTTTCC
                                    MluI

121680
TGGCCCGACCCGCGCCTCTTCCTCGGACGCACCGCCGCCTCCTGCTCGACAGAGGCGGCG

121740
GAGGGGAGCGGGGCGGCGCCGGAGGGGGCGGCGCCGCGGGAGGGCCCGTGCCCACCCTCC

121800
ACGCCCGGCCCCCCGAGCCGCGCGCCACCGTCGCACGCGCCCGGCACAGACTCTGTTCT

121860
TGGTTCGCGGCCTGAGCCAGGGACGAGTGCGACTGGGGCACACGGCGCGCGTCCGCGGGG

121920
CGGGCGGCCGGCTCCGCCCCGGGGGCGGGGCGCGGGGCCGGGCCCCGGAGGGCGCCGC
```

FIGURE 15G

121980
CGCACGCACGGGGCCACGGCCGCGCGGGGGCGCGCGGGTCCCGACGCGGCCGCGGACGCG

122040
GGGGGCCCGGGGCGGGGGGCGGAGCCTGGCATGGGCGCCGCGGGGGGCCTGTGGGGAGAG

122100
GCCGGGGGGGAGTCGCTGATCACTATGGGTCTCTGTTGTTTGCAAGCGGGGCGGGTCTG

122160
TTGACAAGGGGGCCCGTCCGGCCCCTCGGCCGCCCCGCCTCCGCTTCAACAACCCCAACC

122220
CCAACCCCAACCCCCCGGAGGGGCCAGACGCCCCCGCGGCGCCGCGGCTCGCGACTGG

122280
CGGGAGCCGCCGCCGCCGCTGCTGTTGGTGGTGGTGTTGGTGTTACTGCTGCCGTGTGGC

122340
CCGATGGGCGCCGAGGGGGGCGCTGTCCGAGCCGCCGCCGGCTGGGGGGCTGCGTGAGAC

122400
GCCCCGCCCGTCACGGGGGGCGCGGCGGCCCCTCTGCGTGGGGGGGCGCGGGGCGTCCGG

122460
CGGGGGGCGGGCGGTACGTAGTCTGCTGCAAGAGACAACGGGGGGCGCGATCAGGTTACG

122520
CCCCCTCCCCGGCCCGCCCTTTCCTCGCCCGCCCGCCTATTCCTCCCTCCCCCCCCCTCC
          ICP0 intron 2

122580
TCCTCCTCCTCCCCCAGGGTCCTTGCCGCCCCCGCCTCACCGTCGTCCAGGTCGTCGTC

122640
ATCCTCGTCCGTGGTGGGCTCCGGGTGGGTGGGCGACAGGGCCCTCACCGTCTGCCCCCC

122700
CAGGGTCAGGTACCGCGGGGCGAACCGCTGATTGCCCGTCCAGATAAAGTCCACGGCCGT

122760
GCCCGCCCTGACGGCCTCCTCGGCCTCCATGCGGGTCTGGGGGTCGTTCACGATCGGGAT

122820
GGTGCTGAACGACCCGCTGGGCGTCACGCCCACTATCAGGTACACCAGCTTGGCGTTGCA

FIGURE 15H

122880
CAGCGGGCAGGTGTTGCGCAATTGCATCCAGGTTTTCATGCACGGGATGCAGAAGCGGTG

122940
CATGCACGGGAAGGTGTCGCAGCGCAGGTGGGGCGCGATCTCATCCGTGCACACGGCGCA

123000
CACGTCGCCCTCGTCGCTCCCCCCGTCCTCTCGAGGGGGGGCGCCCCCGCAACTGCCGGG

123060
GTCTTCCTCGCGGGGGGGGCTCCCCCCGAGACCGCCCCCCCATCCACGCCCTGCGGCCC

123120
CAGCAGCCCCGTCTCGAACAGTTCCGTGTCCGTGCTGTCCGCCTCGGAGGCGGAGTCGTC

123180
GTCATGGTGGTCGGCGTCCCCCCGCCCCCCACTTCGGTCTCCGCCTCAGAGTCGCTGCT

123240
GTCCGGCAGGTCTCGGTCGCAGGGAAACACCCAGACATCCGGGGCGGGCTAAGGGGAAAA

123300
AAGGGGGGCGGGTAAGAATGGGGGGGGGATTTCCCGCGTCAATCAGCACCCACGAGTTCCC
                                NF-kB   /E2F

123360
CCTCTCCCCCCCCGCCTCACAAAGTCCTGCCCCCCTGCTGGCCTCGGAAGAGGGGGAG

123420
AAAGGGGTCTGCAACCAAAGGTGGTCTGGGTCCGTCCTTTGGATCCCGACCCCTCTTCTT
                                            BamH1

123480
CCCTCTTCTCCCGCCCTCCAGACGCACCGGAGTCGGGGGTCCCACGGCGTCCCCCAAATA

123540
TGGCGGGCGGCTCCTCCCCACCCCCTAGATGCGTGTGAGTAAGGGGGGCCTGCGTATGA

123600
GTCAGTGGGGACCACGCCCCAACACGGCGACCCCGGTCCTTGTGTGTTTGTTGTGGGGG
branch point              ICP0 intron 1

123660
CGTGTCTCTGTGTATGAGTCAGGGGGTCCCACGGCGACCCCGGGCCCTGCGTCTGAGTCA

123720
AAGGGGCCATGTGTATGTGTTGGGGGTCTGTATATATAAAGTCAGGGGGTCACATGGCGA

FIGURE 15I

123780
CCCCCAACAGGGCGACCCCGGTCCCTGTATATAGGGTCAGGGGGTTCCGCACCCCCTA

123840
ACATGGCGCCCCGGTCCCTGTATATAGTGTCACGGGGTTCCACGCCCCCTAACATGG

123900
CGCCCCAACATGGCGCCCGGCTCCCGTGTATGAGTGGGGGTCCCCCAACATGGCGGCCGG

123960
TTCCAGTGTAAGGGTCGCGGGTCCCCAACATGGCGCCCCCAATATGGCGCCCCCAAT

124020
ATGGCGCCCCAGACATGGCGCCCGGCCCCTCACCTCGCGCTGGGGGCGGCCCTCAGGCCG

124080
GCGGGTACTCGCTCCGGGGCGGGGCTC<u>CAT</u>GGGGGTCGTATGCGGCTGGAGGGTCGCGGA
               N terminus of ICP0

124140
CGGAGGGTCCCTGGGGGTCGCAACGTAGGCGGGGCTTCTGTGGTGATGCGCAGAGGGGGC

124200
GGCCCGAGTCTGCCTGGCTGCTGCGTCTCGCTCCGAGTGCCGAGGTGCAAATGCGACCAG
                   5' end ICP0 mRNA 124260
ACTGTCGGGCCAGGGCTAACTTATACCCCACGCCTTTCCCCTCCCCAAAGGGGCGGCAGT
    TF11D binding site for ICP0

124320
GACGATTCCCCCAATGGCCGCGCGTCCCAGCCGAGGCAGGCCCACCGCGGGGCGGCCCCG
 HSP70 ?

124380
TCCCCGGCGACCAACCCGGCGCCCCAAAGAATATCATTAGCATGCACGGCCCGGCCCCC
             taatgarat ICP0 ?

124440
GATTTGGGGCCCAACCCGGTGTCCCCAAAGAACCCCATTAGCATGCCCTCCCGCCGA

124500
CGCAACAGGGGCTTGGCCTGCGTCGGTGCCCCGGGGCTTCCGCCTTCCCGAAGAAACTC
                taatgarat ICP0 ?

124560
ATTACCATACCCGGAACCCCAGGGGACCAATGCGGGTTCATTGAGCGACCCGCGGGCCAA

FIGURE 15J

124620
TGCGCGAGGGGCCGTGTGTTCCGCCAAAAAAGCAATTAGCATAACCCGGAACCCCAGGGG
                  E2F?

124680
AGTGGTTACGCGCGGCGCGGGAGGCGGGGAATACCGGGGTTGCCCATTAAGGGCCGCGGG

124740
AATTGCCGGAAGCGGGAAGGGCGGCCGGGGCCGCCCATTAATGAGTTTCTAATTACCATA
                                              Vsp1

124800
CCGGGAAGCGGAACAAGGCCTCTTGCAAGTTTTTAATTACCATACCGGGAAGTGGGCGGC
                              3' end γ34.5 ?

124860
CCGGCCCATTGGGCGGTAACTCCCGCCCAATGGGCCGGGCCCCGAAGACTCGGCGGACGC
                                                 HSP70 ?

124920
TGGTTGGCCGGGCCCCGCCGCGCTGGCGGCCGCCGATTGGCCAGTCCCGCCCCCGAGGCG

124980
GCCCGCCCTGTGAGGGCGGGCTGGCTCCAAGCGTATATATGCGCGGCTCCTGCCATCGTC
                                                  ICP4 binding

125040
TCTCCGGAGAGCGGCTTGGTGCGGAGCTCCCGGGAGCTCCGCGGAAGACCCAGGCCGCCT

125100
CGGGTGTAACGTTAGACCGAGTTCGCCGGGCCGGCTCCGCGGGCCAGGGCCCGGGCACGG
                                 homol with 2kb splice branch

125160
GCCTCGGGCCCCAGGCACGGCCCGATGACCGCCTCGGCCTCCGCCACCCGGCGCCGGAAC

125220
CGAGCCCGGTCGGCCCGCTCGCGGGCCCACGAGCCGCGGCGCGCCAGGCGGGCGGCCGAG

125280
GCCCAGACCACCAGGTGGCGCACCCGGACGTGGGGCGAGAAGCGCACCCGCGCGGGGGTC
                                                  Reiteration 6

125340
GCGGGGGTCGCGGGGGTCGCGGGGGTCGCGGGGGTCGCGGGGGGCTCCGGCGCCCCCTCC

125400
CCGCCCGCGCGTCGCAGGCGCAGGCGCGCCAGGTGCTCCGCGGTGACGCGCAGGCGGAGG

FIGURE 15K

```
125460
GCGAGGCGCGGCGGAAGGCGGAAGGGGCGCGAGGGGGGTGGGAGGGGTCAGCCCCGCCC

125520
CCCGGGCCCACGCCGGGCGGTGGGGGCCCGGGGGGCGGGGGGCGGCGGCGGTGGGCCGGG

125580
CCTCTGGCGCCGACTCGGGCGGGGGCTGTCCGGCCAGTCGTCGTCATCGTCGTCGTCGG
                                                   ICP4 binding

125640
ACGCGGACTCGGGAACGTGGAGCCACTGGCGCACCAGCAGCGAACAAGAAGGCGGGGGCC

125700
CACCGGCGGGGGGCGGCGGCGGGCGGCCGCGGGCGCGCTCCTGACCGCGGGTTCCGAGT

125760
TGGGCGTGGAGGTTACCTGGGACTGTGCGGTTGGGACGGCGCCCGTGGGCCCGGGCGGCC

125820
GGGGGCGGCGGGGCCGCGATGGCGGCGGCGGCGGGCCATGGAGACAGAGAGCGTGCCGG

125880
GGTGGTAGAGTTTGACAGGCAAGCATGTGCGTGCAGAGGCGAGTAGTGCTTGCCTGTCTA

125940
ACTCGCTAGTCTCGGCCGCGGGGGGCCCGGGCTGCCCGCCGCCACCGCTTTAAAGGGCCG
                                                Start 'a' sequence 126000
CGCGCGACCCCCGGGGGGTGTGTTTTGGGGGGGGCCCGTTTTCGGCCTCTGGCCGCTCCT
                                                           Reiteration 7

126060
CCCCCGCTCCTCCCCCGCTCCTCCCCCGCTCCTCCCCCGCTCCTCCCCCGCTCCT

126120
CCCCCGCTCCTCCCCCGCTCCTCCCCCGCTCCTCCCCCGCTCCTCCCCCGCTCCT

126180
CCCCCGCTCCTCCCCCGCTCCTCCCCCGCTCCTCCCCCGCTCCTCCCCCGCTCCT

126240
CCCCCGCTCCTCCCCCGCTCCTCCCCCGCTCCCGCGGCCCCGCCCCCACGCCCGCC

126300
GCGCGCGCACGCCGCCCGGACCGCCGCCCGCCTTTTTTGCGCGCGCGCGCCCGCGG
```

FIGURE 15L

```
126360
GGGGCCCGGGCTGCCACAGGTGAAACCAACAGAGCACGGCGCACTCCGCACGTCACACCT

126420
CACGTCATCCACCACACCTGCCCAACAACACAACTCACAGCGACAACTCACCGCGCAACA

126480
ACTCCTGTTCCTCATCCACACGTCACCGCGCACCTCCCGCTCCTCCAGACGTACCCCGGC

126540
GCAACACACCGCTCCTGCTACACACCACCGCCCCCTCCCCAGCCCCAGCCCTCCCCAGCC

126600
CCAGCCCTCCCCGGCCCCAGCCCTCCCCGGCCCCAGCCCTCCCCGGCCCCAGCCCTCCCC

126660
GGCCCCAGCCCTCCCCGGCCCCAGCCCTCCCCGGCCCCAGCCCTCCCCGGCGCGTCCCGC

126720
GCTCCCTCGGGGGGGTTCGGGCATCTCTACCTCAGTGCCGCCAATCTCAGGTCAGAGATC
                                              hormone recpt ½ site 126780
CAAACCCTCCGGGGGCGCCCGCGCACCACCACCGCCCCTCGCCCCTCCCGCCCCTCGCC
                                              Start short repeat seq

126840
CCCTCCCGCCCCTCGCCCCTCCCGCCCCTCGCCCCTCCCGCCCCTCGCCCCTCCCC

126900
CCCTCGCCCCTCCCGCCCCTCGCCCCTCCCGCCCCTCGCCCCTCCCGCCCCTCGCCC

126960
CCTCCCGCCCCTCGCCCCTCCCGCCCCTCGCCCCTCCCGCCCCTCGCCCCTCCCGCC

127020
CCTCGCCCCTCCCGCCCCTCGCCCCTCCCGCCCCTCGCCCCTCCCGCCCCTCGCCCC

127080
CTCCCGCCCCTCGCCCCTCCCGCCCCTCGCCCCTCCCGCCCCTCGCCCCTCCCGCCC

127140
CTCGAATAAACAACGCTACTGCAAAACTTAATCAGGTTGTTGCCGTTTATTGCGTCTTCG
    3' end mLAT ?                               3' end ICP4
```

FIGURE 15M

```
127200
GGTCTCACAAGCGCCCCGCCCCGTCCCGGCCCGTTACAGCACCCCGTCCCCCTCGAACGC

127260
GCCGCCGTCGTCTTCGTCCCAGGCGCCTTCCCAGTCCACAACTTCCCGCCGCGGGGGCGT

127320
GGCCAAGCCCGCCTCCGCCCCCAGCACCTCCACGGCCCCGCCGCCGCCAGCACGGTGCC

127380
GCTGCGGCCCGTGGCCGAGGCCCAGCGAATCCCGGGCGGCGCCGGCGGCAGGGCCCCGG

127440
GCCGTCGTCGTCGCCGCGCAGCACCAGCGGGGGGGCGTCGTCGTCGGGCTCCAGCAGGGC

127500
GCGGGCGCAAAAGTCCCTCCGCGGCCCGCGCCACCGGGCCGGGCCGGCGCGCACCGCCTC

127560
GCGCCCCAGCGCCACGTACACGGGCCGCAGCGGCGCGCCCAGGCCCCAGCGCGCGCAGGC

127620
GGCGTGCGAGTGGGCCTCCTCCTCGCAGAAGTCCGGCGCGCCGGGCGCCATGGCGTCGCT

127680
GGTCCCCGAGGCCGCCGCCCGGCCGTCCAGCGCCGGCAGCACGGCCCGGCGGTACTCGCG

127740
CGGGGACATGGGCACCGGCGTGTCCGGGCCGAAGCGCGTGCGCACGCGGTAGCGCACGTT

127800
GCCGCCGCGGCACAGGCGCAGCGGCGGCGCGTCGGGGTACAGGCGCGCGTGCGCGGCCTC

127860
CACGCGCGCGAAGACCCCGGGCCGAACACGCGGCCCGAGGCCAGCACCGTGCGGCGCAG

127920
GTCCCGCGCCGCCGGCCAGCGCACGGCGCACTGCACGGCGGGCAGCAGCTCGCACGCCAG

127980
GTAGGCGTGCTGCCGCGACACCCCGGGCCCGTCGGCGGGCCAGTCGCAGGCGCGCACGGT

128040
GTTGACCACGATGAGCCGCCGGTCGCCGGCGCTGGCGAGCAGCCCCAGAAACTCCACGGC
```

FIGURE 15N

128100
CCCGGCGAAGGCCAGGTCCCGCGTGGACAGCAGCAGCACGCCCTGTGCGCCCAGCGCCGA

128160
CACGTCGGGGGCGCCGGTCCAATTGCCCGCCCAGGCGGCCGTGTCCGGCCCGCACAGCCG

METHOD AND COMPOSITIONS FOR STABILIZING UNSTABLE GENE TRANSCRIPTS

CROSS-EFERENCE TO RELATED APPLICATIONS

This is a 371 of PCT/US98/07691, which claims the benefit of the priority of U.S. patent application Ser. No. 60/044,664, filed Apr. 18, 1997.

This invention has been supported by grants from the National Institutes of Health, Public Health Service Grant No. NS33768 and training grant AI07324. The US government has certain rights in this invention.

FIELD OF THE INVENTION

The present invention relates generally to methods of stabilizing unstable gene transcripts for use in, e.g., gene therapy, and specifically to the use of the HSV-1 LAT sequences in such methods.

BACKGROUND OF THE INVENTION

*Herpes simplex* virus type 1 (HSV-1) is a neurotropic virus capable of forming latent infections for the lifetime of an individual. Upon stress the viral genome undergoes extensive transcription and replication leading to the production of viral proteins and infectious particles. Contrary to the acute initial infection or subsequent reactivation events, during latency transcription is restricted to a single diploid gene within the long repeat elements of the viral genome. Transcription of this gene generates a family of transcripts known as the latency-associated transcripts (LATs) (see FIG. 1) [Rock, D. L. et al., (1987), *J. Virol.*, 61:3820–3826; Spivack, J. G., and N. W. Fraser, (1987), *J. Virol.*, 61:3841–3847 (Spivack 1987); Stevens, J. G. et al, (1987), *Science*, 235:1056–1059; and Wechsler, S. L. et al, (1988), *J. Virol.*, 62:4051–4058].

An 8.5 kb LAT (referred to as the minor LAT or MLAT based on its abundance) is postulated on the basis of in situ hybridization of infected tissues and the presence of a LAT promoter element mapping to its 5' end and of a polyadenylation signal near its 3' end. It is found in very low amounts in trigeminal ganglia of infected animals [Mitchell, W. J. et al, (1990), *J. Gen. Virol.*, 71:125–132].

The most abundant LAT species is a 2 kb long transcript (referred to as 2.0 kb LAT), which does not appear to be polyadenylated [Devi-Rao, G. B. et al, (1991), *J. Virol.*, 65:2179–2190; Nicosia, M. et al, (1994), 204:717–728 (Nicosia 1994); Spivack 1987; and Wagner 1988] and also lacks a cap at its 5' end which maps to a splice donor sequence GT [Krause, P. R. et al, (1990) *J. Clin. Invest.*, 86(1):225–241; Krause, P. R. et al, (1991) *J. Virol.*, 65:5619–5623; Spivack, J. G. et al, (1991), *J. Virol.*, 65:6800–6810 (Spivack 1991); and Wagner 1988].

The 2.0 kb LAT is considered to be a unique class of genes, known as the λ class [Spivack 1988]. It has been proposed that the 2.0 kb LAT is a stable intron derived from the larger 8.5 kb MnLAT RNA. Consistent with this, Farrell, M. J. et al, 1991, *Proc. Natl. Acad. Sci. USA.*, 88:790–794 have shown that the 2.0 kb LAT RNA could be spliced out of a β-galactosidase transcript containing the LAT sequences in transient transfections. additionally Wu, T. T. et al, 1996, *J. Virol.*, 70:5962–5967 have recently shown that the majority of the 2.0 kb LAT transcript is in a non-linear structure most likely a lariat. However, the spliced exons of the putative primary transcript MLAT have never been detected.

Removal of a short intron in the 2.0 kb LAT leads to the production of a small variant of 1.5 kb in size. Both transcripts are routinely detectable by Northern hybridization [Rock et al, Spivack 1987, Stevens et al and Wechsler et al, cited above]. These RNAs are partially colinear and are thought to evolve by differential splicing. The 1.5 kb LAT is only observed during latency in neurons, whereas the 2.0 kb LAT is detectable in productive infections in tissue culture and animals with the kinetics of a late gene, as well as during latency [Spivack 1987; Spivack, J. G., and N. W. Fraser, (1988), *J. Virol.*, 62:3281–3287 (Spivack 1988); Wagner, E. K. et al, (1988), *J. Virol.*, 62:1194–1202 (Wagner 1988)].

Two promoters involved in the generation of the 2.0 kb LAT RNA have been identified. They are known as the Latency Active Promoter 1 (LAP 1) [Batchelor, A. H. and P. O'Hare, 1990, *J. Virol.*, 64:3269–3279; Dobson, A. T. et al, 1989, *J. Virol.*, 63:3844–3851; Zwaagstra, J. et al, 1991, *Virol.*, 182:287–297; Zwaagstra et al, 1989, *J. Gen. Virol.*, 70:2163–2169; Zwaagstra et al, 1990, *J. Virol.*, 64:5019–5028] and the Latency Active Promoter 2 (LAP2) [Goins, W. F. et al, 1994. *J. Virol.*, 68:2239–2252]. The LAP1 promoter, mapping to the 5' end of mLAT, is the promoter of this putative transcript. Speculation of a second promoter for the 2.0 kb LAT was prompted by the observation that deletion mutants of the LAT1 promoter still produce 2.0 kb LAT RNA during productive infections in tissue culture and animals, but not during latency [Nicosia, M. et al, 1993, *J. Virol.*, 67:7276–7283]. Subsequently, a second promoter element, LAP2, was mapped at or near the 5' end of the 2.0 kb LAT. This promoter, which lacks a TATA box but has a putative initiator element, may drive transcription of the 2.0 kb LAT RNA during productive infections [Chen, X. et al, 1995, *J. Virol.*, 69:7899–7909; Nicosia 1993]. Studies with virus mutants have revealed that LAP1 operates primarily in latency and LAP2 is mainly active in productive infections [Nicosia, 1993; Chen, 1995 and Dobson 1989]. Since the LAP2 promoter abuts the 5' ends the 2.0 kb LAT, it has been proposed that the 2.0 kb LAT and the 8.5 kb LAT may be separate transcripts generated by transcription from these different promoters [Goins, 1984].

The functions of the LATs have not been clearly determined. Some LAT deletion mutants reactivate with reduced kinetics from latency [Steiner, I. et al, 1989, *EMBO J.*, 8:505–511] and appear to establish latency with reduced efficiency [Sawtell, N. M., and R. L. Thompson, 1992, *J. Virol.* 66:2157–2169]. However, these phenotypes may not map to the LATs but to other newly identified transcripts that overlap the LAT region [Bohenzky, R. A. et al, 1995, *J. Virol.*, 69:2889–2897; Lagunoff, M. et al, 1996, *J. Virol.* 70:1810–1817; Lagunoff, M., and B. Roizman, 1994, *J. Virol.*, 68:6021–6028; Lagunoff, M., and B. Roizman, 1995, *J. Virol.*, 69:3615–3623; Singh, J., and E. K. Wagner, 1993, *Virol.*, 196: 220–231; and Yeh, L., and P. A. Schaffer, 1993, *J. Virol.*, 67:7373–82]. During latency, the LATs are nuclear localized; however, in productive infections of tissue culture cells and SCID mice brainstems, the 2.0 kb LAT is present in the cytoplasm. The majority of cytoplasmic 2.0 kb LAT RNA is not associated with polysomes in productively infected tissue culture cells [Nicosia, 1994], suggesting that this transcript is not translated under these conditions.

During natural RNA processing, introns are removed from messenger RNA during a succession of molecular events involving specialized small nuclear ribonucleoproteins (snRNP). Proper recognition of splicing signals such as splice donors (SDs), splice acceptors (SAs) and branchpoint sequences by snRNPs are essential steps in this process. Consensus branch sites are efficiently used whereas non conserved sites are poorly recognized and often lead to suboptimal alternative splicing or exon skipping. Surrounding regions, secondary structures and polypyrimidine tract are also known to influence selection of a branch point. Introns are usually rapidly degraded by a multistep process involving exonucleases, endonucleases, and specialized debranching enzymes. Some stable introns have been described from cellular, viral or bacterial (e.g., thermophilic) origin; however a general mechanism underlying this resistance to degradation is not fully understood.

Different strategies have evolved to confer stability to RNA, particularly mRNA. Known examples include secondary structures serving as protein docking sites, long polyadenylated tails or possibly sequestration in nuclease-free environment. Some resistant introns, including 2.0 kb LAT, are also known to be more resistant to debranching enzymes.

There is a need in the art for methods useful in stabilizing unstable gene transcripts.

SUMMARY OF THE INVENTION

In one aspect, the invention provides a polynucleotide molecule comprising: (a) a polynucleotide sequence encoding a gene product; (b) a 5' sequence of an intron comprising the splice donor and splice acceptor thereof; (c) a 3' sequence of an intron comprising a hairpin structure adjacent to the branchpoint of the intron. In this molecule, the sequence (a) is flanked by the sequences (b) and (c), and said polynucleotide molecule stably expresses the gene product in culture. The molecule may further comprise an internal ribosome entry site, and may be either RNA or DNA.

In one embodiment, the intron is the 2.0 kb LAT of a herpes virus. In sequence (c), the hairpin may be located either 5' or 3' to the branchpoint. In the 5' sequence (b) the sequence may span from about 2 to about 20 nucleotides 5' to the 5' nucleotide of the 2.0 kb LAT through about 2 to about 20 nucleotides 3' to that 5' nucleotide. The 3' sequence (c) comprises a polynucleotide sequence spanning from about 100 to about 300 nucleotides 5' to the 3' nucleotide of the 2.0 kb LAT through about 2 to about 20 nucleotides 3' to the 3' nucleotide.

In another aspect, the invention provides an expression vector which contains the polynucleotide molecule described above, wherein the sequence (a) is under the control of regulatory sequences which direct stable expression of the gene product in a host cell.

In yet a further aspect, the invention provides a host cell transfected with the above-described vector.

In still a further aspect, the invention provides a method for stably expressing an unstable gene transcript to permit enhanced expression of the gene product. The method includes the steps of culturing a host cell transfected with the above-described expression vector and isolating the product of the gene from the cytoplasm of the host cell or from the culture.

In yet another aspect, the invention provides a method for stably expressing a gene having an unstable mRNA in a cell comprising infecting a cell with a stable polynucleotide molecule, as described above.

Other aspects and advantages of the present invention are described further in the following detailed description of the preferred embodiments thereof.

BRIEF DESCRIPTION OF THE DRAWINGS

FIG. 1A is a linear map of the HSV-1 genome. The 152 kb double-stranded DNA genome with its unique long region ($U_L$) flanked by the terminal repeat long ($TR_L$) and the internal repeat long ($IR_L$) and its unique short region ($U_S$) bounded by the terminal repeat short ($TR_S$) and the internal repeat short ($IR_S$).

FIG. 1B illustrates the LAT region of the HSV-1 genome enlarged to show different transcripts that map to this region (LATs, L/STs, ICPO, g34.5, ICP4, UL54, UL55, and UL56). The relevant restriction enzyme sites are shown. The putative 8.5 kb primary transcript mLAT and the postulated spliced exons of mLAT (referred to as LATex) are represented by dotted arrows.

FIG. 1C illustrates the LAT minigene expression vector, pLAT described in Example 2. The CMV IE promoter and the postulated LAP2 promoter region are represented by bold lines. Transcripts expected if the 2.0 kb LAT RNA is an intron are depicted. The DNA fragments used as probes are shown: A, 0.4 kb StyI-StyI; B, 0.9 kb BstEII-BstEH; C, 1.0 kb BstEII-BstEII. Positions of the oligonucleotide Tail and polymerase chain reaction (PCR) primers specific for Exon 1 and Exon 2 of mLAT are indicated.

FIG. 5 illustrates the sequence homology between the 3' ends of the HSV-1 and HSV-2 LAT introns. The sequences of the 3' ends of the HSV-1 2.0 kb LAT intron and the HSV-2 2.3 kb LAT intron are shown with the consensus sequences for the mammalian branchpoint, polypyrimidine tract, and SA site (AG). Identity is indicated by lines between the sequences. The potential HSV-1 2.0 kb LATin branchpoint sequences identified by RT-PCR are underlined in the HSV-1 and HSV-2 LAT intron sequences. The HSV-1 LATin branched nucleotide at position 121344 is shown in bold. Spaces were introduced into the HSV-2 sequence to preserve identity. The n, m, and x indicate approximately 100, 12 to 20, and 0 to several nucleotides, respectively.

FIG. 7A is a schematic representation of the LAT locus of HSV-1. Genomic BamHI restriction fragments B, SP and Y are represented as well as transcripts arising from this region (arrows). Nucleotides are numbered according to McGeoch et al, 1988, *J. Gen. Virol.*, 69:1531–1574, which is incorporated herein by reference.

FIG. 7B is an enlarged schematic representation of the wildtype (wt) 2.8 kb PstI-MluI fragment containing the 2 kb LAT cloned in pcDNA3 (Invitrogen). Arrows represent the SD and SA sites at the beginning and end of the wild type 2.0 kb LAT. The 168 bp deletion in construct pΔHpa is also shown.

FIG. 7C is a schematic representation of λ phage DNA sequences (shaded boxes) with arrows indicating their orientations in both pHλ+ and pHλ− constructs. The different probes used in Northern blots are shown as gray lines. The upstream StyI-StyI probe is specific for exon 1. Probe BspMI-SphI covers the 5' end of the 2 kb LAT upstream of the λ insert. Probe BstEII-BstEII covers most of the 3' end of the 2 kb LAT, the missing HpaI fragment and extends 210 nucleotides upstream of the 5' HpaI site.

FIG. 9B is a detailed map of the last 95 nucleotides of the 2.0 kb LAT with smaller deletions (dashes) or substitutions (gray boxes). pY+ and − are identified by the insertion they carry in the BamHI site of pBam. The black dot indicates the branch nucleotide of LAT as described herein and the white circle shows the hypothetical branch point proposed by Wu et al, cited above. Nucleotides are numbered according to McGeoch et al, cited above.

FIG. 12A is a model of the 3' end of the wt LAT intron. The wild type sequence and putative structure are shown (wt) and compared to mutated LATs of FIGS. 12B through 12J. Positions and numbers of deleted nucleotides are indicated. Underlined bases on the wt model are changed between HSV-1 and HSV-2 LAT McGeoch et al, 1988, *J. Gen. Virol.* 69:1531–1574. The branchpoint is indicated by an arrow. Full arrows indicate branch nucleotides in wt or consensus sites. FIG. 12B is a model of the 3' end of the LAT intron for pBam. Symbols are as described in FIG. 12A; additionally, open arrows show alternative multiple branch points used by the mutant. For clarity, the putative structure of the mutant LAT is based on the wt LAT model, without taking newly generated structures into account (especially for mutants pΔ#3, pΔ#4 and pΔ#5 in which the overall sequence in this region is altered).

FIG. 12C is a model of the 3' end of the LAT intron for pCons. Symbols are as described in FIGS. 12A and 12B.

FIG. 12D is a model of the 3' end of the LAT intron for pΔ#3. Symbols are as described in FIGS. 12A and 12B; additionally, lower case letters indicated upstream sequences brought into this region by the larger deletions of pΔ#3. A branchpoint was not determined for pΔ#3.

FIG. 12E is a model of the 3' end of the LAT intron for pΔA. Symbols are as described in FIGS. 12A through 12C.

FIG. 12F is a model of the 3' end of the LAT intron for pΔG. Symbols are as described in FIGS. 12A through 12C.

FIG. 12G is a model of the 3' end of the LAT intron for pΔ#4. Symbols are as described in FIGS. 12A through 12C.

FIG. 12H is a model of the 3' end of the LAT intron for pY−. Symbols are as described in FIGS. 12A through 12C.

FIG. 12I is a model of the 3' end of the LAT intron for pY+. Symbols are as described in FIGS. 12A through 12C.

FIG. 12J is a model of the 3' end of the LAT intron for pΔ#5. Symbols are as described in FIGS. 12A through 12C.

FIGS. 15A to 15N represent the sequence of the HSV-1, strain 17, 2.0 kb LAT of McGeoch et al, 1988, *J. Gen. Virol.* 69:1531–1574.

DETAILED DESCRIPTION OF THE INVENTION

Figure 2:
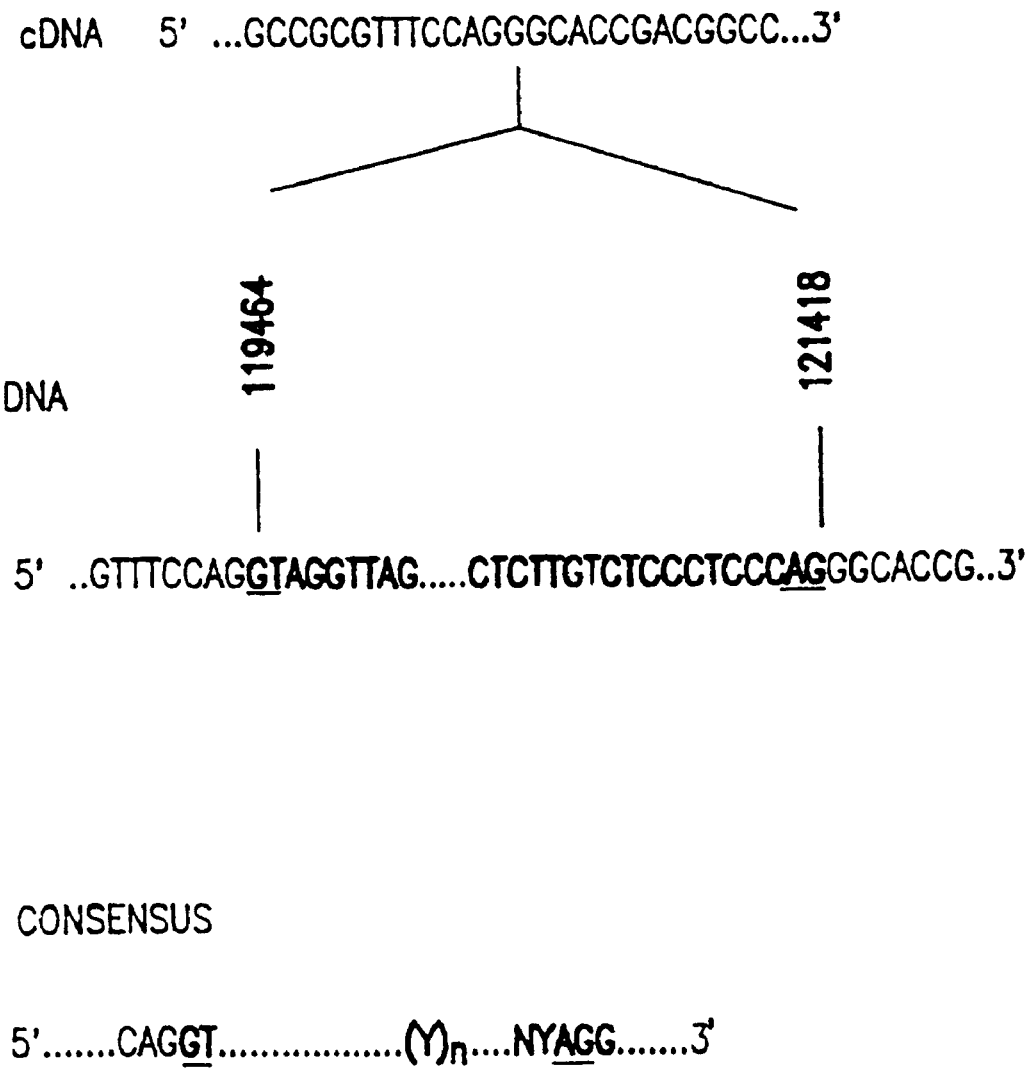
FIG. 2 illustrates the LATin SD and SA sites as described in Example 4. Intron sequences are in bold and the SD and SA sites are underlined. Consensus mammalian sequences for splicing are also shown The sequence at the splice junction of the LATex DNA is shown with the corresponding sequences of the mLAT DNA.

The present invention provides methods and compositions useful for stabilizing a gene transcript to permit enhanced recombinant expression of the gene product. The methods and compositions are useful for the production of vectors and gene products useful in research as reagents thereof, as markers of gene production, and as diagnostic and therapeutic compositions. The methods particularly allow an unstable gene transcript to be stabilized in vitro and in vivo, and thus permit enhanced quantities of the gene product to be produced.

I. Compositions of the Invention

This invention provides a non-naturally occurring, stable polynucleotide molecule which is formed by the association of a polynucleotide sequence encoding a selected gene flanked by regions of a polynucleotide sequence of a stable intron which has a hairpin structure substantially adjacent to a branchpoint. By "substantially adjacent to the branchpoint" is meant that the hairpin may be located 5' to said branchpoint or 3' to the branchpoint. The hairpin is preferably within a few nucleotides (i.e., <10 nucleotides) of the branchpoint.

Specifically, a polynucleotide molecule according to this invention contains:

(a) a polynucleotide sequence encoding a gene product;
(b) a 5' sequence of an intron including the splice donor and splice acceptor of the intron;
(c) a 3' sequence of an intron, preferably the same intron as used in (b), which contains a hairpin structure adjacent to the branchpoint of said intron. In this molecule, the sequence (a) is flanked by the sequences (b) and (c). This polynucleotide molecule stably expresses the gene product in culture. This polynucleotide molecule can be RNA, DNA or cDNA.

Preferably the molecule also stains an internal ribosome entry site (IRES) inserted between the 5' and 3' sequences of the intron. The internal ribosome entry site sequence is located 5' to the open reading frame encoding a selected gene product. The IRES permits the ribosome to bind 5' to the open reading frame and initiate translation of the following open reading frame. Desirable IRES include those sequences known to have this function, which are normally derived from viral sequences. An exemplary viral IRES is derived from the EMC virus. A mammalian IRES called BiP has been described [see, e.g., D. G. Macejak and P. Sarnow, 1991, *Enzyme*, 44:310–319; D. G. Macejak and P. Sarnow, 1991, *J. Cell. Biochem.*, Suppl. 15, part D: 199, and references cited therein] and may also be used for this purpose. Other viral, insect, yeast, or mammalian IRES may also be used in constructs of this invention. The selection of the IRES is not a limitation of this invention.

One particularly useful intron for a composition according to this invention is the 2.0 kb LAT of *Herpes Simplex* Virus, type I (HSV-1), strain 17. The sequence of this LAT is reported in McGeoch et al, 1988, *J. Gen. Virol.*, 69:1531–1574. The sequence of the 2.0 kb LAT of HSV-1 strain F is reported in Spivak et al, 1991, *J. Virol.*, 65:6800–6810. Both publications are incorporated by reference for the disclosure of these 2.0 kb LAT sequences. Other introns characterized by a hairpin structure substantially adjacent to a branchpoint, are anticipated to be similarly useful in this invention.

Thus, a desirable composition according to this invention is formed by a polynucleotide sequence encoding a selected gene in operative association with sequences of the known HSV-1 2.0 kb LAT sequence. In one embodiment, such a stable molecule comprises, preferably in 5'–3' order, (a) a polynucleotide sequence comprising a 5' region of the 2.0 kb LAT, including the splice donor and splice acceptor thereof,
(b) a polynucleotide sequence comprising an internal ribosome entry sequence (IRES);
(c) a polynucleotide sequence comprising an open reading frame encoding a selected gene product (or an mRNA transcript thereof); and
(d) a polynucleotide sequence comprising a 3' region of the 2.0 kb LAT which has a hairpin structure adjacent to its branchpoint.

Preferably, the 5' sequence (a) described immediately above is a polynucleotide sequence spanning from about 2 to about 20 nucleotides 5' to the 5' nucleotide of the intron through about 2 to about 20 nucleotides 3' to that 5' nucleotide of the intron. Thus, this 5' sequence, which contains the 5' splice donor/splice acceptor site of the intron, can range from about 40 nucleotides in length to about 5 nucleotides in length. As one example, the 5' nucleotide of the 2.0 kb LAT of HSV-1, strain 17, is depicted in FIG. 2 as nucleotide position 119464. Desirably, the 5' sequence useful in this invention may comprise a polynucleotide sequence spanning about 20 nucleotides 5' to position 119464 (the 5' nucleotide of the 2.0 kb LAT) to about 20 nucleotides 3' to that same nucleotide. Still more preferably, the 5' sequence comprises a polynucleotide sequence spanning about 20 nucleotides 5' to the 5' nucleotide of the 2.0 kb LAT to about 10 nucleotides 3' to the 5' nucleotide. Another desirable 5' sequence spans about 20 nucleotides 5' to the 5' nucleotide of LAT to about 2 nucleotides 3' thereto. Still other sequences within the largest range may be selected provided that the 5' sequence includes the splice donor/splice acceptor sequence which naturally occurs 5' to the first nucleotide of the 2.0 kb LAT. This 5' sequence is obtained from the native LAT sequence by isolation or constructed by synthesis according to the published sequence. Corresponding sequences may be obtained from other introns by conventional methods which follow the teachings herein.

The 3' sequence of the intron includes the hairpin adjacent to the branchpoint. This sequence also includes a splice acceptor site. At a minimum, this sequence is about 80 nucleotides in length. However, this sequence may comprise a polynucleotide sequence spanning about 100 to about 300 nucleotides 5' to the 3' nucleotide of the intron through to about 2 to about 20 nucleotides 3' to the 3' nucleotide of the intron. One desirable 3' intron sequence (d) comprises a polynucleotide sequence spanning from about 300 nucleotides 5' to the 3' nucleotide of an intron through about 2 nucleotide 3' to that 3' nucleotide. Another useful 3' sequence (d) comprises a polynucleotide sequence spanning from about 200 nucleotides 5' to the 3' nucleotide of an intron through about 20 nucleotides 3' to that 3' nucleotide. Yet a further desirable 3' sequence (d) comprises a polynucleotide sequence spanning from about 150 nucleotides 5' to the 3' nucleotide of the intron through about 2 to about 20 nucleotides 3' to the 3' nucleotide. Using the 2.0 kb LAT of HSV-1, strain 17, as an example of a suitable intron, the 3' nucleotide of this intron is depicted in FIG. 2 as nucleotide position 121418. Thus, a desirable 3' sequence for the composition of this invention comprises a polynucleotide sequence spanning about 200 nucleotides 5' to the 3' nucleotide of the 2.0 kb LAT to about 20 nucleotides occurring after the 3' nucleotide. The 3' sequence includes the splice acceptor sequence which naturally occurs 3' to the last nucleotide of the 2.0 kb LAT.

Still other sequences within the largest range may be selected according to the formula provided above. This 3' sequence (d) is obtained from the native LAT sequence by isolation or is constructed by synthesis according to the published sequence. Corresponding sequences may be obtained from other introns characterized by a hairpin adjacent to the branchpoint by conventional methods which follow the teachings herein and use other published intron sequences.

While not wishing to be bound by theory, the inventors speculate that the structure of the hairpin in the 3' sequence of the introns used in the molecules of this invention may protect the structural integrity of the branchpoint. It is also possible, as described below, that the presence of a branchpoint which is a guanosine or an adenosine also enhances the stability of this molecule. It is anticipated that any intron having sequences characteristic of the 2.0 kb LAT hairpin structure may be useful in the compositions of this invention. Such intron sequences may be further stabilized by the substitution of a guanosine or adenosine at the branchpoint and further manipulated for use in expressing unstable transcripts by resort to the teachings herein. However, while the branchpoint may enhance the results described herein, the identity of the branchpoint is not considered to be a limitation of this invention.

The polynucleotide sequence which comprises an open reading frame encoding a selected gene product (or an mRNA transcript thereof) for purposes of this invention can be the mRNA for any gene desired for expression in a host cell. However, the compositions and methods of this invention are designed to have the most effect when the mRNA is "unstable", i.e., the transcript of the gene is short-lived in a cell and results in poor expression. There are a variety of unstable gene transcripts known to the art, and any of them may be chosen as the selected gene. As examples only, among such "unstable" genes are proto oncogenes, such as c-myc and c-fos, and growth factor genes, such as the genes which encode GM-CSF, some interleukins and many others. Again the selection of the mRNA or unstable gene is not a limitation of this invention.

Still another component of the stable polynucleotide molecule of this invention is a conventional promoter sequence, which can be inserted 5' to the 5' intron sequence which is sequence (a) in the formula immediately above. This promoter is operably linked within the molecule to direct expression of the selected gene in a host cell.

The promoter is thus 5' to the above-mentioned splice donor site. The selection of desirable promoters is well within the skill of the art depending on the host cell in which the gene product is to be expressed. An exemplary promoter is the cytomegalovirus (CMV) immediate early (IE) gene promoter. However, selection of a suitable promoter from among known promoters is well within the skill of the art.

The polynucleotide molecule is synthetically or recombinantly designed so that a selected gene, particularly a gene noted for its instability in vitro or in vivo, is placed in association with the truncated LAT intron.

The sequences or regions of the polynucleotide molecule of this invention, i.e., sequences of the HSV-1 2.0 kb LAT, the ORF, the IRES, etc., may be obtained by conventional genetic engineering methods. For example, one could delete the middle portion between the desired 5' and 3' regions of the LAT with restriction endonuclease enzymes (e.g., Xcm1; see FIG. 13), or simply obtain the 5' and 3' regions by conventional synthesis. Promoters, IRES, and the selected gene may all be selected and combined in a polynucleotide molecule by resort to conventional techniques. See, e.g., such conventional methods as described in texts such as Sambrook et al, "Molecular Cloning. A Laboratory Manual.", 2d edit., Cold Spring Harbor Laboratory, New York (1989) and others.

Once designed, the resulting polynucleotide structure forms a hairpin structure, characteristic of the intron, adjacent to the branchpoint.

For expression of the unstable gene an expression vector may be designed by conventional recombinant techniques to comprise the polynucleotide molecule described above. Also present in the vector 5' to the splice donor sequence are conventionally used DNA regulatory sequences, such as promoters, and regulators. Polyadenylation signals may optionally be included 3' to the splice acceptor (SA) site. Some of these sequences may operate to direct expression of the gene product and LAT in a host cell.

Conventional vector sequences or plasmids may be employed and manipulated to contain the polynucleotide molecule of this invention. "Plasmids" are genetic elements that are stably inherited without being a part of the chromosome of their host cell. They may be comprised of DNA or RNA and may be linear or circular. Plasmids code for molecules that ensure their replication and stable inheritance during cell replication and may encode products of considerable medical, agricultural and environmental importance. Plasmids are widely used in molecular biology as vectors used to clone and express recombinant genes. A number of plasmid vectors useful in this invention are either commercially available, publicly available, or can be constructed from available materials by routine application of well known, published procedures.

Moreover, those of skill readily may construct any number of other vectors suitable for use in the invention, including viral vectors, such as recombinant adenoviruses, retroviruses, vaccinia vectors and the like. The properties, construction and use of such plasmids, as well as other vectors, in the present invention will be readily apparent to those of skill from the present disclosure. Selection of these and other common plasmid/vectors and the regulatory elements useful in the invention are conventional [see, e.g., Sambrook et al, cited above, and references cited therein] and many such sequences are available from commercial and industrial sources as well as from Genbank.

Figure 13:
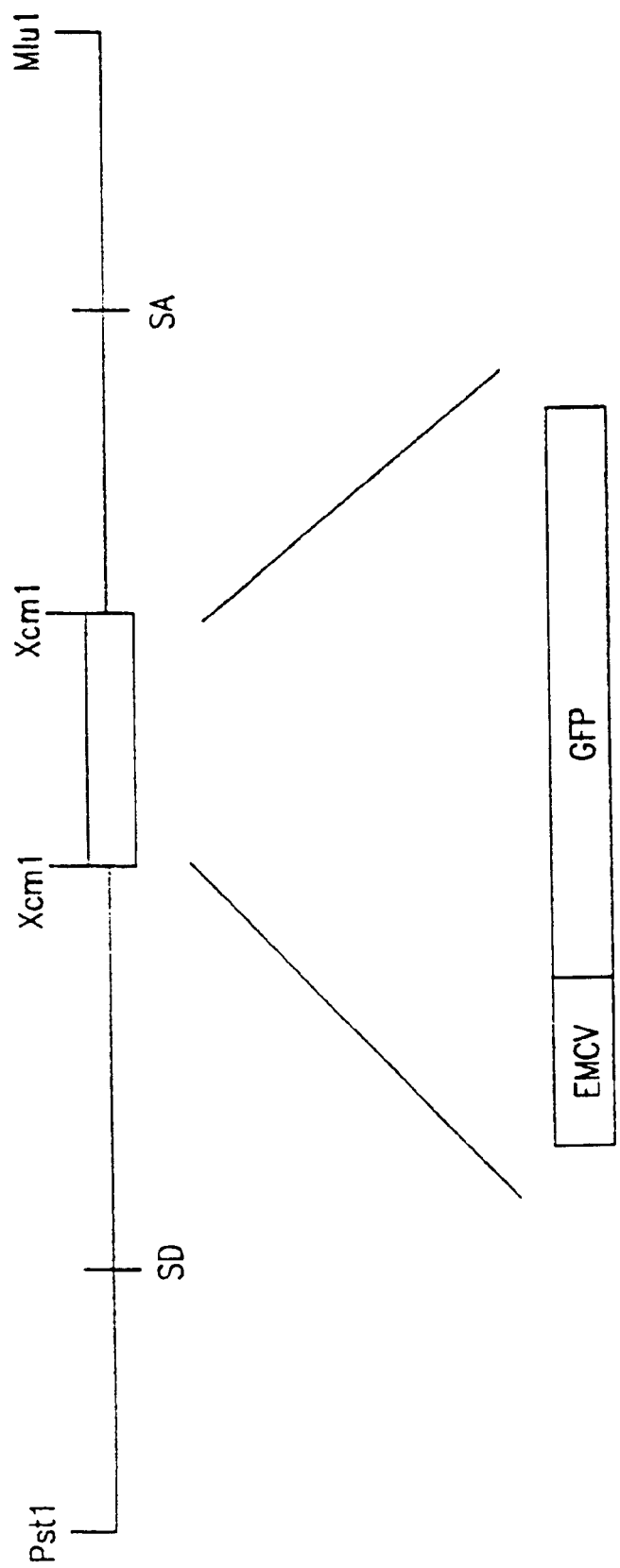
FIG. 13 is a schematic model of stabilization of protein-encoding RNA by construction of a stable intron according to this invention. Encephalomyocarditis virus (EMCV) represents the EMC virus ribosome entry sequence. Green fluorescent protein (GFP) represents an exemplary transcript encoding green fluorescent protein. Restriction enzyme abbreviations are conventional. SD means splice donor; SA means splice acceptor. The plasmid containing the EMCV and GFP cDNA is enlarged in the lower portion of the figure.

Such vectors are designed to contain a polynucleotide molecule of this invention. An example of a plasmid vector containing an EMC IRES and the gene encoding green fluorescent protein is depicted in FIG. 13 and described in Example 17.

The resulting vector may be transfected into a host cell for in vitro or in vivo expression of the selected gene. By "host cell" is meant any cell which can be used to express a gene. Generally, preferred host cells for in vitro expression may be mammalian cells, bacterial cells, yeast cells, insect cells and the like. Where the use involves gene therapy, the "host cell" may be a mammalian cell, most preferably an animal or human cell.

II. Methods of this Invention

Thus, a method of the invention for in vitro expression of the unstable or selected gene involves culturing a host cell transfected with a polynucleotide sequence as described above, or a vector containing such a polynucleotide sequence, with the molecule or vector designed such that the expression of the gene product is under the control of regulatory sequences directing the expression of the gene product in a host cell. Thereafter the product of the gene is isolated from the cytoplasm of said host cell or from the culture medium, if the gene product is secreted from the host cell.

Use of this method permits enhanced production in vitro of the gene product for use as a component of diagnostic, therapeutic or research compositions, depending on the identity of the gene product. Methods for transfecting a cell in vitro are conventional, as are methods for culturing the transfected cell thereby enabling expression of the gene product and its export into the cytoplasm of the cell. Isolating the gene product from the cytoplasm may also be accomplished by known techniques.

The compositions of the invention are also useful as markers for determining whether a gene of interest is being transcribed. For example, a LAT intron could be inserted into the desired transcript according to the invention, to permit its detection. This method of using the compositions of the invention as markers is useful in diagnostic applications, as well as in drug screening, and is particularly well suited for identification of genes transcribed only in a selected stage of the cell cycle.

Still another method of use of the above compositions of the present invention involves stably expressing the selected gene having an unstable mRNA in vivo for, e.g., gene therapy. To accomplish this aspect of the invention, a selected vector incorporating the polynucleotide molecules is prepared by known techniques. Preferred vectors for in vivo use are viral vectors, such as recombinant adenoviruses, poxviruses, etc.

The above-described recombinant vectors are administered to mammals, e.g., humans, in a conventional manner for gene therapy and serve as an alternative or supplemental gene therapy for the disorder to which the selected gene is directed. For example, a recombinant vector of this invention may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The recombinant vectors, such as viral vectors, are administered in sufficient amounts to transfect the desired target cells, e.g., muscle, liver, epithelial, etc. and provide sufficient levels of transfer and expression of the selected gene to provide a therapeutic benefit without undue adverse or with medically acceptable physiological effects which can be determined by those skilled in the medical arts. Conventional and pharmaceutically acceptable routes of administration include direct delivery to the muscle or other selected cell, intranasal, intravenous, intramuscular, subcutaneous, intradermal, oral and other parental routes of administration. Routes of administration may be combined, if desired.

Dosages of recombinant vector will depend primarily on factors such as the condition being treated, the age, weight and health of the patient, and may thus vary among patients. For example, a therapeutically effective human dose of a recombinant adenovirus is generally in the range of from about 20 to about 100 ml of saline solution containing concentrations of from about $1 \times 10^9$ to $1 \times 10^{11}$ pfu/ml virus. A preferred human dose is estimated to be about 50 ml saline solution at $2 \times 10^{10}$ pfu/ml. The dose will be adjusted to balance the therapeutic benefit against any side effects. The levels of expression of the gene can be monitored to determine the frequency of administration.

As discussed in Examples 1–7 below, a polynucleotide molecule containing sequences of the HSV-1 latency-associated transcript (LAT) gene was used to analyze its transcripts in transient transfection assays and permitted selection of the 2.0 kb LAT as a desirable intron for use in the present invention. Briefly summarized, a 2.8 kb fragment of the approximately 8.5 kb LAT gene encompassing the 2.0 kb LAT was cloned into a eukaryotic expression vector downstream of the CMV IE gene promoter. Northern hybridization of RNA isolated from transfected COS-1 cells identified three LAT specific transcripts, 3.4 kb, 2.0 kb, and 1.4 kb in size. Mapping of these transcripts by Northern hybridization indicated that the 1.4 kb and 2.0 kb RNAs are nonoverlapping, while the 3.4 kb RNA overlaps both smaller RNAs. RT-PCR and partial sequencing of the 1.4 kb RNA revealed that this RNA is the spliced exons (LATex) of the 3.4 kb primary transcript. The 2.0 kb LAT appeared as an intron accumulating after splicing of the MnLAT pre-mRNA. The SD and SA sites for the 2.0 kb LAT identified in transfected and HSV-1 infected cells are identical.

The unusual stability of the 2.0 kb LATin led the inventors to postulate that the location of the hairpin adjacent the branchsite of this intron is responsible for stability. Using a novel RT-PCR technique, the branchpoint of the 2.0 kb LATin, expressed in both transfected and infected cells, was identified as a guanosine. This is the first known example of an intron utilizing this nucleotide as a branchpoint in vivo. This branchsite does not bear homology to consensus mammalian branchsite sequences. In transfected cells, the 2.0 kb LAT intron localizes to the cytoplasm, demonstrating that LAT localization is not dependant on viral gene expression.

These data provide evidence that the 2.0 kb LAT RNA is an intron spliced from the MLAT pre-mRNA with a unique or unusual branchpoint. These data imply that the stability of the 2.0 kb LAT intron, while it is likely due to the location of the hairpin, may be enhanced by a unique branchpoint. The HSV-1 2.0 kb LATin is the only example now identified of a naturally occurring intron localizing to the cytoplasm in vivo.

As discussed in Examples 8–16 below, the structural requirements for the production of a stable 2.0 kb LAT were observed. Based on observations of a HSV-1 LAT mutant producing a truncated LAT intron and a panel of mutant LAT constructs, the region at the 3' end of the 2.0 kb LAT was identified as important for stability. The secondary structure in the tail of the 2.0 kb LAT lariat, i.e., the hairpin, is likely responsible for non conventional branch point selection, and influences splicing efficiency and stability of the intron. The unusually stable 2.0 kb LAT is an intron postulated to influence reactivation of HSV-1 from latency.

The analysis of a LAT mutant virus (TB1) revealed an aberrant splicing pattern and production of a stable small 0.95 kb LAT intron. A panel of deletion constructs expressing truncated LAT in transient transfected cells mapped a region influencing stability to the 3' end of the intron. This region encompasses a stable stem-loop structure immediately upstream of the splice consensus polypyrimidine tract. This hairpin has been mutated in different constructs using deletions, substitutions or insertions. This hairpin structure is essential for efficient splicing, and likely directs the selection of a nonconsensus branch point. Destabilization of this structure correlates with abnormal branching and production of an unstable 2.0 kb LAT.

The presence of a stable LAT, though truncated, from TB1 or the related construct indicates that the 3' half of the 2.0 kb LAT by itself contains the necessary elements to confer stability to the intron in infected cells. Since it is generated from a SD in the lambda region, the 5' end of the TB1 0.95 kb intron is different from the wt 2.0 kb LAT with the exception of the first three bases (GTA) involved in the consensus SD sequence. This indicated that a long 5' sequence involved in branching of the lariat is likely not crucial for stability in infected cells.

The panel of deletion mutants used in Examples 8–16, narrowed the region conferring stability to the last 100 bp of the intron including the branchpoint. This domain extends into the stem of a hairpin joining the polypyrimidine tract. This RNA stem-loop structure plays a major role in both stability and splicing of the 2.0 kb LAT. The results of the experiments reported in the examples suggest a strong correlation between the overall stability of the HSV-1 2.0 kb LAT and the stability of the stem of this hairpin. This is possibly mediated, at least in part, through the ability of the stem-loop to direct selection of a branch point.

These results indicate a close relationship between splicing of 2.0 kb LAT and stability of the resulting intron. Stability appears to be achieved by the RNA secondary structure, i.e., the hairpin. Stability may in part be due to a branch site of guanosine or adenosine. A strict conservation of this structure is required to direct suboptimal branch site recognition at the origin of HSV-1 2.0 kb LAT stability.

These examples thus provide the support for the present invention which employs the HSV-1 5' truncated LAT sequence to stabilize the expression of gene products having unstable gene transcripts. See Example 17, which illustrates the expression of the gene product, green fluorescent protein, using the methods and compositions of this invention.

The following examples illustrate certain aspects of the invention and do not limit the scope of the invention, which is defined by the claims below.

EXAMPLE 1

Primers and Probes

Figure 3:
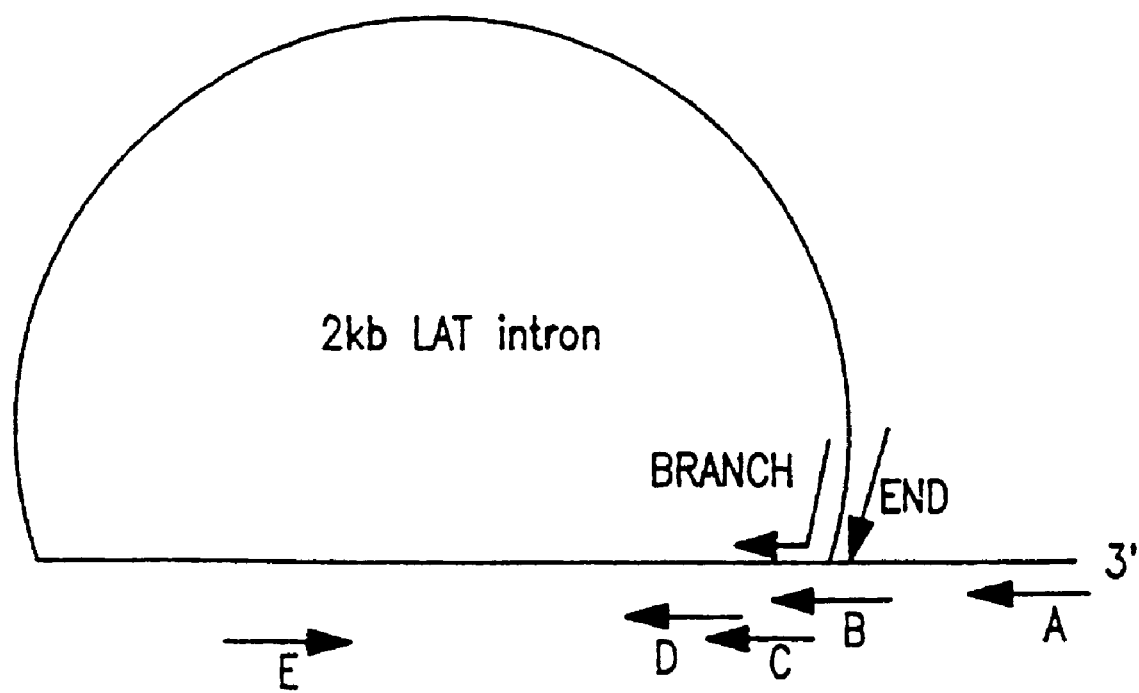
FIG. 3 is a schematic diagram of the 2.0 kb LAT intron in a lariat configuration with the primers used for cDNA synthesis and PCR amplification of the branchpoint sequence. Sequences of the primers and their location in the HSV-1 genome are presented in Table 1.

Table 1 lists the primers and probes used and referenced in the following examples. The sequence and location of the primers are based on published sequences [McGoech, 1988, cited above]. Primers A through E, Branch, End and Branch G in the table are as indicated in FIG. 3 and are HSV-specific oligonucleotides for intron branchpoint mapping.

TABLE 1

| Probe/Primer | Sequence | Location | SEQ ID NO |
|---|---|---|---|
| A | CTGGGGAGGGAGACAAGAGGAAA | 121418–121397 | 2 |
| B | CGAGGAAGTGTGCCCGGAAGAC | 121357–121336 | 3 |
| C | AGACGCGCCACGCGGAAGACTTC | 121339–121318 | 4 |
| D | GGAGACTTCCGGGGCCGTCC | 121326–131307 | 5 |
| E | GGGGCATCACTGTGTTACCC | 121058–121077 | 6 |
| Branch | AGAAGCAGGTGTCTAACCTACNNN | 119484–119464 | 7 |
| End | AGAAGCAGGTGTCTAACCTAC | 119484–119464 | 8 |
| BranchG | AGAAGCAGGTGTCTAACCTACCCG | 119484–119464 121344–121342 | 9 |
| Exon 1 | GCTCCATCGCCTTTCCTGTTC | | 10 |
| Exon 2 | TGACGTCCTCGGCGGCCTC | | 11 |
| Exon 2n | TCCTCTGCCTCTTCCTCCTCG | | 12 |
| Tail | CAAGAGGAAACCTCCCTCGGCCCC CGCGCTGCTTCTGGGCCGCGGGGG CCGAGGAAGTGTG | | 13 |
| PFPML | GGGGCATCACGTGGTTACCC | | 14 |
| PRBAM | GAGACAAGAGGAAGGATCCCTCGG C | | 15 |
| PFBH1 | AGGGATCCTTCCTCTTGTCTCCCTC CCAGG | | 16 |
| PRP31 | GCCAGTGTGATGGATATCTGC | | 17 |
| PFPB1 | CCACACGTGAGACCCCCGAGATGG GCAGG | | 18 |
| PFPB2 | CGCCACGTGGGACGGCCCCGGAAG TCTCC | | 19 |
| PFPB3 | TTCCACGTGCCCCGCGGCCCAGAA GCAGC | | 20 |
| PRPB6 | GGAAACCTCCCTCCCGAGGAAGTG TGCCCGGAAGACG | | 21 |
| PFPB7 | GAGGGAGGTTTCCTCTTGTCTCCC TCCCAGG | | 22 |
| PRPB8 | GGAAACCTCCCTCCCGCGGGCGGC CTCACGCGCTACC | | 23 |
| PFDBG | CGTGGCGCGTCTTACACTTCCTCG GCCC | | 24 |
| PRDBC | AAGACGCGCCACGCGGAGGC | | 25 |
| pFDELA | CAGCGCCGGGGCCTTTCCTCTTGT CTCCCTCCCAGG | | 26 |

TABLE 1-continued

| Probe/Primer | Sequence | Location | SEQ ID NO |
|---|---|---|---|
| PRDELT | AAAGGCCCCGGCGCTGCTTCTGG | | 27 |
| PRPB10 | GGAAAGGTCAGTGGGCCCCCGCGC TGCTTCTGG | | 28 |
| PFPB9 | CACTGACCTTTCCTCTTGTCTCCCT CCCAGG | | 29 |

EXAMPLE 2

Plasmids and Cell Culture (Infected and Transfected)

A. pLAT

To examine the expression of the HSV-1 2.0 kb LAT RNA in transient transfection assays, a LAT minigene expression vector was constructed. A detailed map of the LAT locus and the expression construct is depicted in FIGS. 1A–1C. The 2.8 kb fragment of the mLAT gene as a PstI-MluI restriction fragment of HSV-1 strain F DNA encompassing the 2.0 kb LAT coding region was previously subcloned into the vector pGEM4Z (Promega) to yield pGEM4Z PstI-MluI [Spivack, 1991]. The HSV-1 DNA was removed from this plasmid by digestion with restriction enzymes EcoRI and HindIII and cloned into the polylinker site of the eukaryotic expression vector pcDNA3 (Invitrogen). pcDNA3 expresses the neomycin resistance gene and contains a polylinker region flanked by the cytomegalovirus (CMV) immediate early (IE) gene promoter and the bovine growth hormone (BGH) gene polyadenylation (pA) sequence. Cloning of the HSV-1 DNA between the CMV IE gene promoter and the BGH gene pA signal produced plasmid pLAT (or wild-type vector; see FIG. 1C).

B. pLATΔCMV

Plasmid pLATΔCMV was generated by deletion of the NruI-HindIII restriction fragment containing the CMV IE promoter from the parent plasmid pLAT (FIG. 1C).

C. Cell Culture

CV-1 cells were propagated and maintained in Eagle's minimum essential media supplemented with 5% calf serum at 37° C. with 5% $CO_2$. COS-1 cells were maintained and propagated in Iscove's media supplemented with 5% calf serum at 37° C. with 5% $CO_2$.

D. HSV-1 Preparation

Subconfluent CV-1 monolayers were infected with 1 pfu per cell of HSV-1 strain F or HSV-1 strain 17+, or HSV-1 mutant TB-1. Additionally, COS-1 cells were infected for 16 hours with HSV-1 strain 17+ at an MOI of 1. Virus was concentrated from the media as described [Deatly, A. M. et al, 1987, Proc. Natl. Acad. Sci. USA, 84:3204–3208; Deatly, A. M. et al, 1988, J. Virol., 62:749–756]. Virus titres were assayed on CV-1 and BHK cells.

E. Transfection $7.5 \times 10^5$ to $1.5 \times 10^6$ COS cells were seeded in 100 mm plates and grown overnight. Monolayers at approximately 70% confluence were transfected by the calcium phosphate precipitation method with 20 μg plasmid DNA in 125 mM $CaCl_2$, 25 mM (N-[2-hydroxyethyl]piperazine-N'-[2-ethanesulfonic acid]), 140 mM NaCl, and 0.75 mM $Na_2HPO_4$ (pH 7.05). After 16 hours incubation, cells were washed with phosphate-buffered saline (PBS), shocked with 15% glycerol in PBS for 1 to 2 minutes, washed with PBS and refed with fresh media. At 44 to 48 hours post-transfection, cells were harvested for RNA isolation as described below.

EXAMPLE 3

The 2.0 kb LAT RNA is an Intron Spliced From mLAT in Transient Transfection Assays and Viral Infection The pLAT vector was transfected into COS-1 cells, and at 44–48 hours post transfection, total RNA was prepared from cells or from nuclear RNA fractions or from cytoplasmic RNA fractions and analyzed by Northern hybridization as follows.

A. Fractionation

Transfected cells to be fractionated were washed with PBS and harvested in RSB buffer (10 mM Tris-HCl pH 7.4, 10 mM NaCl, 3 mM $MgCl_2$) at 4° C. After a 10 minute incubation at 4° C., cells were lysed with the addition of 0.1 volume of 10% NP40 and subsequent vortexing. Nuclei were isolated by centrifugation through a sucrose cushion (0.33 M sucrose in RSB buffer).

B. RNA Extraction

Nuclear RNA was isolated from the pellet and cytoplasmic RNA was isolated from the supernatant [Nicosia, 1994]. RNA was isolated using the guanidium thiocyanate extraction/cesium chloride centrifugation procedure of Chirgwin et al, 1979, Biochem., 18:5294–5299, as modified by Spivack 1987. Total RNA and nuclear RNA were isolated by homogenization of cells or nuclei in guanidium thiocyanate solution (4M guanidium thiocyanate, 0.5% sodium lauroylsarcosine, 100 mM β-mercaptoethanol, 25 mM sodium citrate [pH 7.0], 0.1% antifoam A [Sigma Chemical Co.]) for 20 seconds with a cell disrupter (Brinkman Instruments Inc.).

To isolate cytoplasmic RNA, 0.1 volume of extraction buffer (1M β-mercaptoethanol, 0.25M sodium citrate, and 5% sodium lauryl sarcosinate) and guanidium thiocyanate (to a final concentration of 4M) were added to cytoplasmic extracts in RSB buffer.

COS-1 or CV-1 cells were infected at 1 pfu per cell and harvested at 16–20 hours post-infection for total RNA.

C. Northern Analysis

Northern analysis was performed as described [Spivack, 1987] with some modifications. 10 μg aliquots of glyoxalated RNA were electrophoresed on 1.2% agarose gels, vacuum blotted to a nylon membrane (GeneScreen Plus, NEN), and U. V. cross-linked. DNA probes were subfragments of the HSV-1 strain F BamHI fragment B [Post, L. E. et al, 1980, Proc Natl. Acad. Sci. USA, 77:4201–4205]. BamHI(B) subfragments were generated by restriction digestion, isolated by gel electrophoresis and purified. The positions of these fragments relative to the LAT locus are indicated in FIG. 1C.

RNAs were hybridized to heat denatured $^{32}$P-labeled nick-translated DNA probes overnight [Spivack, 1987]. Membranes were washed twice each in 1×, 0.5×, and 0.1× SSPE (180 mM NaCl, 10 mM monobasic sodium phosphate pH 7.7, 1 mM EDTA) with 1% SDS for 20 minutes at 65° C. [Nicosia, 1994].

The position of the oligonucleotide probe Tail, also used as a probe for Northern hybridization, relative to the 2.0 kb LAT RNA is shown in FIG. 1C. The $^{32}$p end-labeled oligo was hybridized to RNAs as outlined above and membranes were washed as indicated except that washes were carried out at 50° C.

All membranes were exposed for autoradiography to Reflection film (Dupont) with an intensifying screen (DuPont).

D. Results

In preparing the first Northern blot, total RNA was also isolated from mock-infected or HSV-1 strain 17+ infected COS-1 cells at 16 hrs post-infection.

Using the protocols described above, the Northern blot was hybridized to three different probes. First, Probe B, 0.9 kb BstEII-BstEII, which overlapped the 2.0 kb LAT as well as the region upstream was used. Probe B detected the expression of three transcripts, 3.4 kb, 2.0 kb, and 1.4 kb in size. The 3.4 kb RNA is mostly nuclear, the 1.4 kb RNA is mainly cytoplasmic, and the 2.0 kb RNA is similarly abundant in equal quantities of nuclear and cytoplasmic RNA. The size and cellular distribution of these transcripts suggested that the 3.4 kb RNA may be the truncated mLAT primary transcript, and the 1.4 kb RNA may be the spliced exons of this transcript.

To clarify the relationship between these three transcripts, the RNAs were mapped by reprobing this blot with two other probes: Probe A, 0.4 kb StyI-StyI, which was specific for sequences 5' to the 2.0 kb LAT, and Probe C, 1.0 kb BstEII-BstEII, which mapped within the 2.0 kb LAT. Northern blots were also routinely probed with plasmid pBSS [Gonzalez, A. M. et al, 1990, J. Cell Biol., 110:753–765], containing the human rRNA 5' external transcribed spacer to verify that cytoplasmic RNA was not contaminated with nuclear RNA [Nicosia, 1994].

Two transcripts, the 3.4 kb and 2.0 kb RNAs were detected with probe C. In virally infected cells, this probe detects the 2.0 kb LAT as well as the antisense ICP0 transcript. Probe A also detects only two transcripts, the 3.4 kb and 1.4 kb RNAs. These results are consistent with the 3.4 kb RNA being the primary transcript from which the 2.0 kb LATin and the 1.4 kb LATex are spliced.

The 1.4 kb transcript was not expected to be the 1.5 kb LAT (FIG. 1B), because this transcript is only observed in latency in small amounts [Spivack 1987, Spivack 1988; Wagner 1988]. In addition, the 1.4 kb RNA does hybridize with probe A which does not overlap with the 1.5 kb RNA observed during HSV-1 latency. The 1.5 kb LAT appears to arise by splicing of a 500 base intron from the 2.0 kb LATin [Spivack 1991] and therefore may be a twintron (LATwin) [Copertino, D. W., and R. B. Hallick, 1991, EMBO J., 10:433–442].

EXAMPLE 4
RT-PCR and Sequencinp of the LAT Splice Junction

To verify that the 2.0 kb LATin and the 1.4 kb LATex are spliced from the primary 3.4 kb RNA transcript, RT-PCR and sequencing were performed.

cDNA was synthesized from total RNA of COS-1 cells transiently transfected with pLAT or CV-1 cells infected with HSV-1 strain F with the Superscript™ Preamplification system (Gibco-BRL) following the manufacturers instructions. Primers Exon 1 and Exon 2, specific for the putative mLAT exons (FIG. 1C), were used to amplify LATex cDNA from transiently transfected cells, or from $H_2O$ as control. PCR amplifications were done with 2.5 U of Taq 2000 polymerase (Stratagene) in 60 mM Tris-HCl, 15 mM $(NH_4)_2SO_4$, 1.5 mM $MgCl_2$ at pH 10.0 (Invitrogen) with 1 µM of each primer and 1 mM deoxynucleotides. Amplifications consisted of 35 cycles of denaturation at 94° C. for 1 minute, annealing at 58° C. for 1 minute, and extension at 72° C. for 1 minute. PCR products were resolved by 2% agarose gel electrophoresis and visualized by ethidium bromide staining. The major 275 bp PCR product was cloned into a TA cloning vector (Invitrogen) and several clones were sequenced by an ABI Prism cycle sequencer. The results showed that these exons are spliced together and identified the SD and SA sites of the 2.0 kb LAT RNA (see FIG. 2).

To determine if splicing of MLAT was also occurring in virally infected cells and if the same SD and SA sites of mLAT were recognized, total RNA from CV-1 cells infected overnight with HSV-1 strain F was also amplified by RT-PCR with primers specific for the putative mLAT exons. In this case primers Exon 1 and Exon 2n were used to amplify LATex cDNA from HSV-1 infected cells or RNA from infected cells (noRT), due to mispriming of primer Exon 2 on viral cDNA. PCR amplifications were done as described above with the following modifications, polymerase was purchased from Fisher, 2.0 mM of $MgCl_2$ were used, and pH was 9.5. Amplifications were similar, except that annealing was at 60° C. Resolution, visualization and cloning of the 245 bp PCR product were performed as above described. The splice junction of the LAT exons identified in transfected and infected cells was the same.

The sequence at the splice junction of the LAT exons (LATex) is shown in FIG. 2, with the corresponding sequences of the mLAT DNA. The GT of the SD site at the 5' end of the 2.0 kb LAT intron (LATin) begins at nucleotide 119464 and the AG of the splice acceptor site of the intron ends at nucleotide 121418 of the HSV-1 genome [McGeoch, D. J. et al, 1988, J. Gen. Virol., 69:1531–1574]. This is in agreement with the previously published SD and SA sites of the 2.0 kb LAT intron [Farrell, 1991].

A minor 400 bp PCR product was also occasionally amplified by RT-PCR from cells transfected with the pLAT. The SD and SA sites of the 2.0 kb LAT at nucleotides 119464 and 121418 were used, but this product contained an additional exon corresponding to nucleotides 119611–119739 of the LAT gene. The sequence at 119739 is the SD site of the inner intron of the 2.0 kb LAT RNA, which was thought to be neuron-specific [Spivack, 1991]. These splicing events are attributed to overexpression of the LAT RNA in transfected cells relative to virally infected cells. These products are not amplified from virally infected cells.

A summary of the results of these preceding experiments is as follows: The nuclear localization of the 3.4 kb RNA and the mostly cytoplasmic localization of the 1.4 kb RNA, as well as the sizes of these transcripts, suggested that the 3.4 kb RNA is a truncated mLAT pre-mRNA and the 1.4 kb RNA is the spliced exons of MLAT (LATex). Mapping of the transcripts by Northern hybridization and RT-PCR and partial sequencing of the 1.4 kb LATex confirmed this hypothesis. The SD and SA sites of the 2.0 kb LATin, as determined by sequencing of the splice junction of LATex cDNA, are the expected conyensus sequences CAG/GT and NYAG/G respectively. Immediately upstream of the splice acceptor AG is a stretch of 19/20 pyrimidines comprising the polypyrimidine tract associated with the splice acceptor site. Significantly, although the viral mLAT pre-mRNA and LATex transcripts are not detectable by Northern hybridization, the same SD and SA sites of mLAT are recognized in productive viral infections.

The splicing of the mLAT to yield the LATex mRNA generates a new open reading frame, which has previously been referred to as open reading frame b (ORFB) [Lagunoff, 1994]. ORFB is not well conserved between HSV-1 strains F and 17+ [Wechsler, 1989; McGeoch, 1988; Lagunoff, 1994]. The protein encoded by ORFB has not been detected in productively infected cells [Lagunoff, 1994] although it may be expressed during HSV-1 latency or reactivation.

The cellular localization of the 2.0 kb LATin is unusual. In transiently transfected COS-1 cells, a significant amount of the 2.0 kb LATin is cytoplasmic (FIG. 2). Nevertheless, this corresponds to what is observed in HSV-1 infected CV-1 cells and murine brainstem cells [Nicosia, 1994]. Additionally, the localization of the 2.0 kb LATin in transfected cells demonstrates that no viral gene products are required for cytoplasmic LATin localization. In latently infected neurons, the 2.0 kb LATin and the smaller 1.5 kb LATwin are nuclear localized [Stroop, W. G. et al, 1984, Lab. Invest., 51:27–38; Spivack 1987; Stevens 1987]. It is unclear what cellular mechanism mediates the localization of 2.0 kb LATin, but likely it is related to the dynamic state of the cell.

EXAMPLE 5
The 2.0 kb LAT RNA as a Primary Transcript Expressed From the LAP2 Promoter Could Not Be Detected The sequences for the LAP2 promoter element lie within the LAT sequences of pLAT. To assess the contribution of this promoter element toward the synthesis of the 2.0 kb LAT RNA in this system, plasmid pLATΔCMV (Example 2; FIG. 1C) was used. Total RNA was isolated from COS-1 cells transfected with pLAT or the CMV promoter deletion mutant pLATΔCMV which still retains the LAP2 promoter sequences (LAP2). Total RNA was prepared from mock transfected cells and cells 44 hrs post-transfection. The RNA was analyzed by Northern hybridization with probe C. Although the LAP2 sequence elements are present in pLAT the promoter is not very active in transfected COS-1 cells. As was seen in the Northern blot (not pictured), the amount of 2.0 kb LAT RNA detected in cells transfected with the plasmid pLATΔCMV was low compared to the level detected in cells transfected with pLAT. The levels of 2.0 kb LAT RNA produced by the pLATΔCMV vector were consistently at least 100 fold less than that observed for the wild-type expression plasmid pLAT. By phosphorimager analysis (Molecular Dynamics), the ratio of LAT RNA expression of wild-type pLAT to this mutant is approximately 500:1 in this experiment, and was consistently greater than 100:1 in different experiments. Thus, LAP2 promoter sequences do not contribute significantly to the levels of 2.0 kb LAT RNA observed in this system.

To determine whether the 2.0 kb LAT RNA synthesized from the LAP2 promoter is a primary transcript, the presence and abundance of the LATex spliced exons was assayed by semi-quantitative RT-PCR using primers Exon 1 and Exon 2. LATex cDNA was amplified from cells transfected with pLAT as well as the vector deleted for the CMV IE promoter element. The ratio of LATex expressed by pLAT to that expressed by the mutant was approximately 200:1. The difference in expression of LATex assayed by RT-PCR corresponds to the difference in expression of LATin assayed by Northern hybridization. This suggests that LAP2 promoter driven transcription of the 2.0 kb LAT RNA may not initiate at the SD site in pLAT.

If the 2.0 kb LAT RNA is produced as a primary transcript from LAP2, this does not contribute significantly to the amount of LAT RNA observed in this system. Thus, the majority of the 2.0 kb LAT RNA produced by this vector is an intron accumulating after splicing. The small amount of 2.0 kb LAT RNA produced by the LAP2 promoter may also be an intron. RT-PCR amplification of LATex with primers Exon 1 and Exon 2 from cells transfected with pLATΔCMV suggests that transcription of the 2.0 kb LAT RNA from LAP2 may initiate upstream of the SD site of the intron.

EXAMPLE 6
Mapping of the 2.0 kb LAT Intron Branchpoint

Because the 2.0 kb LAT RNA is an intron, some of the molecules may be in a lariat conformation. As such, the 2.0 kb LAT RNA should be branched. The branchpoint of this intron was mapped using a novel RT-PCR technique. DNAse treated total RNA isolated from COS-1 cells transfected with pLAT (the substrate for DNA synthesis) or CV-1 cells infected with HSV-1 strain F was transcribed into cDNA with the Superscript™ Preamplification system (Gibco-BRL) following the manufacturers instructions for high G-C templates.

A. Transfected Cells cDNA was synthesized from transfected cell RNA with primer Branch at 50° C. for identification of the LAT intron branchpoint and for amplifications with a primer complementary to the 5' end of the 2.0 kb LAT RNA (End) and an upstream primer (E) (FIG. 3). cDNA was synthesized at 42° C. for amplifications with primer E and primers A, B, C, or D. Primer Branch is complementary to the 5' end of the 2.0 kb LAT RNA with the addition of three degenerate nucleotides at the 3' end of the primer to extend the area of hybridization passed the putative branched nucleotide (FIG. 3).

PCR amplification of cDNAs, RNA from transfected cells (noRT), and $H_2O$ was done with primer sets E and End, E and D, E and C, E and B, and E and A. PCR amplifications with primers E and D, E and C, E and B, or E and A were done with 2.5 U of Taq polymerase (Fisher) in 60 mM Tris-HCl, 15 mM $(NH_4)_2SO_4$, 2.0 mM $MgCl_2$ at pH 10.0 (Invitrogen) with 1 μM of each primer and 1 mM deoxynucleotides. Amplifications consisted of 35 cycles of denaturation at 94° C. for 1 minute, annealing at 60° C. for 1 minute and extension at 72° C. for 1 minute.

PCR amplifications for the LAT branchpoint were done using primers E and End with 2.5 U of Taq polymerase (Fisher) in 60 mM Tris-HCl, 15 mM $(NH_4)_2SO_4$, 1.5 mM $MgCl_2$ at pH 9.0 (Invitrogen) with 1 μM of each primer and 1 mM deoxynucleotides. Amplifications consisted of 35 cycles of denaturation at 94° C. for 1 minute, annealing at 71° C. for 1 minute, with the temperature dropping 1° C. every 4 cycles and the final 15 cycles at 66° C., and extension at 72° C. for 1 minute.

RT-PCR amplified products of the 2.0 kb LATin branchpoint from the transiently transfected cells were resolved using a 2% agarose gel electrophoresis and visualized in ethidium bromide as above described. The PCR product containing the branchpoint of the 2.0 kb LAT intron appears at about 325 bp MW. Two major PCR products are visible at 300 bp and 250 bp.

The PCR products were cloned into a TA cloning vector and subsequently sequenced as above. Due to limited mispriming of the Branch degenerate primer during cDNA synthesis at 42° C., a series of PCR products were amplified from the 3' end of the 2.0 kb LATin using primers E and D, E and C, E and B, or E and A. Primer D begins 91 bases upstream of the 3' end of the 2.0 kb LATin and primer A begins at the SA site at the 3' end of the 2.0 kb LATin. PCR products were amplified from the 3' end of the LATin with these primer sets for size comparison to branchpoint PCR products.

Most intron branchpoints lie within 100 bases upstream of the SA site [Moore, M. J. et al, 1993, in R. F. Gesteland and J. F. Atkins (ed.), The RNA World: the nature of modern RNA suggest a prebiotic RNA world., Cold Spring Harbor Laboratory Press, Cold Spring Harbor, N.J., pp. 1–30], so it was anticipated that the size of the branchpoint PCR product would probably be larger than that of the PCR product amplified by primers E and D.

Figure 4A:
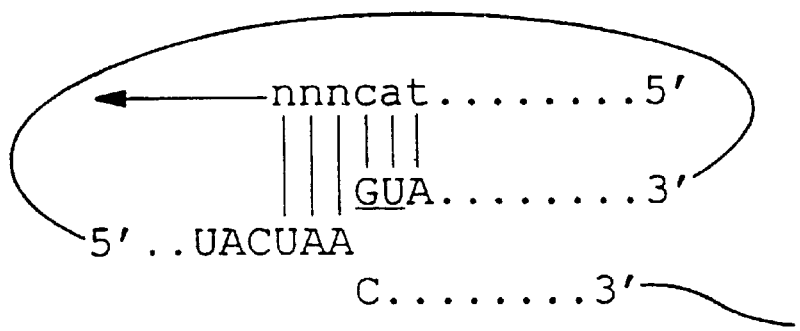
FIG. 4A is a schematic diagram of RT-PCR primer hybridized to a yeast consensus branchsite sequence (UACUAAC) [SEQ ID NO: 1] of an intron, depicted in lariat conformation. The branched nucleotide A is shown in bold and underlined. The underlined SD site, GU, at the 5' end of the intron is linked to the branchpoint A by a 2'–5' phosphate linkage. The primer used for cDNA synthesis is shown in lowercase hybridized to the 5' end of the intron containing the SD sequence. The three degenerate nucleotides (n) of the primer for cDNA synthesis are lacking in the primer for PCR. The arrow indicates the direction of synthesis.
Figure 4B:
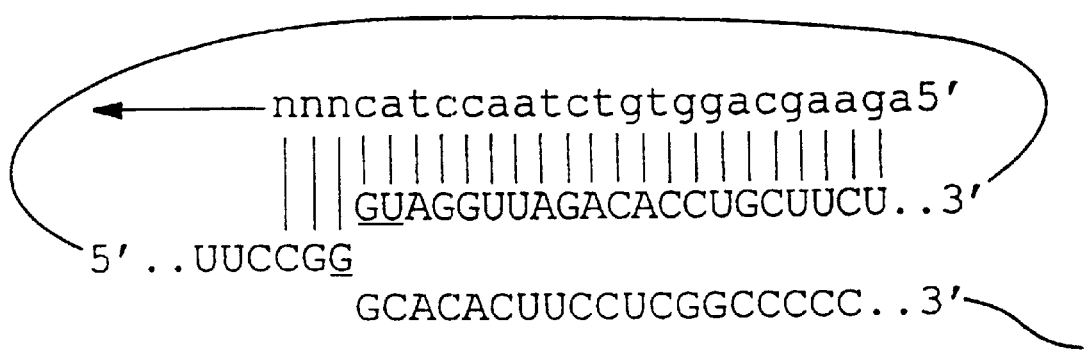
FIG. 4B illustrates the identification of the branchpoint of the HSV-1 LATin, which is depicted in a lariat conformation. The primer Branch used for cDNA synthesis is shown hybridized to the 5' end of LATin containing the SD sequence. The underlined SD site, GU, is linked by a 2'–5' phosphate linkage to the underlined branchpoint nucleotide. The arrow indicates the direction of cDNA synthesis. The three degenerate nucleotides (n) at the 3' end of primer Branch for cDNA synthesis are lacking in primer End used for PCR. The branchpoint G at position 121344 (33) is shown in bold and underlined.
Figure 4C:
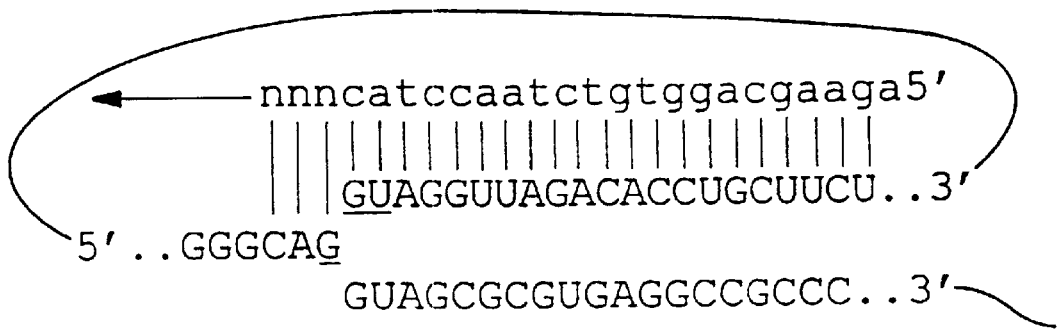
FIG. 4C is similar to FIG. 4B except that the G at position 121283 was also identified as a potential branchpoint sequence with this technique and is shown underlined.

The two PCR products of 250 bp and 300 bp obtained by the above procedures, cloned into the TA cloning vector and sequenced produced the following results. The nucleotide 5' to the SD site of the intron in the 300 bp PCR product was the G at position 121344 of the HSV-1 genome [McGeoch 19881. In the 250 bp PCR product the nucleotide 5' to the SD site of the 2.0 kb LAT was the G at position 121283. These sequences are shown in FIG. 4B and FIG. 4C, respectively, hybridized to the primer Branch. Sequences 3' to the G at position 121344 show no complementarity to primer Branch; however, the four nucleotides 3' to the G at position 121283 are complementary to the four nucleotides in primer Branch 5' to the 3 degenerate bases at its 3' end (see FIG. 4C). It is likely that the 250 bp PCR product may result from a misprime at the level of cDNA synthesis, although the G at position 121283 may be another LATin branchpoint identified by this technique.

B. Infected Cells

To identify the LATin branchpoint from virally infected cells, cDNA was synthesized from total RNA of CV-1 cells infected with HSV-1 strain F using primers Branch, Branch G, End or random primers at 50° C. In primer BranchG, the three degenerate nucleotides at the 3' end of the primer are replaced with the bases complementary to the branchpoint sequence of LATin at position 121344 identified from the LAT expression plasmid (see FIG. 4B). The viral LATin branchpoint of cDNAs, RNA from infected cells (noRT) and H$_2$O was amplified by PCR with primers E and End.

Amplifications were done with 2.5 U of Taq polymerase (Fisher) in 60 mM Tris-HCl, 15 mM (NH$_4$)$_2$SO$_4$, 1.5 mM MgCl$_2$ at pH 9.0 (Invitrogen) with 1 µM of each primer and 1 mM deoxynucleotides. Amplifications consisted of 35 cycles of denaturation at 94° C. for 1 minute, annealing at 71° C. for 1 minute with the temperature dropping 1° C. every 4 cycles and the final 15 cycles at 66° C., and extension at 72° C. for 1 minute.

PCR amplified products of the 2.0 kb LATin branchpoint from the virally infected cells were resolved and visualized as above described. Again, two major PCR products are visible at 300 bp and 250 bp. The major 300 bp PCR products of primers E and End were cloned into a TA cloning vector (Invitrogen) and a number of clones were sequenced. The sequences of these RT-PCR products were the same as those amplified from cells transiently transfected with pLAT. Therefore, the G at position 121344 is also the branchpoint of the LAT intron in virally infected cells.

C. Control

As a control for determining which nucleotide within the branchpoint region was the nucleotide which had formed a 2'–5' phosphodiester bond with the 5' SD site, RT-PCR was also done on introns with the yeast consensus branchpoint sequence 5' UACUA$\underline{A}$C 3' (SEQ ID NO: 1]. In yeast, the intron containing the mutant branchpoint sequence UACUA C$\underline{C}$ [SEQ ID NO: 39], with the underlined cytosine identified as the branchpoint, accumulated to high levels in a lariat configuration in vivo and was not efficiently debranched in vitro [Jacquier, A., and M. Rosbash, 1986, Proc. Natl. Acad. Sci. USA 83:5835–5839]. The underlined A is utilized as the branchsite in this sequence [Moore, 1993]. Sequenced RT-PCR products revealed that the nucleotide 5' to the SD site was the branched nucleotide (FIG. 4A). By analogy, the G at position 121344, the nucleotide 5' to the SD site in the LAT branchpoint PCR product, is the branched nucleotide of this intron (FIG. 4B).

Most introns are rapidly degraded within seconds of release from spliceosomes in vivo [Moore, 1993]. The degradation of introns is thought to involve debranching of the intron followed by exonucleolytic cleavage [Chapman, K. B. and J. D. Boeke, 1991, Cell, 65:483–492]. Guanosine branchpoints are poor substrates for mammalian debranching activity [Arenas, J., and J. Hurwitz, 1987, J. Biol. Chem., 262:4274–4279]. The debranching of guanosine branchpoints occurs at approximately 50% the rate of adenosine branchpoints in vitro.

The unusual branchpoint sequence of the 2.0 kb LAT intron may regulate LAT gene expression by regulating the splicing of mLAT. If this branchpoint sequence is poorly recognized or inhibits exon joining, unspliced mLAT or splicing intermediates would be degraded. As a result, only low levels of spliced LATex mRNA would be generated, consistent with is observed in the examples.

The HSV-1 2.0 kb LAT and HSV-2 2.3 kb LAT, which overall share little homology (50%), are highly homologous at their 3' ends (80%) [Krause, 1991; McGeoch, 1998] due to overlap with the ICP0 mRNA coding region on the opposite strand (FIG. 1). The 3' ends of the HSV-1 and HSV-2 LATs are shown in FIG. 5. Interestingly, there is a base change between the two viruses within the branchsite sequence of the HSV-1 LATin. The corresponding sequence in HSV-2, UUCuG$\underline{GG}$ [SEQ ID NO: 40], shares less homology to the consensus mammalian branchpoint sequence YNYUR$\underline{A}$C [SEQ ID NO: 30] than the HSV-1 branchsite UUCCG$\underline{GG}$ [SEQ ID NO:31]. Thus, it is unclear whether this sequence in HSV-2 would be recognized as the [SEQ ID of this intron.

The branchpoint G of the HSV-1 LATin at position 121344 is complementary to the last base of the ICP0 codon 621, GC$\underline{C}$, coding for alanine [McGeoch, 1991]. In HSV-2, the corresponding G is complementary to the last base of the HSV-2 ICP0 codon 663, GC$\underline{C}$ for alanine [McGeoch, 1998]. Changing the HSV-1 branchpoint guanosine to the usual branchpoint nucleotide adenosine would alter these codons to GC$\underline{U}$, which still encodes alanine. Thus, there appears to be no selective pressure maintaining this nucleotide as a G. Indeed, the base preceding this G is altered in HSV-2, and yet the corresponding ICP0 codons in both HSV-1 ($\underline{C}$GG) and HSV-2 ($\underline{A}$GG) encode the amino acid arginine.

Figure 6:
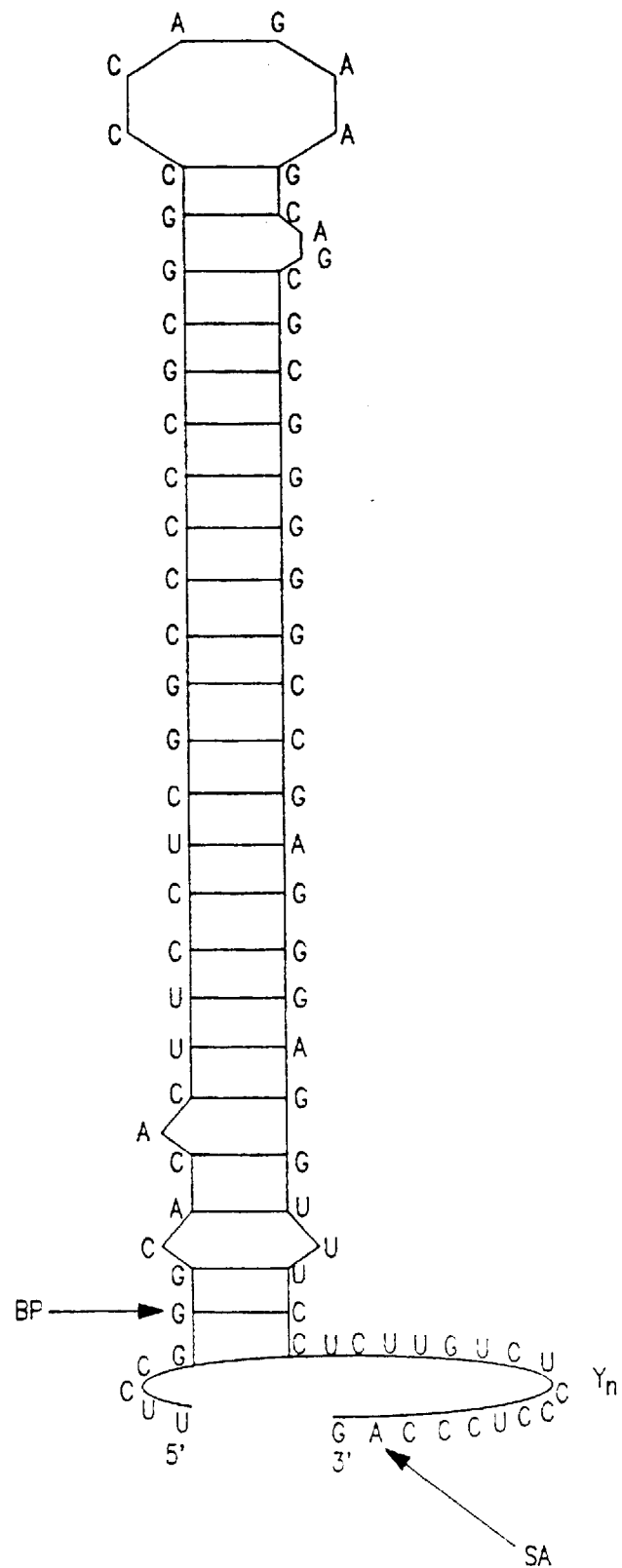
FIG. 6 is a schematic diagram of the potential secondary structure at the 3' end of the 2.0 kb LAT RNA. The branchpoint G (BP) and SA site nucleotides are shown in bold and indicated by arrows. The polypyrimidine tract $(Y_n)$ is shown upstream of the SA site. The ΔG of this hairpin is calculated to be −39.7 kcal/mol using Version 7.0 of the GCG Package software (Genetic Computer Group, Inc., Madison, Wis.).

The choice of this LAT branchpoint may be facilitated by the secondary structure of the 3' end of the intron. The secondary structure of the RNA between a potential branchpoint sequence and the 3' splice site may regulate splicing [Balvay, L. et al, 1993, Bioessays, 15:165–169]. A schematic diagram of the potential secondary structure in this region is shown in FIG. 6. There is a potential hairpin structure between the polypyrimidine tract and the 3' splice site and the identified branchpoint sequence of this intron. The ΔG of this hairpin is calculated to be −39.7 kcal/mol using Version 7.0 of the GCG Package software (Genetic Computer Group, Inc., Madison, Wis.), which suggests that this is a stable stem-loop structure. This hairpin may be a critical element influencing the selection of the LATin branchpoints. Additionally, the LATin 3' end which is detectable on at least a proportion of the transcripts may also stabilize the intron. This potential hairpin may augment the stability of this intron by blocking the branchpoint from debranching enzymes.

Selection of guanosine branchpoints within a consensus branchsite sequence in vitro is inefficient and inhibits subsequent exon joining [Freyer, G. A. et al, 1987, J. Biol. Chem., 262:4267–4273; Hornig, H. et al, 1986, Nature 324:589–591; Query, 1996]. The selection efficiency of the 2.0 kb LATin guanosine branchpoint was not determined. Nevertheless, this was the only branchpoint identified.

although using this RT-PCR technique has enabled amplification of branchpoint sequences of introns which do not accumulate (FIG. 4). Additionally, accumulation of unspliced mLAT pre-mRNA or splicing intermediates of mLAT is not observed during HSV-1 infection or transient transfections with our LAT expression vector. This may be due to the degradation of these intermediates. Alternatively, selection of the LATin branchpoint may not be inefficient or inhibitory to exon joining due to the surrounding sequences which bear little homology to the consensus mammalian branchsite sequence or to a novel branchpoint selection mechanism.

EXAMPLE 7
The Tail of the 2.0 kb LAT RNA is Detectable in Transfected and Infected Cells To determine if the tail of the 2.0 LAT RNA downstream of the branchpoints was present on the 2.0 kb LAT RNA, the Northern blot described in Example 6 was reprobed with the probe Tail (see FIG. 1).

Total RNA was prepared from COS-1 cells; from nuclear and from cytoplasmic fractions, and from mock-infected cells, the cells either infected or not infected with HSV-1 stain 17+. In addition to these preparations, total RNA isolated from CV-1 cells infected with HSV-1 strain F at 16 hour post-infection was also probed with probe Tail.

The gel revealed that Probe Tail detected the 2.0 kb LAT RNA in total, nuclear and cytoplasmic fractions of cells transfected with the LAT mini-gene expression plasmid. Probe Tail also detected the 2.0 kb LAT RNA from COS-1 cells infected with HSV-1 strain 17+ or CV-1 cells infected with HSV-1 strain F (16 hour post-infection). These data indicate that the tail of the 2.0 kb LAT RNA is present on at least a proportion of the 2.0 kb LAT RNA molecules.

Notably absent near the 3' end of the LATin is the mammalian branchsite consensus sequence, YNYURAC [SEQ ID NO:30], with the branchpoint at the adenosine [Moore, 1993]. The branchsite of LATin, UUCCGGG [SEQ ID NO:31], bears little homology to that consensus branchsite sequence. The sequence UUCUAAC [SEQ ID NO:32], a consensus branchsite, is present at position +690 relative to the 5' end of the LATin. This sequence lies in the smaller 500 base intron within the 2.0 kb LAT intron, and is presumably utilized as the branchpoint in the splicing of this intron to generate the 1.5 kb LATwin observed in latently infected neurons [Spivack, 1991].

By Northern hybridization, the tail of the 2.0 kb LAT RNA downstream of the branchpoint is detectable on at least a proportion of the 2.0 kb LAT RNA in transfected and infected cells, as described above. Because exonucleolytic degradation of RNA appears to follow debranching of lariat intermediates [Chapman, K. B., and J. D. Boeke, 1991, Cell, 65:483–492], it is likely that at least some of these molecules are in a lariat conformation.

EXAMPLE 8
Additional pLAT Mutant Plasmids pLAT of Example 2 (also referred to as wt vector) served as backbone for subsequent mutations. Primers used in the following constructions are described in Table 1.

A. Mutants pΔHpa and pΔXcm were generated by removal of the corresponding restriction fragment (Hpa and Xcm, respectively) and self-ligation. Prior Klenow fill-in was necessary in the case of pΔXcm.

B. To construct pΔBfa, the 2.8 kb EcoRI-HinduIII fragment from pLAT was isolated and digested with BfaI. The resulting 2110 bp HindIII-BfaI and 400 bp BfaI-EcoRI fragments were purified and ligated directly in the EcoRI-HindIII digested pLAT.

C. pHλ+ and pHλ- were generated by the insertion in pΔHpa of the 440 bp HpaI fragment of lambda phage DNA from plasmid pNF1. In pHλ- the insert is in the same orientation as in the TB1 virus (this is referred to as the TB1-like mutant); it is in the opposite orientation in pHλ+.

D. pBam was generated by site-directed mutagenesis in order to create a unique BamHI site towards the 3' end of the 2.0 kb LAT. Fragments from pLAT were amplified by PCR with primers PFPML and PRBAM or with PFBH1 and PRP31. Both amplified products were purified from agarose gels and mixed equally in a second PCR reaction using PFPML and PRP31 as amplification primers. The 700 bp final product was digested with EcoRI and BbrPI (PmlI) and cloned into the corresponding sites of vector pLAT.

E. pλ+ was generated by the insertion of a linker (GATCGTACTAAC) [SEQ ID NO:33] containing the yeast consensus branch point sequence into the Bam HI site of pBam. In pY- the same linker is inserted in the opposite orientation.

F. pΔPB was obtained after removal of the PmlI-BamHI fragment from pBam, Klenow fill-in and self ligation of the vector.

G. To generate plasmids pΔ#1, pΔ#2, pΔ#3, DNA from pLAT was amplified using respectively, PFPB1, PFPB2, PFPB3 and PRP31; fragments were gel purified, digested with EcoRI and PHmlI and cloned into the corresponding sites of pLAT.

H. To obtain pΔ#4, DNA from pLAT was amplified with PRPB6 and PFPML or with PFPB7 and PRP31; amplified fragments were gel purified and equally mixed in a PCR reaction using PFPML and PRP31 as primers. The final product was digested with PmlI and EcoRI and cloned into the corresponding sites of pLAT.

I. pΔ#5 was generated following the same method as above but replacing PRPB6 by PRPB8.

J. pΔG was engineered in the same way using primers PFDBG and PRP31 or primers PFPML and PRDBC. The resulting products were gel purified, mixed in a second amplification reaction with primers PFPML and PRP31. The final 700 bp product was purified, digested with PmlI and EcoRI and cloned in the corresponding sites of pΔ#3.

K. pΔA was made the same way as described in part J above with primers pFDELA and PRDELT used in the first-step PCR reactions.

L. pCons was generated following the same procedures used to generate pBam above, using PCR primers PRPB10 with PRPML and PFPB9 with PRP31 in the first step PCR amplifications.

All amplification reactions were performed in the same conditions: 35 cycles 1 minute at 94° C., 1 minute at 60° C. (58° C.), 1 minute at 72° C., in 1×PCR buffer [60 mM Tris-HCl (pH 9.5), 15 mM $(NH_4)_2SO_4$, 1.5–2.0 mM $MgCl_2$] 0.2 mM (each) deoxynucleotide triphosphate, 1 μM each oligonucleotide and 0.5 U Taq polymerase (Fisher Scientific). Five cycles with an annealing temperature of 58° C. were performed in absence of oligonucleotides prior to standard amplification in the second-step PCR of mutagenesis when two PCR fragments had to be linked together as template.

EXAMPLE 9
Transfection, RNA Extraction and Northern Blot

A. Transfection

20 μg of plasmid per 10 cm dish were transfected into subconfluent Cos-1 cells monolayers using calcium phosphate precipitation as described above. Cells are left with the precipitate for 16 hours, then shocked in PBS with 15% glycerol for 2 minutes, washed with PBS and incubated for 22–24 hours at 37° C. Alternatively subconfluent CV-1 cells were infected with 1 PFU per cell of TB1 or HSV-1 F virus.

B. RNA Extraction

RNA was isolated 16 hours post infection. Cells were lysed in 3.5 ml lysis buffer (4M guanidine isothiocyanate, 0.5% Na N-lauroylsarcosine, 100 mM beta-mercaptoethanol, 25 mM Na citrate pH 7.0 and 0.1% antifoam A). DNA was sheared for 10 seconds by a mechanical disrupter (Brinkmann Instrument Inc.). Total RNA was pelleted though a cushion of 5.7 M CsCl, 0.1 M EDTA by centrifuigation at 150000×g for 20 hours at 18° C. The RNA pellet was resuspended in H$_2$O and precipitated with ethanol. RNA was stored in ethanol at −70° C.

C. Northern Blot

RNA was resuspended in H$_2$O and A260 was measured spectrophotometrically. Five µg of total RNA were used in gel electrophoresis on a 1.2% agarose gel and transferred on Gene Screen Plus (NEN) membranes as previously described (Spivack 1988). Filters were prehybridized for 2 hours at 50° C. in 50% formamide, 10% dextran sulfate, 1× Denhardt's, 1% SDS 5× SSC, 1 mM EDTA and 0.1% denatured salmon sperm DNA. The $^{32}$P-labeled nick-translated probe was heat denatured, added to the prehybridization mix and incubated overnight at 50° C. The blots were washed in decreasing concentrations of SSPE (1×, 0.5× and 0.1×) with 1% SDS at 65° C., twice for 20 minutes per wash and exposed on a phoshorimager screen. Bands were quantified with an ImageQuant v1.1 software.

EXAMPLE 10

RT-PCR

To characterize the splice junctions of LAT, cDNA was synthesized from 1 µg of DNAse treated total RNA using the Superscript™II preamplification kit (Gibco BRL). The manufacturer's protocol for high GC content RNA was followed with the use of both polydT and random hexanucleotide primers. PCR was performed on 20 ng of cDNA with 1 µM primers Exon 1 and Exon 2n in 1× PCR buffer [60 mM Tris-HCl (pH9.5), 15 mM (NH$_4$)$_2$SO$_4$, 1.5–2.0 mM MgCl$_2$], 0.2 mM (each) deoxynucleotide triphosphate, and 0.5 U Taq polymerase (Fisher Scientific) in a 50 µl reaction. The conditions of the 35 amplification cycles were 1 minute at 94° C., 1 minute at 60° C., 1 minute at 72° C. Five µl of the reaction product were electrophoresed on a 2% agarose gel and visualized by ethidium bromide staining. Amplified bands were extracted from the gel using a Geneclean kit (Bio 101, Inc.), cloned into a TA vector (Invitrogen) and sequenced by an ABI Prism cycle sequencer.

To map the branch point of the different introns, RT-PCR was performed as described in Example 6. Briefly, cDNA was synthesized from 10 µg of DNAse-treated total RNA using primer Branch. PCR amplification was performed with primers PFPML and PREND. PCR products were isolated from 2% agarose gels and cloned in TA vector (Invitrogen) and sequenced.

EXAMPLE 11

Effects of the Insertion of Lambda DNA in the 2.0 kb LAT on Splicing

The HSV-1 insertion mutant named TB1, which has a 168 nucleotide deletion in the middle of the 2 kb LAT region replaced by 440 nucleotides of lambda phage DNA has been shown to be unable to express a stable 2.0 kb LAT in lytically infected cells or latently infected animals [T. M. Block et al, 1990, *J. Virol.*, 64:3417–3426]. In order to determine the mechanism underlying this phenotype, a LAT expressing plasmid vector pHλ- was constructed in which the TB1 mutation was recreated (see Example 8C). As controls, the same LAT fragment was simply deleted in pΔHpa or replaced with the phage sequence in the reverse orientation in pHλ+ (see FIGS. 7A–7C).

Cos-1 cells were transfected with LAT expressing vectors (wt or pLAT, pΔHpa, pHλ-, pHλ+). Alternatively, CV-1 cells were infected with TB1 virus and RNA collected 16 hours post infection. Total RNA was collected after 40 hours and 5 µg were electrophoresed and subjected to Northern blot analysis as described in Examples 9 and 10.

Three non-overlapping probes designed to detect either the intron or the first exon were used in the Northern hybridization to map the different transcripts from the LAT locus (FIGS. 7A–7C). The first probe was a 0.59 kb BspMI-SphI fragment specific for the 5' end of the 2.0 kb LAT intron, upstream of the lambda phage DNA insertion. This probe detected the normal 2.0 kb LAT expressed by the wt construct. When cells were transfected with pΔHpa or pHλ+, the accumulated intron is also visible, although with a different size corresponding to the deletion or insertion. However, in the case of the TB1-like mutant pHλ-, no LAT RNA was detected by this probe.

The same RNA described above was also hybridized with a second 2.0 kb LAT specific probe, a 1 kb BstEII-BstEII, which covers most of the 3' end of the 2.0 kb LAT downstream of the λ phage DNA insert, the missing HpaI fragment and extends 210 nucleotides upstream of the 5' HpaI site. The wt 2.0 kb LAT as well as introns from pΔHpa and pHλ+, could be detected by this probe. In the case of pHλ- a smaller RNA of about 1 kb was detected. A transcript with the same size was also produced following infection of CV-1 cells with the TB1 virus. This viral transcript was previously detected but without precise mapping in the LAT locus [Block, cited above].

With the intronic 3' probe, low levels of primary transcripts were detected following transfection of the different constructs; however, no band indicating such a transcript could be detected following infection with TB1. At the very most a faint smear at high molecular weight could be detected probably due to probe hybridization with genomic HSV-1 DNA. The location of a pA signal relatively close to the end of the intron in the cloning vector allows easier detection of the truncated mLAT as compared to the viral mLAT. This may be due to greater homogeneity, or stability of this truncated primary transcript.

Finally, the RNA was hybridized with a 0.37 kb StyI-StyI fragment specific for Exon 1 of the LAT which does not overlap the 2.0 kb intron. Spliced exons of the expected size (1.4 kb) are produced after excision of the 2.0 kb LAT from the primary transcript. Deletion of the HpaI region (pΔHpa) or insertion of the lambda phage DNA in the pHλ+ construct did not affect the production or the size of the mature exons. However, after transfection of the pHλ- construct the mature RNA produced is 0.4 kb larger than expected. In contrast, no detectable amount of transcripts containing Exon 1 was found in infected cell RNA. This reflects the extremely low abundance of viral primary and mature LAT transcripts following HSV-1 infection.

In addition to intron or mature exons all the probes used could potentially detect the 3.4 kb primary transcript discussed in the examples above. The abundance of this transcript appeared to be very low, suggesting a high efficiency of splicing. Thus, depending on the probe used, the primary transcript did not always appear on the blots after a short exposure.

The expression of the TB1-like mutant LAT in transient transfection assay indicated that LAT was made in the TB1-homolog construct as it is made by the TB1 virus. Although primary transcripts or mature RNA could not be observed, the presence of an RNA mapping to the 3' end of the 2.0 kb LAT intron was detected by northern blot analysis in both infected and transfected cells. However, the insertion of lambda phage DNA in an orientation-dependent manner strongly affected splicing of the LAT primary transcript.

To compensate for the absence of a characterized functional agent studies have been based on HSV-1 mutants unable to express the LAT RNA. Most of these mutants bear deletions in the LAT region which mainly affect the promoter region. Such mutants are impaired in transcription of the LAT and allowed mapping of the regulatory elements essential for LAT expression. The viral phenotype associated with the absence of LAT gene expression is a slower kinetics of reactivation from the latent state.

In the panel of LAT negative mutants, the TB 1 virus represents an exception in the way that its mutation is an insertion that does not affect directly the LAT promoter. The TB1 mutation consists in the insertion of foreign DNA in the middle of the 2.0 kb LAT sequence. As a consequence no 2.0 kb LAT could be detected in infected cells or in latently infected murine trigeminal ganglia. The use of an artificial expression system for LAT RNA allowed the understanding of how the 2.0 kb LAT expression is altered in the TB1 virus. It is clear that neither the small deletion of 167 bp in the middle of the 2.0 kb LAT nor the insertion of foreign sequence in this molecule are sufficient to alter the production of a LAT intron. However, the specific sequence inserted in the TB1 LAT locus contains regions acting as SD and SA sites. Thus TB1 is able to express LAT related transcripts; however the final introns and mature RNA are altered as compared to wt.

Another mutant virus 17N/H carry the same lambda sequence replacing the larger NotI-HpaI fragment of the LAT locus. Most of the LAT promoter, the whole Exon 1 and the first half of the 2.0 kb LAT are missing in this virus. However, the lambda insert, its boundary with viral sequences and the downstream region of 2.0 kb LAT are comparable in TB1 and 17N/H. The small LAT transcript of 17N/H maps directly downstream of the lambda insert without significant extension into the phage sequence. Although in this case the promoter and SD at the origin of this possible intron are not identified.

The TB1 mutant does not display any phenotypic difference from its parental strain (HFEM) in growth ability or reactivation kinetics. Thus the modified products of the TB1 LAT gene prove to be functional. If a yet undiscovered protein translated from the mature LAT mRNA is the active agent then alteration of splicing between Exons 1 and 2 are not significantly affecting its production or activity. Since the 2.0 kb LAT is unusually stable it is most commonly thought as an RNA active by itself.

The ICP0 RNA transcribed from the opposite strand largely overlap with the 3' end of the 2.0 kb LAT RNA. The truncated and still stable 0.95 kb TB1 LAT intron retains the complete region antisense to the ICP0mRNA. Thus the absence of phenotype of TB1 is consistent with the antisense hypothesis. Contrary to TB1 the 17N/H mutant shows a retarded kinetics of reactivation and a small plaque phenotype. Since both mutants produce a similar 0.95 kb LAT the difference in phenotype appears to lie in the upstream region of the LAT locus.

EXAMPLE 12

Alternative Splicing of the Mutant TB1 2.0 kb LAT

To further characterize the LATs in the TB1 mutant virus, mapping of the SD and SA was performed using RT-PCR on RNA from transiently transfected or infected cells. Total RNA from Cos-1 cells was collected 40 hours post transfection with the different constructs (wt, pΔHpa, pHλ-, pHλ+). RNA from CV-1 cells 16 hours post infection with HSV-1 strain F or HSV-1 TB1 mutant was also collected. One μg was subjected to DNAse treatment and reverse transcribed into cDNA. The equivalent of 20 ng was used as template for PCR using primers Exon 1 and Exon 2n.

Figure 8:
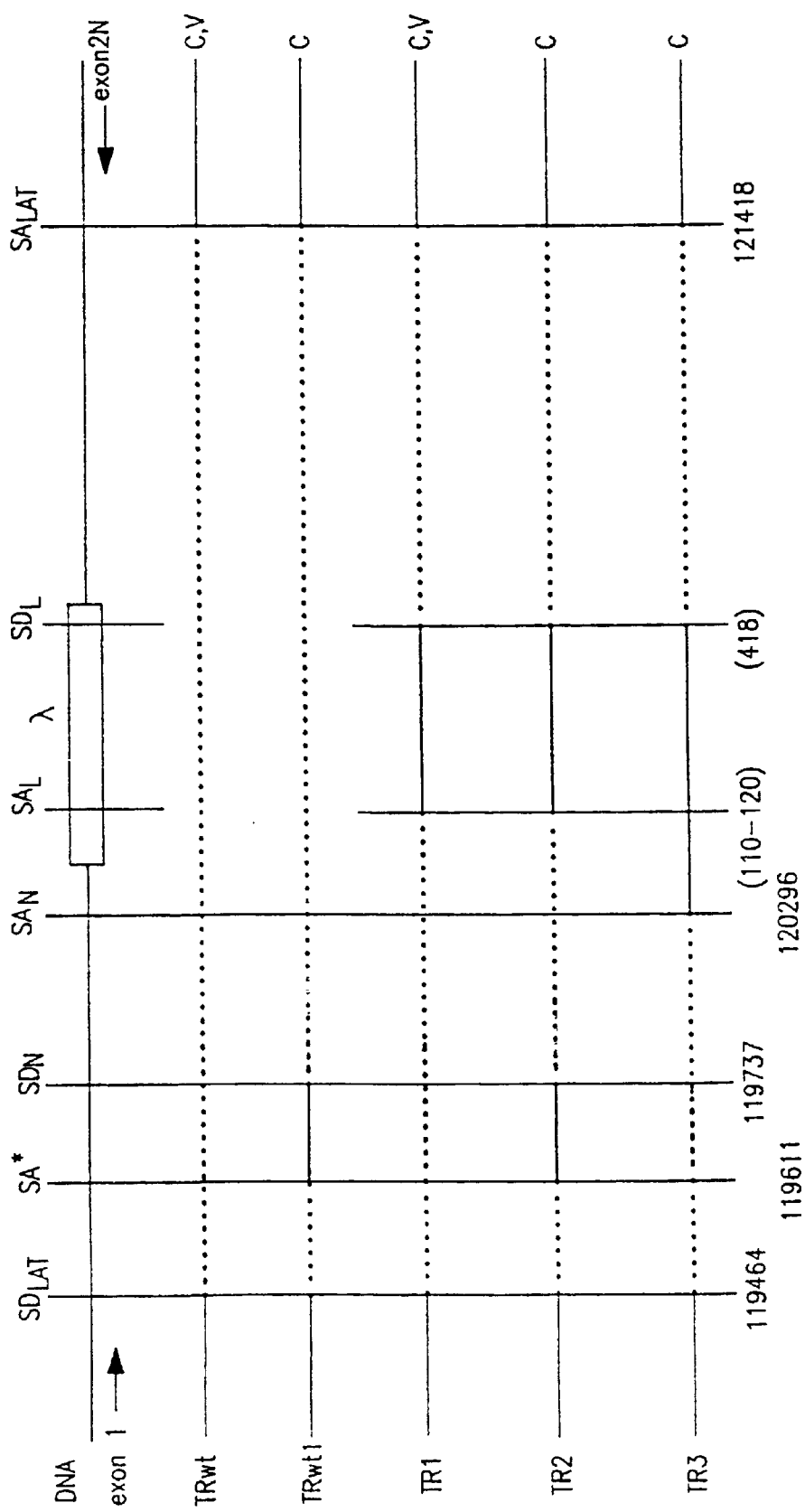
FIG. 8 is a map of LAT transcripts in TB1 virus and pHλ− construct. The first line represents the genomic DNA LAT locus in TB1 and pHλ−. The shaded box represents the λ DNA insert. $SD_{LAT}$ and $SA_{LAT}$ indicates SD and SA sites used in HSV-1 and in the wild-type (wt) construct to generate the 2.0 kb LAT intron. $SD_N$ and $SA_N$ show the splice sites used to generate the 1.5 kb LAT during latency in neurons. $SD_L$ and $SA_L$ indicate the sites acting as SD and SA in the lambda sequence. SA* localizes a cryptic SA site in the 2.0 kb LAT. The nucleotide positions on the HSV genome are numbered according to D. J. McGeoch et al, 1988, *J. Gen. Virol.*, 69:1531–1574]. Different transcripts (TR) identified after RT-PCR using primers Exon 1 and Exon 2n (arrows) are represented with exons as solid lines and introns as dotted lines. TRwt represents the wild-type transcript from construct "wt" (C) and HSV-1 strain F (V). TRwt1 is a transcript produced only after transfection of the wt construct (C). TR1, 2 and 3 are transcripts from pHΔ− construct (C) and/or TB1 virus (V).

The forward primer (Exon 1) was located in exon 1 and the reverse primer (Exon 2n) was located after the end of the 2.0 kb LAT (FIG. 8). Following amplification, a 245 bp fragment could be detected if the 2.0 kb sequence was excised, whereas no cDNA is amplified from the primary transcript. After infection of CV-1 cells with HSV-1 strain F, a 245 bp product was detected. The same band was observed following expression of the cloned LAT in wt, pΔHpa and pHλ+ constructs. The higher molecular weight bands of cDNA following transfections correspond to alternatively spliced cDNAs resulting from the vector expression system and may not be biologically relevant for the virus.

No fragments were amplified from cellular cDNA or when cDNA was omitted. None of these bands were observed in absence of RT.

In the case of TB1 virus and the pHλ- construct a shift of the mature exons bands is observed on the gel which is consistent with the larger size exons previously detected by Northern blot (Example 11). In that case heterogeneity of the RT PCR product, though more prevalent after transfection, is observed to a lesser extent when cells were infected with TB1. In addition, a positive amplification of TB1 LAT cDNA with primers specific to sequences in the first and the second LAT exons indicated the presence of a mature spliced transcript. This shows that a LAT primary transcript as well as a spliced mature RNA are produced by TB1 during productive infection and indicates that RNA mutation did not affect directly transcription from the LAT promoter.

Major products of the RT-PCR were extracted from the gel and cloned. A number of representative clones were sequenced and the more significant splicing products are shown in FIG. 8. The wt viral transcript, the splicing of which leads to the production of 2 kb LAT, is shown as well as an alternatively spliced transcript present only after transient transfection of the wt plasmid. The transcript (TR1) was the most abundant in pHλ- transfected cells and TB1 infected cells. Other minor transcripts (TR2 and TR3), all larger than TR1, were detected in transiently transfected cells. Though they are overrepresented in transfection assay and might be irrelevant for the virus, these transcripts indicated that known neuron specific ($SD_N$ and $SA_N$) and cryptic (SA*) splice sites can be used in non neuronal cells during LAT splicing. Interestingly, in all altered LATs from TB1 or pHλ- the 945 bp downstream intron is always conserved, as well as the SD site in the lambda sequence (GCAG|GTAA) [SEQ ID NO:34] at position 418 of the insert. In contrast, the lambda specific splice acceptor site ($SA_L$) appeared to be less conserved and varied around positions 110–120 of the lambda sequence.

Elucidation of the sequence of these mature transcripts together with the northern analysis showed that the insert of phage DNA in TB1 results in the addition of a SD and SA site in the middle of the 2.0 kb LAT intron. The resulting mature transcript contained an additional exon of lambda-derived RNA. The LAT intron upstream of this new lambda exon did not accumulate and was not detected by Northern blot (Example 11). On the contrary, the downstream intron could be seen on Northern blots of Example 11 indicating its remarkable stability similar to full-length 2 kb LAT.

EXAMPLE 13

Mapping of the Stability Determinant to the 3' End of the 2.0 kb LAT

Figure 9A:
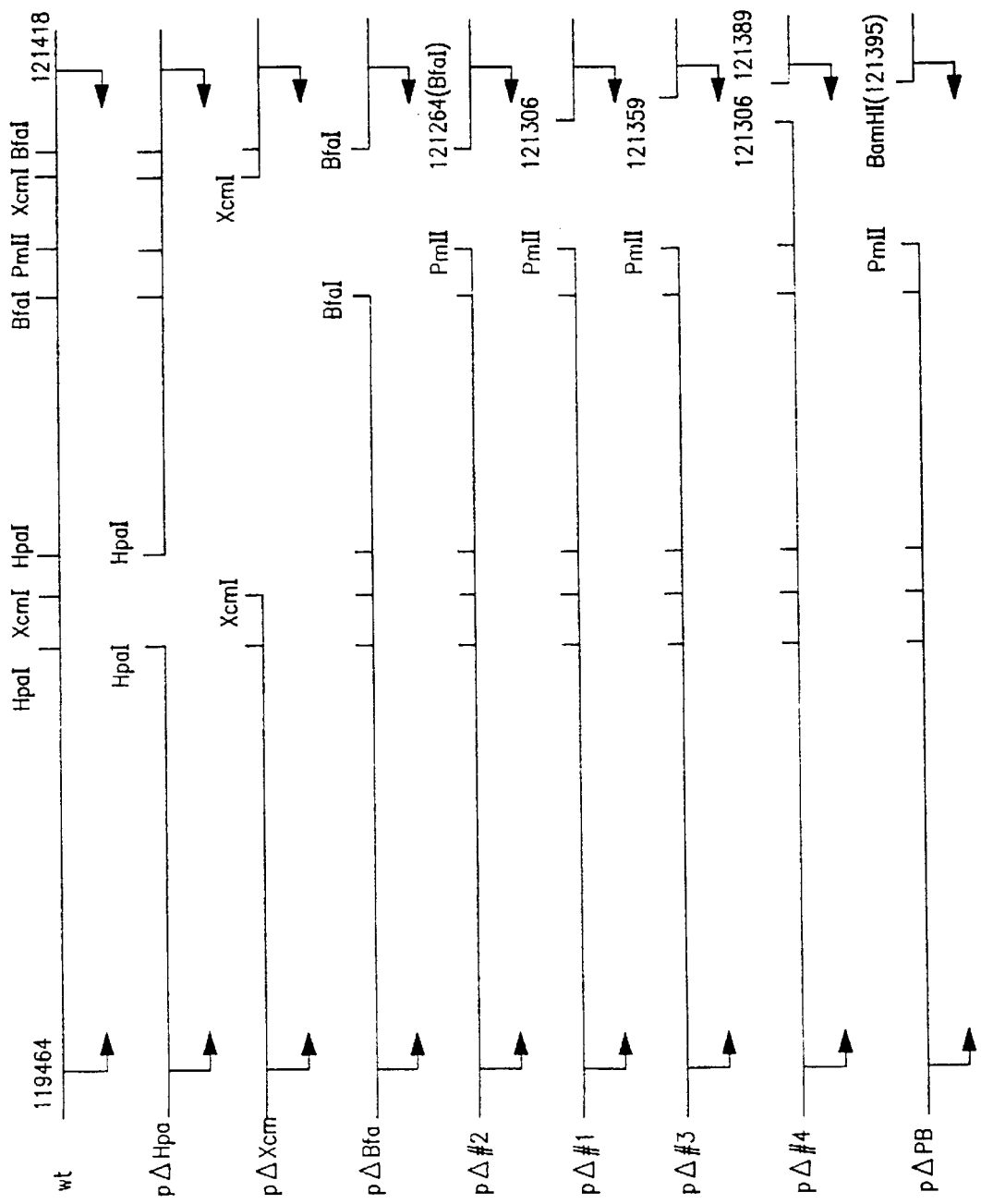
FIG. 9A is a map of the different deletion mutants, showing the 2.0 kb LAT region with SD and SA sites (arrows) for each construct. The relevant restriction sites are indicated in bold when they were used in mutagenesis.

Based on the TB1 virus and pHλ- construct, it appeared that the determinant for stability of the LAT intron resided in the 3' half of 2.0 kb LAT. To map this region more precisely, a series of deletions covering the region downstream of the HpaI sites were engineered in the same expression system (FIG. 9A). Vectors expressing LAT deletion mutants were transiently transfected in Cos-1 cells and LAT RNA was analyzed by Northern blot. Harvesting occurred 40 hours after transfection with pLAT or different mutant constructs (Example 8; pΔHpa, pΔXcm, pΔBfa, pΔ#2, pΔ#1, pΔ#3, pΔPB, pBam). Five micrograms of LAT RNAs were analyzed by Northern blot.

The probe used in this Northern blot specifically detected the 5' half of the 2.0 kb LAT intron in a region not affected by deletions in any of the mutants. The 2.0 kb intron is expressed following the transfection of the wt construct and no hybridization was visible in non transfected cells. For all but two of these mutants (pΔ#3 and pΔPB), the presence of a stable but variable sized intron due to the deletion is detected.

Deletions pΔ#3 and pΔPB affect the accumulation of intron although low amounts of primary transcript could be detected as well as for all the other constructs. In some instances, the intron band appeared as a doublet in the wt or mutant constructs. In this type of gel electrosphoresis this might be explained by the presence of non-linear RNA with nicked or linearized LAT RNA. The absence of visible intron can be due to inefficient transcription, defect in splicing or rapid degradation of an unstable intron.

To clarify this point, the same blot was rehybridized with the Sty-Sty probe specific for the Exon 1 of LAT (FIG. 9B). For all transfected constructs a band corresponding to the mature spliced exons (1.4 kb) was detected. This indicated that in all cases, transcription and splicing of LAT occurred without major recombinations or alterations as reported for TB1.

To understand the effects of these mutations, the stability of the intron was quantified using a phosphoimager to measure the intensity of each band. The relative stability of the intron was assessed by calculating the ratio intron over exons for each mutant. This approach eliminates artifacts due to differences in transfection efficiency, transcriptional levels or amount of RNA loaded in each well because introns and exons are produced at the same rate in any mutant. Since spliced exons are similar in all constructs, their stabilities are assumed to be the same regardless of the mutation affecting the intron, thus a difference in ratio is a measure of intron stability. In that case differences in ratio is a measure of intron stability.

Figure 10:
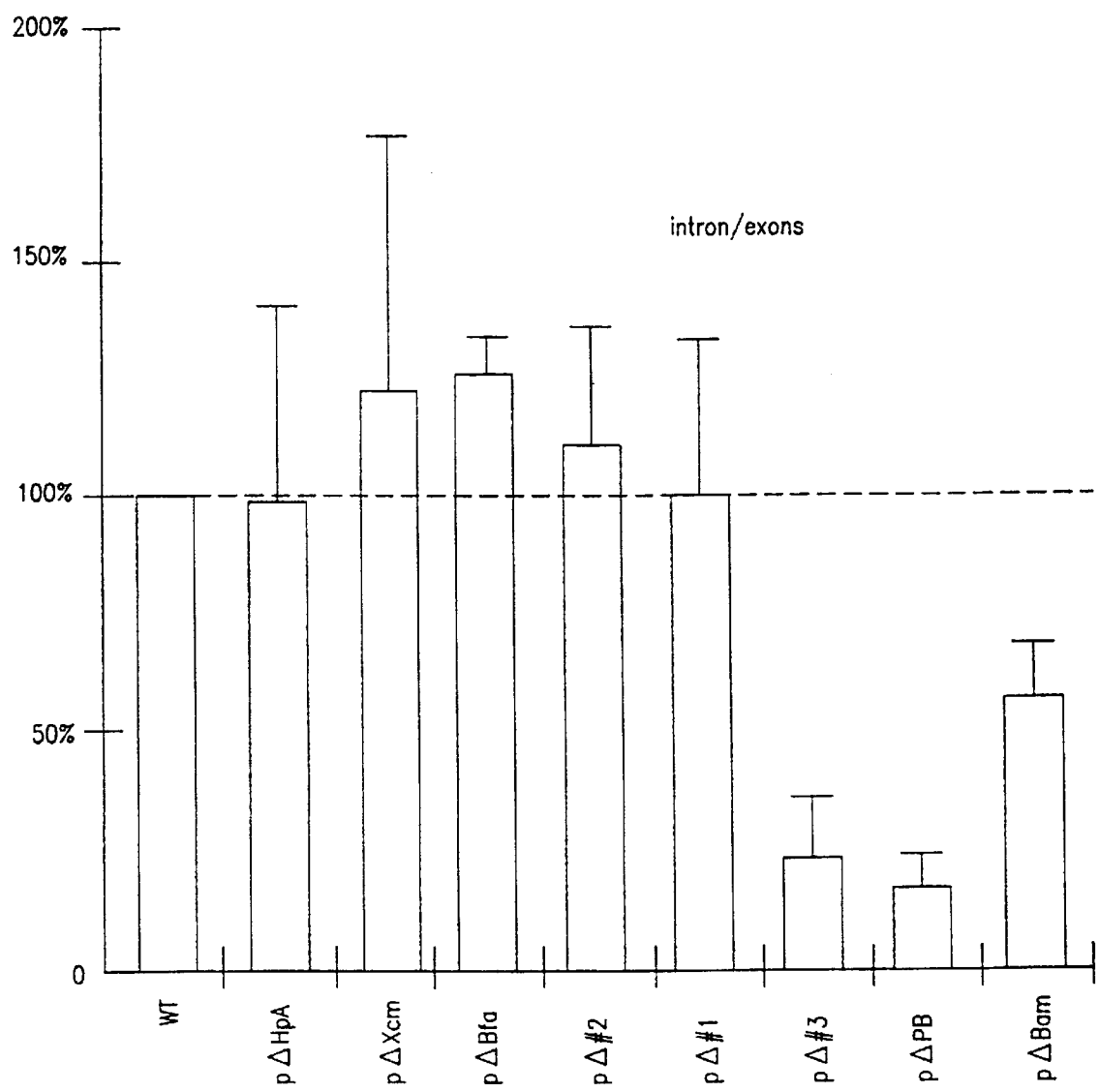
FIG. 10 is a graph of the intron band revealed in a Northern blot from Cos-1 cells transfected with the wild-type (wt) construct or different mutant constructs (pΔHpa, pΔXcm, pΔBfa, pΔ#2, pΔ#1, pΔ#3, pΔPB, pBam) and also showing non-infected Cos-1 cell RNA. Also on the graph is the 1.4 kb exon band from the same blot reprobed with the Sty-Sty probe specific for the Exon 1 of LAT. The graph is quantified for each mutant of Example 13 as well as in two other independent transfection experiments. The ratio intron/exons is represented in the histogram. This ratio was fixed to 100% for the wt construct (dotted line) in each of the experiments and ratios for each mutant were calculated relative to this standard. Error bars represent ± one standard deviation

FIG. 10 is a summary of three independent transfection experiments. In order to compare these different results, the result obtained with the wt construct was normalized to 100% in each experiment and represented the standard stability of the 2.0 kb LAT intron. Confirming the direct observation of the northern blot, deletions ΔHpa, ΔXcm, ΔBfa, Δ#2 and Δ#1 do not significantly alter LAT stability. On the contrary Δ#3 and ΔPB show a marked reduction of stability to about 10% of the wt construct. Interestingly, the pBam mutant which carries only a 3 base substitution (FIG. 9B) showed a stability reduced to 60% of wt. Based on mutants Δ#1 and Δ#3, a region necessary for stability between nucleotide 121306 and 121359 was identified. On the other hand, the region around nucleotide 121395 where the BamHI site was created in pBam appears also to play a role in conferring stability to the 2.0 kb LAT.

EXAMPLE 14
Alteration of 2.0 kb LAT Stability by Limited Mutations

These regions were further investigated by small deletions, substitutions or insertions in the last 110 bp of the LAT intron (FIG. 9B; mutants pBam, pCons, pΔA, pΔG, pΔ#4, pΔ#5, pY−, pY+). After transfection into Cos-1 cells, the LAT RNA produced by these mutants or by wt were hybridized with a probe detecting all primary transcripts, introns and exons and analyzed by northern blot. Contrary to the first set of mutants, these deletions were small and a probe hybridizing to both intron and exons could be used without having overlap of intron and exon bands (FIG. 10). Again the wt construct was used as control, showing all three transcripts, primary transcript, accumulating intron and mature exons. pΔG showed accumulation of the LAT intron. pBam, as before, showed a reduced amount of intron. All other mutants produced very low or undetectable level of intron.

Stability of the intron in pΔ#4 and pΔ#5 appeared to be significantly reduced although these mutants seemed to be impaired in splicing. The major product of the pCons construct in which a consensus branch site was created were the spliced exons. On the contrary, mutants pΔ#4 and pΔ#5 showed mainly an accumulation of the primary transcripts.

Figure 11A:
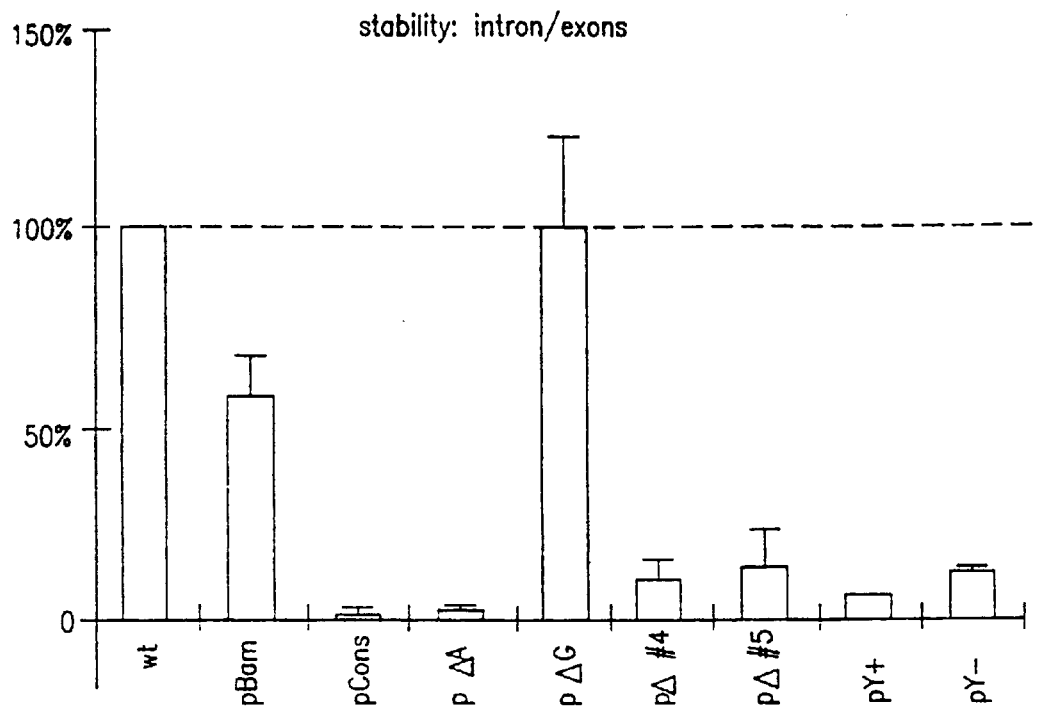
FIG. 11A illustrates the relative stability of the mutant intron 2.0 kb LAT assessed by the ratio intron/exons and expressed as percentage of wild-type (wt) 2.0 kb LAT intron stability. Bands from northern blot described in Example 14, as well as blots resulting from two other independent transfections were quantified. Asterisks indicate introns produced after inefficient splicing.

A quantification of the stability of the intron is reported in FIG. 11A. Three independent transfections were performed and the ratio of intron over exons was calculated as described immediately above. The pBam scored 60% of stability as compared to wt. The small deletion of pΔG did not affect stability although the wt branch point was deleted in this construct. The creation of a mammalian consensus branch site in pCons dramatically reduced the stability of the 2.0 kb LAT intron as well as the deletion of the corresponding sequence in pΔA. Similarly a yeast consensus branch site introduced in pBam (mutant pY+, FIG. 11A) resulted in the total disappearance of the intron. Interestingly the insertion of the same sequence in the opposite orientation (no consensus branch site) in pY− also created an unstable intron (lane 8). Although stability of the intron from mutants pΔ#4 and pΔ#5 was significantly reduced, these mutants appeared to be imparied in splicing.

EXAMPLE 15
Relationship Between Splicing Efficiency and Intron Stability

Figure 11B:
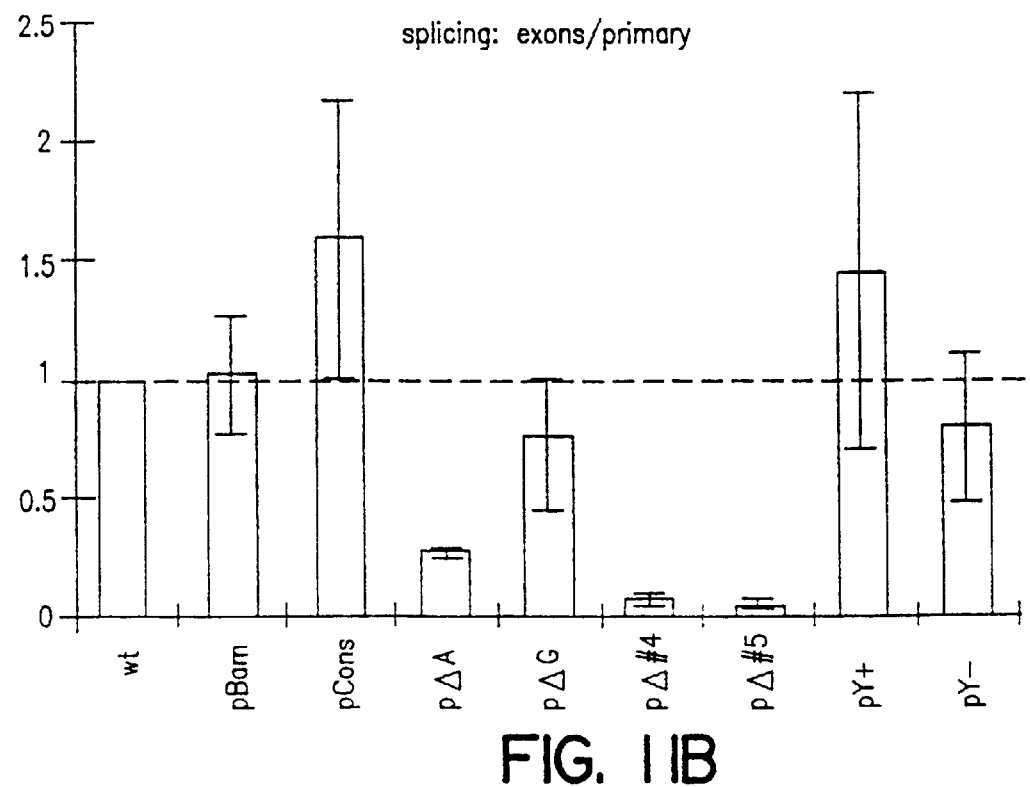
FIG. 11B illustrates splicing efficiency calculated by the ratio exons/primary transcript. This ratio has been arbitrarily set to 1 for the wild-type (wt) construct of FIG. 7B. A low ratio reflects an inefficient splicing. Error bars show ± one standard deviation.

To quantify the splicing efficiency, the ratio of the intensity of the mature exons over the primary transcript was calculated and set to 1 for the wt construct (FIG. 11B). Since the stability of the primary transcript might be affected by the mutation, these numbers could only give an estimation of splicing efficiency.

It appeared that pBam, pΔG and pY− were as effective as wt. Mutants carrying a consensus branch point (pCons and pY+) had an increased efficiency of splicing although their introns did not accumulate. The 8 bp deletion in pΔA induced a reduction of 70% of splicing efficiency whereas deletions in pΔ#4 and pΔ#5 had a more drastic effect and decreased splicing to 10% or less of the wt level. This genetic approach mapped in the 3' end of the 2.0 kb LAT two regions involved in stability of the intron overlapping with a region important for splicing efficiency.

A model of interaction of these regions is presented in FIGS. 12A–12J, discussed below.

EXAMPLE 16
Selection of Branch Points in Mutant LATs

Evidence that the branch point of the 2.0 kb LAT located in this region is guanosine, and is likely unique and more resistant to enzymatic debranching indicated that it might play a role in enhancing stability along with the hairpin structure. Though deletion of the 2.0 kb LAT branchpoint and surrounding nucleotides in pΔG did not directly alter stability, it was important to determine how the different mutations affecting stability would affect branching.

The branch-RT PCR method described in Example 6 above was used to map the branch points of the different mutants. Briefly described, gene specific cDNA was synthesized with degenerate oligo Branch as primer from total RNA of transfected cells. Then, amplification by PCR was performed with primers PFPML and PREND. Total RNA from cells transfected with wt and mutant constructs (pBam, pCons, pΔG, pΔA, pΔ#4, pΔ#5, pY−, pY+; see FIG. 12) was used as template. RNA from non-transfected cells was used as negative control. RT-PCR products were separated on a 2% agarose gel. The major bands o-each reaction were purified and cloned. Several clones corresponding to each band were grown and sequenced.

For the wt construct two PCR products of 250 and 300 bp were identified and sequenced. The top band indicated the LAT branchpoint at the G (121344) previously identified in transfections and in HSV-1 strain F infected cultured cells or latently infected ganglia. The lower band may be due to a possible mispriming of the oligo used as primer for cDNA synthesis at nucleotide 121283, because of its sequence similarities in this region to the 5' end of the intron as reported above. However, branching remained possible at that site. In the case of the pCons mutant in which a mammalian consensus branch site (CACUG<u>A</u>C with the branchpoint underlined; SEQ ID NO:35 was engineered leading to the production of an unstable intron, a different PCR product was amplified. Sequencing revealed a branchpoint at the consensus site in position 121394. The pBam construct which showed a partially reduced stability of the intron also had an intermediate pattern in this RT experiment. In addition to the 2 bands seen with wt construct, a third slow migrating band was also visible in the gel. It appeared that the wt G nucleotide (121344) was still used but a downstream branch region was also used in certain introns at position 12143941 (AUCC<u>U</u>CC; SEQ ID NO:36). This region is also used for branching of the intron produced by pY−. The related clone, pY+ carrying a yeast consensus branch point used preferentially this consensus for branching. In the cases of pΔA4 and pΔ#5 with deletions in the hairpin, splicing is impaired but the low amounts of introns also display altered branchpoints at different positions in this area without strong preferences. In mutant pΔA, with a 8 bp deletion immediately upstream of the polypyrimidine tract, the branchpoint was also relocated to different sites in the loop of the hairpin.

Contrary to all the other mutants analyzed, pΔG displayed RT-PCR bands similar to wt, although with different intensities. The lower band is due to mispriming at nucleotide 121283 as observed for wt. Sequencing of the higher band indicates that branching occurred around the location used by the wt, relative to the hairpin. However, due to the deletion, the branchpoint is now different.

A summary of the different branch points in these mutants is reported on a model of RNA secondary structure located at the 3' end of the 2 kb LAT intron (see FIGS. 12A–12J).

From these experiments, several conclusions can be drawn. First it appears that the 3' half of the 2 kb LAT by itself contains the necessary elements to confer stability to the LAT intron in tissue culture. The sequences at the 5' end of the intron, other than the GTA involved in branching to form the lariat, do not appear to be crucial for LAT stability. The panel of LAT deletion plasmids identifies the region conferring stability to the last 100 bp of the 2 kb LAT intron. The region between nucleotides 121306 and 121359 encompassing the wt branchpoint at position 121344 and part of a putative hairpin structure appear to be important to stability of the LAT intron.

The loop and the upper stem region are required for efficient splicing (mutant pΔ#5) and also account for stability. The structure at the base of the stem is essential for stability but is less involved in controlling splicing efficiency. Minor substitutions in this region significantly reduce intron stability (mutant pBam). Introduction of a second hairpin or deletion of this region have a more drastic destabilizing effect (mutants pY− and pΔA). Stem-loop structures are known to play important roles in stabilization of numbers of RNAs. They can bind specific proteins or build nuclease resistant cores. The presence of such a structure in the tail of the 2.0 kb LAT lariat could possibly play a role in stability of the intron using either property.

However the most interesting feature of this stem-loop is its ability to direct selection of branch sites. There are no consensus branch sites near the 3' end of the 2.0 kb LAT intron. Thus the branching of this intron occurs at a non conventional site. Through RNA folding this point is brought close to the end of the polypyrimidine tract where conventional branch point are usually found. On the contrary the suboptimal branch sequence (GAGGGAG; SEQ ID NO: 37) hypothesized by Wu et al appeared not to be used by the virus. Structurally it is sequestered in the hairpin which is a location known to prevent efficient branching. Correction of this suboptimal consensus (GAGGGAG; SEQ ID NO: 37) to a mammalian branch point (CACUGAC [SEQ ID NO: 35] in pCons) or insertion of a yeast consensus sequence (UACUAAC [SEQ ID NO: 1] in pY+) lead to the complete destabilization of the intron. In both cases the branches occurred preferentially at the new branch site.

The 3 bp substitution of the pBam mutant at the base of the stem disrupts one GC pair and extends the polypyrimidine tract by 3 nucleotides. The original branch point is still used by this mutant, but a significant portion of introns branch at the opposite side of the hairpin (FIGS. 9B and 12B). The overall 60% stability of the pBam intron reflects the proportion of these two populations of introns, stable or unstable according to their branch point. The pY− intron which branches mainly in the same wrong side of the hairpin is essentially not stable.

Surprisingly, deletion of the wt branch point (pΔG) region did not significantly affect stability. The wt branch nucleotide is by itself an exception known to be resistant to debranching opening the way to intron degradation. In pΔG the branching occurs in the same region although the sequence is different and the intron is still accumulating. The mutant pΔ#3 also deletes a large region upstream of the hairpin and does not produce a stable intron probably because its deletion extend into the stem of the hairpin and destabilizes this region.

The 2 kb LAT branchpoint nucleotide (G) is unusual because such nucleotides are normally adenines. Availability and proper selection of branch sites are important for reliable splicing. Mutations or deletions of common branchpoints usually lead to exon skipping due to lack of recognition of the mutated intron (IL3, androgen receptor). Complex mechanisms involved in branchpoint choice include the consensus sequence and surrounding area, the type of polypyrimidine tract and secondary structures. Efficient splicing of LAT in absence of consensus branch point is achieved by direct selection of non consensus sites mediated by RNA secondary structure. This mechanism is quite efficient since the presence of a strong consensus site increased splicing efficiency by a 1.5 to 2 folds only. On the other hand, deletion of the loop decrease splicing efficiency by 90% probably due to the absence of recognition of a suitable branch point.

As represented in FIGS. 12A–12J, the HSV-2 LAT sequence (McGeoch) in this region is able to form the same secondary structures and does not have a consensus branch point. The stem of the hairpin is identical to the HSV-1 counterpart and divergence is found in the polypyrimidine tract and in the loop. One can reasonably hypothesize a similar regulation leading to the stability of that intron. On the contrary another HSV-1 stable intron from the ICP0 gene might behave differently. This intron uses 4 different splice acceptor sites within 300 bp. A perfect consensus branch point is present associated to the most upstream acceptor site whereas 6/7 bp matches can be found for each other. An intron spliced from the constant region of the T-cell receptor accumulates in T cells as a lariat. Five out of 7 bases match the consensus branch site and no strong stem-loop structure can be detected at the 3' end of this intron. A short sequence (AUUUUC; SEQ ID NO:38) at the end of the polypyrimidine tract was proposed to be involved in stability based on comparisons with other similar stable introns. This sequence is absent in the 2.0 kb LAT intron.

EXAMPLE 17
Using the LATin to Stabilize an Unstable Gene

An example of a plasmid vector useful in a method to stabilize an unstable transcript and permit enhanced recombinant expression of the gene product is described with reference to FIG. 13.

As described in Example 2 above, the 2.8 kb fragment of the mLAT gene was isolated as a PstI-MluI restriction fragment from vector pGEM4Z PstI-MluI [Spivack, 1991; Promega]. The PstI-MluI DNA was removed from this plasmid by digestion with the same restriction enzymes and cloned into the polylinker site of the eukaryotic expression vector pcDNA3 (Invitrogen). The resulting plasmid pcDNA3/PstI-MluI, was digested with XcmI, which permitted removal of about 800 bp from the middle of the 2.0 kb LAT intron.

A DNA sequence was constructed to contain a ribosome entry sequence from the EMC virus [Jang et al, 1989, *Genes & Devel.*, 4:1560–1572] ligated to the DNA sequence for the green fluorescentrotein [commercially available from Clontech]. This sequence had flanking restricting sites which complemented XcmI, which can be generated using standard techniques.

This DNA sequence was ligated to the XcmI cleaved pcDNA3/PstI-MluI to create the plasmid indicated in FIG. 13. The resulting pcDNA3/GFP plasmid contained HSV-1 LAT 5' sequence spanning from about nucleotide 1 to about nucleotide 930 of the 2.0 kb LAT, which included about 100 bp of LAT sequence including the SD site, followed by the EMC-GFP insert, followed by a sequence spanning about nucleotide 1740 to nucleotide 2000 of the 2.0 kb LAT sequence which spans about the last 200 bases of the 2. b kb LAT and the SA site.

This plasmid contains the CMV promoter described in Example 2 located 5' to the SD site.

This plasmid is conventionally transfected into a host cell, such as a COS-1 cell, and upon culturing of the transfected cell, GFP is produced in quantities which exceed quantities of GFP produced by other conventional plasmids in the same host cell and under the same conditions. GFP fluorescence is determined using the assays and other methodologies described by its manufacturer (Clontech).

EXAMPLE 18
Half-life of the 2.0 kb LAT Intron in Transiently Transfected Cells

A tetracycline inducible gene expression system (Gibco-BRL) was employed to measure the stability of the 2.0 kb LAT intron in transiently transfected COS-1 cells. Plasmid pTet-LAT contains the PstI-MluI fragment of HSV-1 strain F, encompassing the 2.0 kb LAT, and the bovine growth hormone polyadenylation signal from plasmid pcDNA3 (Invitrogen), under the control of a tetracycline inducible promoter pTet. Plasmid tTet-t-TAK (Gibco-BRL) encodes a fusion protein of the tetracycline DNA binding domain and the transactivation domain of HSV Vp16 under the control of the tetracycline inducible promoter. In the presence of tetracycline, transcription of both genes occurs; when tetracycline is absent, a low level of basal transcription occurs.

COS-1 cells were transfected with pTet-tTAK and pTet-LAT in the presence of tetracycline. Approximately 24 hours post-transfection plasmid expression was induced for 12 hours by removal of tetracycline and then repressed again by addition of tetracycline. Total RNA was isolated from control uninduced cells at 0 hours post-induction and induced cells at 0, 6, 12, 18, 24, 30, and 36 hours post-induction. RNAs were analyzed by Northern hybridization with probe B. The amount of LAT detected at each timepoint was determined by quantitation with a phosphorimager (Molecular Dynamics).

Figure 14:
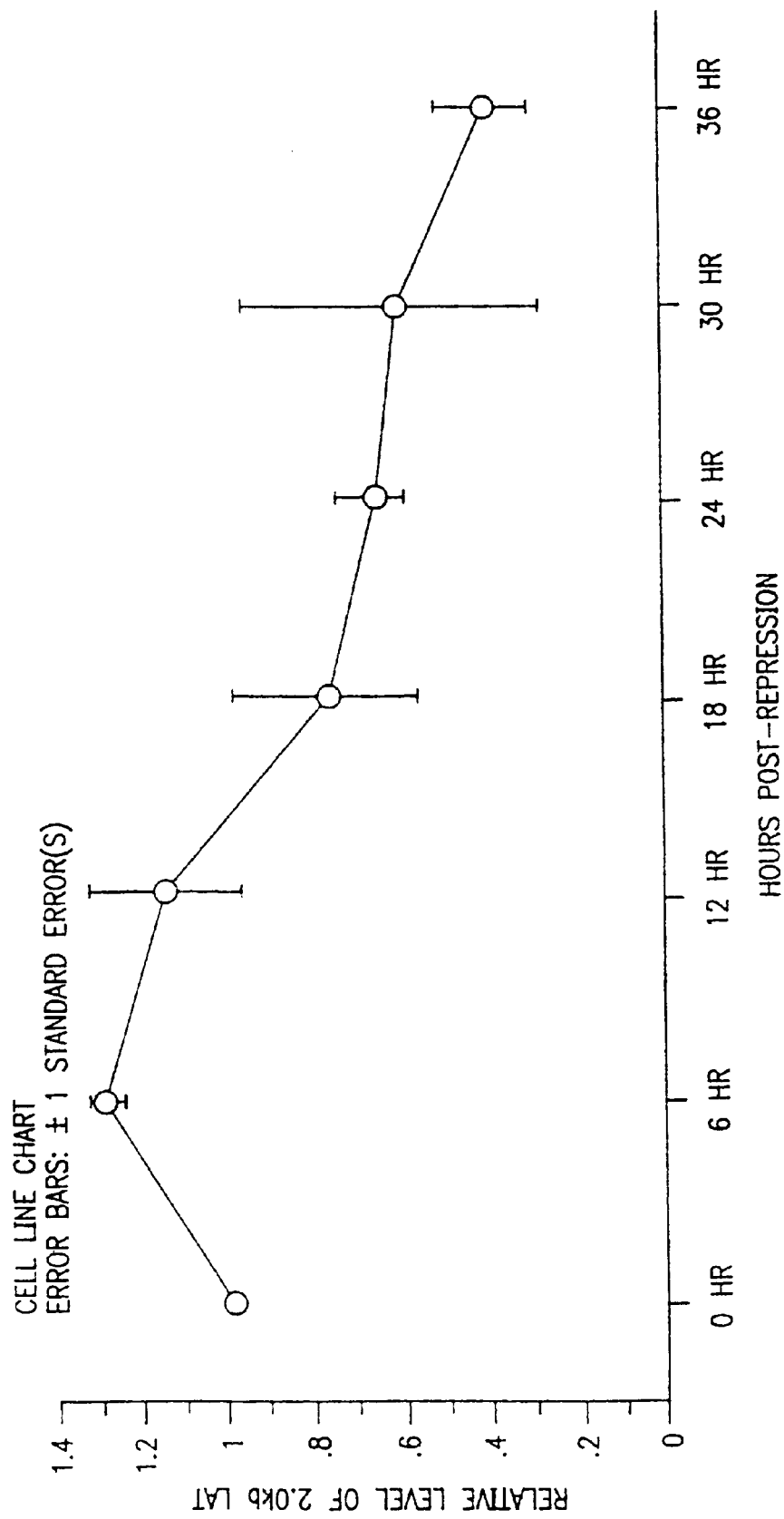
FIG. 14 is a graph illustrating the half-life of the 2.0 kb LAT intron in transiently transfected cells, plotting the relative level of 2.0 kb LAT vs. hours post-regression as described in Example 18 below. The amount of LAT detected at each timepoint was normalized to the relative increase in μg of RNA isolated at each timepoint, and the background level of LAT expression in uninduced cells was subtracted from the level of LAT in induced cells. The results of three individual experiments were compiled and mean level of LAT over time is presented. Error bars represent ±1 standard deviation(s).

To normalize for cell growth occurring from the first timepoint to the endpoint of the experiment, the relative amount of LAT present at each timepoint was normalized to the relative increase in $\mu$g of RNA isolated at each timepoint. The background level of LAT expression in uninduced cells was subtracted from the level of LAT in induced cells at each timepoint. The results of three individual experiments were compiled and a graph of the mean level of LAT present over time is presented in FIG. 14. Regression analysis of this data was also done using StatView software (Abacus Concepts, Inc., Berkley, Calif., 1994). The $R^2$ value obtained is high, 0.82, indicating that the relative level of LAT decreases over time in a linear manner. This suggests that LAT decays linearly.

From these results the half-life of the 2.0 kb LAT is approximately 33 hours, which suggests that this intron is extraordinarily stable, in dramatic contrast to most introns which rapidly degrade within seconds of release [see, e.g., M. J. Moore et al, 1993, cited above].

All above-referenced published documents are incorporated by reference herein. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A polynucleotide molecule comprising:
   (a) a polynucleotide sequence encoding a gene product;
   (b) a 5' sequence of an intron comprising the splice donor and splice acceptor of said intron;
   (c) a 3' sequence of said intron comprising a hairpin structure adjacent to the branchpoint of said intron;
   wherein the sequence (a) is flanked by the sequences (b) and (c), and wherein said polynucleotide molecule stably expresses said gene product in culture.

2. The molecule according to claim 1 further comprising an internal ribosome entry site.

3. The molecule according to claim 1, consisting of RNA.

4. The molecule according to claim 1, consisting of DNA.

5. The molecule according to claim 1 wherein said hairpin is 5' to said branchpoint.

6. The molecule according to claim 1 wherein said hairpin is 3' to said branchpoint.

7. The molecule according to claim 1 wherein said intron is the 2.0 kb LAT of a herpes virus.

8. The molecule according to claim 7 comprising, from 5' to 3':
   (a) a polynucleotide sequence comprising a 5' sequence of the 2.0 kb LAT of a herpes virus;
   (b) a polynucleotide sequence comprising an internal ribosome entry site;
   (c) a polynucleotide sequence comprising an open reading frame encoding a selected gene product; and
   (d) a polynucleotide sequence comprising a 3' sequence of the 2.0 kb LAT of a herpes virus.

9. The molecule according to claim 7 wherein said 5' sequence (b) comprises a polynucleotide sequence spanning from about 2 to about 20 nucleotides 5' to the 5' nucleotide of said 2.0 kb LAT through about 2 to about 20 nucleotides 3' to said 5' nucleotide.

10. The molecule according to claim 7 wherein said 3' sequence (c) comprises a polynucleotide sequence of about 80 nucleotides.

11. The molecule according to claim 7 wherein said 3' sequence (c) comprises a polynucleotide sequence spanning from about 75 to about 300 nucleotides 5' to the 3' nucleotide of said 2.0 kb LAT through about 2 to about 20 nucleotides 3' to said 3' nucleotide.

12. The molecule according to claim 11 wherein said 3' sequence (c) comprises a polynucleotide sequence spanning from about 300 nucleotides 5' to the 3' nucleotide of said 2.0 kb LAT through about 2 to about 20 nucleotides 3' to said 3' nucleotide.

13. The molecule according to claim 11 wherein said 3' sequence (c) comprises a polynucleotide sequence spanning from about 200 nucleotides 5' to the 3' nucleotide of said 2.0 kb LAT through about 2 to about 20 nucleotides 3' to said 3' nucleotide.

14. The molecule according to claim 11 wherein said 3' sequence (c) comprises a polynucleotide sequence spanning from about 150 nucleotides 5' to the 3' nucleotide of said 2.0 kb LAT through about 2 to about 20 nucleotides 3' to said 3' nucleotide.

15. The molecule according to claim 1 wherein said 3' sequence (c) comprises a splice acceptor sequence.

16. The molecule according to claim 2 wherein said internal ribosome entry site sequence is a viral sequence.

17. The molecule according to claim 16 wherein said ribosome entry site sequence is the EMC virus internal ribosome entry site sequence.

18. The molecule according to claim 2 wherein said internal ribosome entry sequence is a mammalian sequence.

19. The molecule according to claim 18 wherein said internal ribosome entry site sequence is BiP.

20. The molecule according to claim 1 further comprising a promoter sequence located 5' to said sequence (b) and operably linked within said molecule to direct expression of said selected gene in a host cell.

21. The molecule according to claim 1 wherein said selected gene is an unstable transcript.

22. The molecule according to claim 21 wherein said selected gene encodes a protooncogene.

23. The molecule according to claim 1 wherein said selected gene encodes a growth factor.

24. An expression vector comprising:
   (a) a polynucleotide sequence encoding a gene product;
   (b) a 5' sequence of an intron comprising the splice donor and splice acceptor of said intron;
   (c) a 3' sequence of said intron comprising a hairpin structure adjacent to the branchpoint of said intron;
   wherein the sequence (a) is flanked by the sequences (b) and (c); and wherein said sequence (a) is under the control of regulatory sequences which direct stable expression of said gene product in a host cell.

25. A host cell transfected with a vector of claim 24.

26. A method for stably expressing an unstable gene transcript to permit enhanced expression of said gene product, the method comprising the steps of:
   culturing a host cell transfected with an expression vector comprising:
   (a) a polynucleotide sequence encoding a gene product;
   (b) a 5' sequence of an intron comprising the splice donor and splice acceptor of said intron; and
   (c) a 3' sequence of said intron comprising a hairpin structure adjacent to the branchpoint of said intron;
   wherein the sequence (a) is flanked by the sequences (b) and (c); and wherein said sequence (a) is under the control of regulatory sequences which direct stable expression of said gene product in a host cell; and
   isolating the product of said gene from the cytoplasm of said host cell or from said culture.

27. A method for stably expressing a gene having an unstable mRNA in a cell comprising infecting said cell with a stable polynucleotide molecule comprising:
   (a) a polynucleotide sequence comprising said unstable mRNA;
   (b) a 5' sequence of an intron comprising the splice donor and splice acceptor of said intron;
   (c) a 3' sequence of said intron comprising a hairpin structure adjacent to the branchpoint of said intron;
   wherein the sequence (a) is flanked by the sequences (b) and (c), and wherein said molecule comprises regulatory sequences which direct stable expression of said gene in said cell.

* * * * *

UNITED STATES PATENT AND TRADEMARK OFFICE
CERTIFICATE OF CORRECTION

PATENT NO. : 6,159,710
DATED : December 12, 2000
INVENTOR(S) : N. Fraser

Page 1 of 3

It is certified that error appears in the above-identified patent and that said Letters Patent is hereby corrected as shown below:

Col. 1, line 38, replace "MLAT" with -- mLAT -- .

Col. 1, line 48, replace "(1994), 204:717-728" with -- (1994), Virol., 204:717-728 -- .

Col. 1, line 59, replace "MnLATRNA" with -- mLATRNA -- .

Col. 1, line 67, replace "MLAT" with -- mLAT -- .

Col. 4, line 17, replace "BstEII-BstEH;" with -- BstEII-BstEII; -- .

Col. 5, line 52, replace "pHΔ" with -- pHλ -- .

Col. 6, line 11, replace "±" with -- +/- -- .

Col. 6, line 23, replace "±" with -- +/- -- .

Col. 6, line 33, start a new paragraph with "Fig. 12B".

Col. 7, line 55, replace "stains' " with -- contains -- .

UNITED STATES PATENT AND TRADEMARK OFFICE
CERTIFICATE OF CORRECTION

PATENT NO. : 6,159,710
DATED : December 12, 2000
INVENTOR(S) : N. Fraser

It is certified that error appears in the above-indentified patent and that said Letters Patent is hereby corrected as shown below:

Col. 9, line 3, replace "nucleotide 3'" with -- nucleotides 3' -- .

Col. 12, line 33, replace "MnLAT" with -- mLAT -- .

Col. 12, line 48, replace "MLAT" with --mLAT -- .

Col. 14, line 12, replace "Example 17." with -- Example 17, --

Col. 17, line 50, replace "Sequencinp" with -- Sequencing -- .

Col. 17, line 67, delete the unnecessary space after "72° C. for" .

Col. 18, line 54, replace "conyensus" with -- consensus -- .

Col. 22, line 18, replace "McGeoch,1998" with -- McGeoch,1988 -- .

Col. 22, line 28, replace "[SEQ ID" with -- branch point -- .

Col. 22, line 34, replace "McGeoch, 1998" with -- McGeoch, 1988. -- .

UNITED STATES PATENT AND TRADEMARK OFFICE
CERTIFICATE OF CORRECTION

PATENT NO. : 6,159,710
DATED : December 12, 2000
INVENTOR(S) : N. Fraser

It is certified that error appears in the above-identified patent and that said Letters Patent is hereby corrected as shown below:

Col. 23, line 63, replace "EcoRI-HinduIII" with -- EcoRI-HindIII -- .

Col. 24, line 14, replace "pλ+" with -- pY+ -- .

Col. 24, line 25, replace "PHm1I" with -- Pm1I -- .

Col. 25, line 11, replace "wasstored" with -- was stored -- .

Col. 28, line 64, replace "End" with -- end -- .

Col. 30, line 11, replace "pAG" with -- pΔG -- .

Col. 31, line 13, replace "o-each'-" with -- of each- -- .

Col. 31, line 41, replace "pΔA4' " with -- pΔ#4 -- .

Signed and Sealed this

Twenty-ninth Day of May, 2001

Attest:

NICHOLAS P. GODICI

Attesting Officer

Acting Director of the United States Patent and Trademark Office

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
        (A) LENGTH: 7 base pairs
        (B) TYPE: nucleic acid
        (C) STRANDEDNESS: double
        (D) TOPOLOGY: unknown (ii) MOLECULE TYPE: RNA (genomic)

(xi) SEQUENCE DESCRIPTION: SEQ ID NO:1:

UACUAAC                                                                7

(2) INFORMATION FOR SEQ ID NO:2:

(i) SEQUENCE CHARACTERISTICS:
        (A) LENGTH: 23 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "probe/primer A"

(xi) SEQUENCE DESCRIPTION: SEQ ID NO:2:

CTGGGGAGGG AGACAAGAGG AAA                                             23

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "probe/primer B"

(xi) SEQUENCE DESCRIPTION: SEQ ID NO:3:

CGAGGAAGTG TGCCCGGAAG AC                                              22

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "probe/primer C"

(xi) SEQUENCE DESCRIPTION: SEQ ID NO:4:

AGACGCGCCA CGCGGAAGAC TTC                                             23

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: other nucleic acid
            (A) DESCRIPTION: /desc = "probe/primer D"

(xi) SEQUENCE DESCRIPTION: SEQ ID NO:5:

GGAGACTTCC GGGGCCGTCC                                                    20

(2) INFORMATION FOR SEQ ID NO:6:

(i) SEQUENCE CHARACTERISTICS:
            (A) LENGTH: 20 base pairs
            (B) TYPE: nucleic acid
            (C) STRANDEDNESS: single
            (D) TOPOLOGY: unknown (ii) MOLECULE TYPE: other nucleic acid
            (A) DESCRIPTION: /desc = "probe/primer E"

(xi) SEQUENCE DESCRIPTION: SEQ ID NO:6:

GGGGCATCAC TGTGTTACCC                                                    20

(2) INFORMATION FOR SEQ ID NO:7:

(i) SEQUENCE CHARACTERISTICS:
            (A) LENGTH: 24 base pairs
            (B) TYPE: nucleic acid
            (C) STRANDEDNESS: single
            (D) TOPOLOGY: unknown (ii) MOLECULE TYPE: other nucleic acid
            (A) DESCRIPTION: /desc = "prober/primer Branch"

(xi) SEQUENCE DESCRIPTION: SEQ ID NO:7:

AGAAGCAGGT GTCTAACCTA CNNN                                               24

(2) INFORMATION FOR SEQ ID NO:8:

(i) SEQUENCE CHARACTERISTICS:
            (A) LENGTH: 21 base pairs
            (B) TYPE: nucleic acid
            (C) STRANDEDNESS: single
            (D) TOPOLOGY: unknown (ii) MOLECULE TYPE: other nucleic acid
            (A) DESCRIPTION: /desc = "probe/primer End"

(xi) SEQUENCE DESCRIPTION: SEQ ID NO:8:

AGAAGCAGGT GTCTAACCTA C                                                  21

(2) INFORMATION FOR SEQ ID NO:9:

(i) SEQUENCE CHARACTERISTICS:
            (A) LENGTH: 24 base pairs
            (B) TYPE: nucleic acid
            (C) STRANDEDNESS: single
            (D) TOPOLOGY: unknown (ii) MOLECULE TYPE: other nucleic acid
            (A) DESCRIPTION: /desc = "probe/primer BranchG"

(xi) SEQUENCE DESCRIPTION: SEQ ID NO:9:

AGAAGCAGGT GTCTAACCTA CCCG                                               24

(2) INFORMATION FOR SEQ ID NO:10:

(i) SEQUENCE CHARACTERISTICS:
            (A) LENGTH: 21 base pairs
            (B) TYPE: nucleic acid
            (C) STRANDEDNESS: single
            (D) TOPOLOGY: unknown (ii) MOLECULE TYPE: other nucleic acid
            (A) DESCRIPTION: /desc = "probe/primer Exon 1"

(xi) SEQUENCE DESCRIPTION: SEQ ID NO:10:

GCTCCATCGC CTTTCCTGTT C                                              21

(2) INFORMATION FOR SEQ ID NO:11:

(i) SEQUENCE CHARACTERISTICS:
            (A) LENGTH: 19 base pairs
            (B) TYPE: nucleic acid
            (C) STRANDEDNESS: single
            (D) TOPOLOGY: unknown (ii) MOLECULE TYPE: other nucleic acid
            (A) DESCRIPTION: /desc = "probe/primer Exon 2"

(xi) SEQUENCE DESCRIPTION: SEQ ID NO:11:

TGACGTCCTC GGCGGCCTC                                                 19

(2) INFORMATION FOR SEQ ID NO:12:

(i) SEQUENCE CHARACTERISTICS:
            (A) LENGTH: 21 base pairs
            (B) TYPE: nucleic acid
            (C) STRANDEDNESS: single
            (D) TOPOLOGY: unknown (ii) MOLECULE TYPE: other nucleic acid
            (A) DESCRIPTION: /desc = "probe/primer Exon 2n"

(xi) SEQUENCE DESCRIPTION: SEQ ID NO:12:

TCCTCTGCCT CTTCCTCCTC G                                              21

(2) INFORMATION FOR SEQ ID NO:13:

(i) SEQUENCE CHARACTERISTICS:
            (A) LENGTH: 61 base pairs
            (B) TYPE: nucleic acid
            (C) STRANDEDNESS: single
            (D) TOPOLOGY: unknown (ii) MOLECULE TYPE: other nucleic acid
            (A) DESCRIPTION: /desc = "probe/primer Tail"

(xi) SEQUENCE DESCRIPTION: SEQ ID NO:13:

CAAGAGGAAA CCTCCCTCGG CCCCCGCGCT GCTTCTGGGC CGCGGGGCC GAGGAAGTGT      60
G                                                                    61

(2) INFORMATION FOR SEQ ID NO:14:

(i) SEQUENCE CHARACTERISTICS:
            (A) LENGTH: 20 base pairs
            (B) TYPE: nucleic acid
            (C) STRANDEDNESS: single
            (D) TOPOLOGY: unknown (ii) MOLECULE TYPE: other nucleic acid
            (A) DESCRIPTION: /desc = "probe/primer PFPML"

(xi) SEQUENCE DESCRIPTION: SEQ ID NO:14:

GGGGCATCAC GTGGTTACCC                                                20

(2) INFORMATION FOR SEQ ID NO:15:

(i) SEQUENCE CHARACTERISTICS:
            (A) LENGTH: 25 base pairs (B) TYPE: nucleic acid
        (C) STRANDEDNESS: single
        (D) TOPOLOGY: unknown (ii) MOLECULE TYPE: other nucleic acid
        (A) DESCRIPTION: /desc = "probe/primer PRBAM"

(xi) SEQUENCE DESCRIPTION: SEQ ID NO:15:

GAGACAAGAG GAAGGATCCC TCGGC                                                     25

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "probe/primer PFBH1"

(xi) SEQUENCE DESCRIPTION: SEQ ID NO:16:

AGGGATCCTT CCTCTTGTCT CCCTCCCAGG                                                30

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "probe/primer PRP31"

(xi) SEQUENCE DESCRIPTION: SEQ ID NO:17:

GCCAGTGTGA TGGATATCTG C                                                         21

(2) INFORMATION FOR SEQ ID NO:18:

(i) SEQUENCE CHARACTERISTICS:
        (A) LENGTH: 29 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "probe/primer PFPB1"

(xi) SEQUENCE DESCRIPTION: SEQ ID NO:18:

CCACACGTGA GACCCCCGAG ATGGGCAGG                                                 29

(2) INFORMATION FOR SEQ ID NO:19:

(i) SEQUENCE CHARACTERISTICS:
        (A) LENGTH: 29 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "probe/primer PFPB2"

(xi) SEQUENCE DESCRIPTION: SEQ ID NO:19:

CGCCACGTGG GACGGCCCCG GAAGTCTCC                                                 29

(2) INFORMATION FOR SEQ ID NO:20:

(i) SEQUENCE CHARACTERISTICS:

(A) LENGTH: 29 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "probe/primer PFPB3"

(xi) SEQUENCE DESCRIPTION: SEQ ID NO:20:

TTCCACGTGC CCCGCGGCCC AGAAGCAGC                                         29

(2) INFORMATION FOR SEQ ID NO:21:

(i) SEQUENCE CHARACTERISTICS:
        (A) LENGTH: 37 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "probe/primer PRPB6"

(xi) SEQUENCE DESCRIPTION: SEQ ID NO:21:

GGAAACCTCC CTCCCGAGGA AGTGTGCCCG GAAGACG                                37

(2) INFORMATION FOR SEQ ID NO:22:

(i) SEQUENCE CHARACTERISTICS:
        (A) LENGTH: 31 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "probe/primer PFPB7"

(xi) SEQUENCE DESCRIPTION: SEQ ID NO:22:

GAGGGAGGTT TCCTCTTGTC TCCCTCCCAG G                                      31

(2) INFORMATION FOR SEQ ID NO:23:

(i) SEQUENCE CHARACTERISTICS:
        (A) LENGTH: 37 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "probe/primer PFPB8"

(xi) SEQUENCE DESCRIPTION: SEQ ID NO:23:

GGAAACCTCC CTCCCGCGGG CGGCCTCACG CGCTACC                                37

(2) INFORMATION FOR SEQ ID NO:24:

(i) SEQUENCE CHARACTERISTICS:
        (A) LENGTH: 28 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "probe/primer PFDBG"

(xi) SEQUENCE DESCRIPTION: SEQ ID NO:24:

CGTGGCGCGT CTTACACTTC CTCGGCCC                                          28

(2) INFORMATION FOR SEQ ID NO:25:

(i) SEQUENCE CHARACTERISTICS:
    (A) LENGTH: 20 base pairs
    (B) TYPE: nucleic acid
    (C) STRANDEDNESS: single
    (D) TOPOLOGY: unknown (ii) MOLECULE TYPE: other nucleic acid
    (A) DESCRIPTION: /desc = "probe/primer PRDBC"

(xi) SEQUENCE DESCRIPTION: SEQ ID NO:25:

AAGACGCGCC ACGCGGAGGC                                       20

(2) INFORMATION FOR SEQ ID NO:26:

(i) SEQUENCE CHARACTERISTICS:
        (A) LENGTH: 36 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "probe/primer pFDELA"

(xi) SEQUENCE DESCRIPTION: SEQ ID NO:26:

CAGCGCCGGG GCCTTTCCTC TTGTCTCCCT CCCAGG                     36

(2) INFORMATION FOR SEQ ID NO:27:

(i) SEQUENCE CHARACTERISTICS:
        (A) LENGTH: 23 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "probe/primer PRDELT"

(xi) SEQUENCE DESCRIPTION: SEQ ID NO:27:

AAAGGCCCCG GCGCTGCTTC TGG                                   23

(2) INFORMATION FOR SEQ ID NO:28:

(i) SEQUENCE CHARACTERISTICS:
        (A) LENGTH: 33 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "probe/primer PRPB10"

(xi) SEQUENCE DESCRIPTION: SEQ ID NO:28:

GGAAAGGTCA GTGGGCCCCC GCGCTGCTTC TGG                        33

(2) INFORMATION FOR SEQ ID NO:29:

(i) SEQUENCE CHARACTERISTICS:
        (A) LENGTH: 31 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "probe/primer PFPB9"

(xi) SEQUENCE DESCRIPTION: SEQ ID NO:29:

CACTGACCTT TCCTCTTGTC TCCCTCCCAG G                          31

(2) INFORMATION FOR SEQ ID NO:30:

(i) SEQUENCE CHARACTERISTICS:
           (A) LENGTH: 7 base pairs
           (B) TYPE: nucleic acid
           (C) STRANDEDNESS: single
           (D) TOPOLOGY: unknown (ii) MOLECULE TYPE: RNA (genomic)

(xi) SEQUENCE DESCRIPTION: SEQ ID NO:30:

YNYURAC                                                                      7

(2) INFORMATION FOR SEQ ID NO:31:

(i) SEQUENCE CHARACTERISTICS:
           (A) LENGTH: 7 base pairs
           (B) TYPE: nucleic acid
           (C) STRANDEDNESS: single
           (D) TOPOLOGY: unknown (ii) MOLECULE TYPE: RNA (genomic)

(xi) SEQUENCE DESCRIPTION: SEQ ID NO:31:

UUCCGGG                                                                      7

(2) INFORMATION FOR SEQ ID NO:32:

(i) SEQUENCE CHARACTERISTICS:
           (A) LENGTH: 7 base pairs
           (B) TYPE: nucleic acid
           (C) STRANDEDNESS: single
           (D) TOPOLOGY: unknown (ii) MOLECULE TYPE: RNA (genomic)

(xi) SEQUENCE DESCRIPTION: SEQ ID NO:32:

UUCUAAC                                                                      7

(2) INFORMATION FOR SEQ ID NO:33:

(i) SEQUENCE CHARACTERISTICS:
           (A) LENGTH: 12 base pairs
           (B) TYPE: nucleic acid
           (C) STRANDEDNESS: single
           (D) TOPOLOGY: unknown (ii) MOLECULE TYPE: DNA (genomic)

(xi) SEQUENCE DESCRIPTION: SEQ ID NO:33:

GATCGTACTA AC                                                               12

(2) INFORMATION FOR SEQ ID NO:34:

(i) SEQUENCE CHARACTERISTICS:
           (A) LENGTH: 8 base pairs
           (B) TYPE: nucleic acid
           (C) STRANDEDNESS: single
           (D) TOPOLOGY: unknown (ii) MOLECULE TYPE: DNA (genomic)

(xi) SEQUENCE DESCRIPTION: SEQ ID NO:34:

GCAGGTAA                                                                     8

(2) INFORMATION FOR SEQ ID NO:35:

(i) SEQUENCE CHARACTERISTICS:
           (A) LENGTH: 7 base pairs
           (B) TYPE: nucleic acid (C) STRANDEDNESS: single
            (D) TOPOLOGY: unknown (ii) MOLECULE TYPE: RNA (genomic)

(xi) SEQUENCE DESCRIPTION: SEQ ID NO:35:

CACUGAC                                                                         7

(2) INFORMATION FOR SEQ ID NO:36:

(i) SEQUENCE CHARACTERISTICS:
            (A) LENGTH: 7 base pairs
            (B) TYPE: nucleic acid
            (C) STRANDEDNESS: single
            (D) TOPOLOGY: unknown (ii) MOLECULE TYPE: RNA (genomic)

(xi) SEQUENCE DESCRIPTION: SEQ ID NO:36:

AUCCUCC                                                                         7

(2) INFORMATION FOR SEQ ID NO:37:

(i) SEQUENCE CHARACTERISTICS:
            (A) LENGTH: 7 base pairs
            (B) TYPE: nucleic acid
            (C) STRANDEDNESS: single
            (D) TOPOLOGY: unknown (ii) MOLECULE TYPE: DNA (genomic)

(xi) SEQUENCE DESCRIPTION: SEQ ID NO:37:

GAGGGAG                                                                         7

(2) INFORMATION FOR SEQ ID NO:38:

(i) SEQUENCE CHARACTERISTICS:
            (A) LENGTH: 6 base pairs
            (B) TYPE: nucleic acid
            (C) STRANDEDNESS: single
            (D) TOPOLOGY: unknown (ii) MOLECULE TYPE: RNA (genomic)

(xi) SEQUENCE DESCRIPTION: SEQ ID NO:38:

AUUUUC                                                                          6

(2) INFORMATION FOR SEQ ID NO:39:

(i) SEQUENCE CHARACTERISTICS:
            (A) LENGTH: 7 base pairs
            (B) TYPE: nucleic acid
            (C) STRANDEDNESS: single
            (D) TOPOLOGY: unknown (ii) MOLECULE TYPE: RNA (genomic)

(xi) SEQUENCE DESCRIPTION: SEQ ID NO:39:

UACUACC                                                                         7

(2) INFORMATION FOR SEQ ID NO:40:

(i) SEQUENCE CHARACTERISTICS:
            (A) LENGTH: 7 base pairs
            (B) TYPE: nucleic acid
            (C) STRANDEDNESS: single
            (D) TOPOLOGY: unknown (ii) MOLECULE TYPE: RNA (genomic)

(xi) SEQUENCE DESCRIPTION: SEQ ID NO:40:

UUCUGGG 7